US008966066B2

(12) United States Patent
Luna et al.

(10) Patent No.: US 8,966,066 B2
(45) Date of Patent: *Feb. 24, 2015

(54) APPLICATION AND NETWORK-BASED LONG POLL REQUEST DETECTION AND CACHEABILITY ASSESSMENT THEREFOR

(71) Applicant: Seven Networks, Inc., Redwood City, CA (US)

(72) Inventors: Michael Luna, San Jose, CA (US); Andrei Tsõmbaljuk, Tallinn (EE)

(73) Assignee: Seven Networks, Inc., San Carlos, CA (US)

( * ) Notice: Subject to any disclaimer, the term of this patent is extended or adjusted under 35 U.S.C. 154(b) by 291 days.

This patent is subject to a terminal disclaimer.

(21) Appl. No.: 13/651,247

(22) Filed: Oct. 12, 2012

(65) Prior Publication Data

US 2013/0041974 A1    Feb. 14, 2013

Related U.S. Application Data

(63) Continuation of application No. 13/412,338, filed on Mar. 5, 2012, now Pat. No. 8,291,076, which is a continuation-in-part of application No. 13/274,248, filed on Oct. 14, 2011, now Pat. No. 8,166,164.

(Continued)

(51) Int. Cl.
*G06F 15/16* (2006.01)
*G06F 15/173* (2006.01)
(Continued)

(52) U.S. Cl.
CPC .......... *A61B 3/10* (2013.01); *A61B 3/1005* (2013.01); *A61B 5/1076* (2013.01); *A61F 2/1694* (2013.01); *G01B 3/563* (2013.01); *A61B 3/117* (2013.01)

USPC ............ 709/224; 709/203; 709/217; 709/229

(58) Field of Classification Search
USPC ......... 709/203, 217, 219, 223, 224, 229, 246; 718/1
See application file for complete search history.

(56) References Cited

U.S. PATENT DOCUMENTS

| 222,458 A | 12/1879 | Connolly et al. |
| 447,918 A | 3/1891 | Strowger |

(Continued)

FOREIGN PATENT DOCUMENTS

| EP | 0772327 A2 | 5/1997 |
| EP | 1278390 A1 | 1/2003 |

(Continued)

OTHER PUBLICATIONS

Allchin, James Edward, "An Architecture For Reliable Decentralized Systems," Ph.D. Thesis, Georgia Institute of Technology, 185 pages, Sep. 1983.

(Continued)

*Primary Examiner* — Quang N Nguyen
(74) *Attorney, Agent, or Firm* — NKK Patent Law, PLLC

(57) ABSTRACT

Systems and methods for application and network-based long poll request detection and cacheability assessment therefore are disclosed. In one aspect, embodiments of the present disclosure include a method, which may be implemented on a distributed proxy and cache system, including, determining relative timings between a first request initiated by the application, a response received responsive to the first request, and a second request initiated subsequent to the first request also by the application. The relative timings can be compared to request-response timing characteristics for other applications to determine whether the requests of the application are long poll requests.

22 Claims, 24 Drawing Sheets

Related U.S. Application Data

(60) Provisional application No. 61/533,021, filed on Sep. 9, 2011, provisional application No. 61/533,007, filed on Sep. 9, 2011, provisional application No. 61/532,857, filed on Sep. 9, 2011, provisional application No. 61/430,828, filed on Jan. 7, 2011, provisional application No. 61/416,033, filed on Nov. 22, 2010, provisional application No. 61/416,020, filed on Nov. 22, 2010, provisional application No. 61/408,820, filed on Nov. 1, 2010, provisional application No. 61/408,826, filed on Nov. 1, 2010, provisional application No. 61/408,854, filed on Nov. 1, 2010, provisional application No. 61/408,846, filed on Nov. 1, 2010, provisional application No. 61/408,829, filed on Nov. 1, 2010, provisional application No. 61/408,839, filed on Nov. 1, 2010, provisional application No. 61/408,858, filed on Nov. 1, 2010.

(51) Int. Cl.
*A61B 3/10* (2006.01)
*A61B 5/107* (2006.01)
*A61F 2/16* (2006.01)
*G01B 3/56* (2006.01)
*A61B 3/117* (2006.01)

(56) References Cited

U.S. PATENT DOCUMENTS

| | | |
|---|---|---|
| 4,200,770 A | 4/1980 | Hellman et al. |
| 4,255,796 A | 3/1981 | Gabbe et al. |
| 4,276,597 A | 6/1981 | Dissly et al. |
| 4,531,020 A | 7/1985 | Wechselberger et al. |
| 4,807,182 A | 2/1989 | Queen |
| 4,831,582 A | 5/1989 | Miller et al. |
| 4,875,159 A | 10/1989 | Cary et al. |
| 4,897,781 A | 1/1990 | Chang et al. |
| 4,972,457 A | 11/1990 | O'Sullivan |
| 5,008,853 A | 4/1991 | Bly et al. |
| 5,159,624 A | 10/1992 | Makita |
| 5,220,657 A | 6/1993 | Bly et al. |
| 5,263,157 A | 11/1993 | Janis |
| 5,283,856 A | 2/1994 | Gross et al. |
| 5,357,431 A | 10/1994 | Nakada et al. |
| 5,384,892 A | 1/1995 | Strong |
| 5,386,564 A | 1/1995 | Shearer et al. |
| 5,392,390 A | 2/1995 | Crozier |
| 5,434,994 A | 7/1995 | Shaheen et al. |
| 5,436,960 A | 7/1995 | Campana, Jr. et al. |
| 5,438,611 A | 8/1995 | Campana, Jr. et al. |
| 5,479,472 A | 12/1995 | Campana, Jr. et al. |
| 5,487,100 A | 1/1996 | Kane |
| 5,491,703 A | 2/1996 | Barnaby et al. |
| 5,493,692 A | 2/1996 | Theimer et al. |
| 5,519,606 A | 5/1996 | Frid-Nielsen et al. |
| 5,555,376 A | 9/1996 | Theimer et al. |
| 5,559,800 A | 9/1996 | Mousseau et al. |
| 5,572,571 A | 11/1996 | Shirai |
| 5,572,643 A | 11/1996 | Judson |
| 5,574,859 A | 11/1996 | Yeh |
| 5,581,749 A | 12/1996 | Hossain et al. |
| 5,600,834 A | 2/1997 | Howard |
| 5,603,054 A | 2/1997 | Theimer et al. |
| 5,604,788 A | 2/1997 | Tett |
| 5,613,012 A | 3/1997 | Hoffman et al. |
| 5,619,507 A | 4/1997 | Tsuda |
| 5,619,648 A | 4/1997 | Canale et al. |
| 5,623,601 A | 4/1997 | Vu |
| 5,625,670 A | 4/1997 | Campana, Jr. et al. |
| 5,625,815 A | 4/1997 | Maier et al. |
| 5,627,658 A | 5/1997 | Connors et al. |
| 5,630,081 A | 5/1997 | Rybicki et al. |
| 5,631,946 A | 5/1997 | Campana, Jr. et al. |
| 5,632,018 A | 5/1997 | Otorii |
| 5,634,053 A | 5/1997 | Noble et al. |
| 5,647,002 A | 7/1997 | Brunson |
| 5,652,884 A | 7/1997 | Palevich |
| 5,664,207 A | 9/1997 | Crumpler et al. |
| 5,666,530 A | 9/1997 | Clark et al. |
| 5,666,553 A | 9/1997 | Crozier |
| 5,680,542 A | 10/1997 | Mulchandani et al. |
| 5,682,524 A | 10/1997 | Freund et al. |
| 5,684,990 A | 11/1997 | Boothby |
| 5,689,654 A | 11/1997 | Kikinis et al. |
| 5,692,039 A | 11/1997 | Brankley et al. |
| 5,696,903 A | 12/1997 | Mahany |
| 5,701,423 A | 12/1997 | Crozier |
| 5,701,469 A | 12/1997 | Brandli et al. |
| 5,704,029 A | 12/1997 | Wright, Jr. |
| 5,706,211 A | 1/1998 | Beletic et al. |
| 5,706,502 A | 1/1998 | Foley et al. |
| 5,706,507 A | 1/1998 | Schloss |
| 5,710,918 A | 1/1998 | Lagarde et al. |
| 5,713,019 A | 1/1998 | Keaten |
| 5,715,403 A | 2/1998 | Stefik |
| 5,717,925 A | 2/1998 | Harper et al. |
| 5,721,908 A | 2/1998 | Lagarde et al. |
| 5,721,914 A | 2/1998 | DeVries |
| 5,727,202 A | 3/1998 | Kucala |
| 5,729,549 A | 3/1998 | Kostreski et al. |
| 5,729,704 A | 3/1998 | Stone et al. |
| 5,729,735 A | 3/1998 | Meyering |
| 5,742,905 A | 4/1998 | Pepe et al. |
| 5,745,360 A | 4/1998 | Leone et al. |
| 5,752,186 A | 5/1998 | Malackowski et al. |
| 5,752,246 A | 5/1998 | Rogers et al. |
| 5,754,938 A | 5/1998 | Herz et al. |
| 5,757,916 A | 5/1998 | MacDoran et al. |
| 5,758,088 A | 5/1998 | Bezaire et al. |
| 5,758,150 A | 5/1998 | Bell et al. |
| 5,758,322 A | 5/1998 | Rongley |
| 5,758,354 A | 5/1998 | Huang et al. |
| 5,758,355 A | 5/1998 | Buchanan |
| 5,765,171 A | 6/1998 | Gehani et al. |
| 5,778,346 A | 7/1998 | Frid-Nielsen et al. |
| 5,778,361 A | 7/1998 | Nanjo et al. |
| 5,781,614 A | 7/1998 | Brunson |
| 5,781,901 A | 7/1998 | Kuzma |
| 5,781,906 A | 7/1998 | Aggarwal et al. |
| 5,787,430 A | 7/1998 | Doeringer et al. |
| 5,787,441 A | 7/1998 | Beckhardt |
| 5,790,425 A | 8/1998 | Wagle |
| 5,790,790 A | 8/1998 | Smith et al. |
| 5,790,974 A | 8/1998 | Tognazzini |
| 5,793,413 A | 8/1998 | Hylton et al. |
| 5,794,210 A | 8/1998 | Goldhaber et al. |
| 5,799,318 A | 8/1998 | Cardinal et al. |
| 5,802,312 A | 9/1998 | Lazaridis et al. |
| 5,802,454 A | 9/1998 | Goshay et al. |
| 5,802,518 A | 9/1998 | Karaev et al. |
| 5,802,524 A | 9/1998 | Flowers et al. |
| 5,806,074 A | 9/1998 | Souder et al. |
| 5,809,242 A | 9/1998 | Shaw et al. |
| 5,809,415 A | 9/1998 | Rossmann |
| 5,818,437 A | 10/1998 | Grover et al. |
| 5,819,172 A | 10/1998 | Campana, Jr. et al. |
| 5,819,274 A | 10/1998 | Jackson, Jr. |
| 5,819,284 A | 10/1998 | Farber et al. |
| 5,822,324 A | 10/1998 | Kostresti et al. |
| 5,822,747 A | 10/1998 | Graefe et al. |
| 5,826,269 A | 10/1998 | Hussey |
| 5,831,664 A | 11/1998 | Wharton et al. |
| 5,832,483 A | 11/1998 | Barker |
| 5,832,489 A | 11/1998 | Kucala |
| 5,832,500 A | 11/1998 | Burrows |
| 5,835,087 A | 11/1998 | Herz et al. |
| 5,835,722 A | 11/1998 | Bradshaw et al. |
| 5,838,252 A | 11/1998 | Kikinis |
| 5,838,768 A | 11/1998 | Sumar et al. |
| 5,838,973 A | 11/1998 | Carpenter-Smith et al. |
| 5,845,278 A | 12/1998 | Kirsch et al. |
| 5,852,775 A | 12/1998 | Hidary |

(56) References Cited

U.S. PATENT DOCUMENTS

| | | |
|---|---|---|
| 5,852,820 A | 12/1998 | Burrows |
| 5,857,201 A | 1/1999 | Wright, Jr. et al. |
| 5,862,223 A | 1/1999 | Walker et al. |
| 5,867,665 A | 2/1999 | Butman et al. |
| 5,867,817 A | 2/1999 | Catallo et al. |
| 5,870,759 A | 2/1999 | Bauer et al. |
| 5,884,323 A | 3/1999 | Hawkins et al. |
| 5,889,845 A | 3/1999 | Staples et al. |
| 5,890,147 A | 3/1999 | Peltonen et al. |
| 5,892,909 A | 4/1999 | Grasso et al. |
| 5,898,780 A | 4/1999 | Liu et al. |
| 5,898,917 A | 4/1999 | Batni et al. |
| 5,903,723 A | 5/1999 | Beck et al. |
| 5,907,618 A | 5/1999 | Gennaro et al. |
| 5,909,689 A | 6/1999 | Van Ryzin |
| 5,913,032 A | 6/1999 | Schwartz et al. |
| 5,924,096 A | 7/1999 | Draper et al. |
| 5,928,325 A | 7/1999 | Shaughnessy et al. |
| 5,928,329 A | 7/1999 | Clark et al. |
| 5,937,161 A | 8/1999 | Mulligan et al. |
| 5,940,813 A | 8/1999 | Hutchings |
| 5,943,676 A | 8/1999 | Boothby |
| 5,948,066 A | 9/1999 | Whalen et al. |
| 5,951,636 A | 9/1999 | Zerber |
| 5,960,394 A | 9/1999 | Gould et al. |
| 5,960,406 A | 9/1999 | Rasansky et al. |
| 5,961,590 A | 10/1999 | Mendez et al. |
| 5,963,642 A | 10/1999 | Goldstein |
| 5,964,833 A | 10/1999 | Kikinis |
| 5,968,131 A | 10/1999 | Mendez et al. |
| 5,974,238 A | 10/1999 | Chase, Jr. |
| 5,974,327 A | 10/1999 | Agrawal et al. |
| 5,978,837 A | 11/1999 | Foladare et al. |
| 5,978,933 A | 11/1999 | Wyld et al. |
| 5,987,440 A | 11/1999 | O'Neil et al. |
| 6,000,000 A | 12/1999 | Hawkins et al. |
| 6,003,070 A | 12/1999 | Frantz |
| 6,006,274 A | 12/1999 | Hawkins et al. |
| 6,016,478 A | 1/2000 | Zhang et al. |
| 6,016,520 A | 1/2000 | Facq et al. |
| 6,018,762 A | 1/2000 | Brunson et al. |
| 6,023,700 A | 2/2000 | Owens et al. |
| 6,023,708 A | 2/2000 | Mendez et al. |
| 6,029,238 A | 2/2000 | Furukawa |
| 6,034,621 A | 3/2000 | Kaufman |
| 6,035,104 A | 3/2000 | Zahariev |
| 6,044,372 A | 3/2000 | Rothfus et al. |
| 6,044,381 A | 3/2000 | Boothby et al. |
| 6,047,051 A | 4/2000 | Ginzboorg et al. |
| 6,047,327 A | 4/2000 | Tso et al. |
| 6,052,563 A | 4/2000 | Macko |
| 6,052,735 A | 4/2000 | Ulrich et al. |
| 6,057,855 A | 5/2000 | Barkans |
| 6,065,055 A | 5/2000 | Hughes et al. |
| 6,073,138 A | 6/2000 | de l'Etraz et al. |
| 6,073,142 A | 6/2000 | Geiger et al. |
| 6,073,165 A | 6/2000 | Narasimhan et al. |
| 6,085,166 A | 7/2000 | Beckhardt et al. |
| 6,085,192 A | 7/2000 | Mendez et al. |
| 6,088,677 A | 7/2000 | Spurgeon |
| 6,101,320 A | 8/2000 | Schuetze et al. |
| 6,101,480 A | 8/2000 | Conmy et al. |
| 6,101,531 A | 8/2000 | Eggleston et al. |
| 6,112,181 A | 8/2000 | Shear et al. |
| 6,119,014 A | 9/2000 | Alperovich et al. |
| 6,119,171 A | 9/2000 | Alkhatib |
| 6,125,369 A | 9/2000 | Wu et al. |
| 6,125,388 A | 9/2000 | Reisman |
| 6,128,627 A | 10/2000 | Mattis et al. |
| 6,130,898 A | 10/2000 | Kostreski et al. |
| 6,131,096 A | 10/2000 | Ng et al. |
| 6,131,116 A | 10/2000 | Riggins et al. |
| 6,134,432 A | 10/2000 | Holmes et al. |
| 6,138,013 A | 10/2000 | Blanchard et al. |
| 6,138,124 A | 10/2000 | Beckhardt |
| 6,138,128 A | 10/2000 | Perkowitz et al. |
| 6,138,146 A | 10/2000 | Moon et al. |
| 6,141,664 A | 10/2000 | Boothby |
| 6,151,606 A | 11/2000 | Mendez |
| 6,157,630 A | 12/2000 | Adler et al. |
| 6,161,140 A | 12/2000 | Moriya |
| 6,167,379 A | 12/2000 | Dean et al. |
| 6,167,435 A | 12/2000 | Druckenmiller et al. |
| 6,170,014 B1 | 1/2001 | Darago et al. |
| 6,173,312 B1 | 1/2001 | Atarashi et al. |
| 6,173,446 B1 | 1/2001 | Khan et al. |
| 6,175,831 B1 | 1/2001 | Weinreich et al. |
| 6,178,419 B1 | 1/2001 | Legh-Smith et al. |
| 6,181,935 B1 | 1/2001 | Gossman et al. |
| 6,185,184 B1 | 2/2001 | Mattaway et al. |
| 6,195,533 B1 | 2/2001 | Tkatch et al. |
| 6,198,696 B1 | 3/2001 | Korpi et al. |
| 6,198,922 B1 | 3/2001 | Baynham |
| 6,201,469 B1 | 3/2001 | Balch et al. |
| 6,202,085 B1 | 3/2001 | Benson et al. |
| 6,205,448 B1 | 3/2001 | Kruglikov et al. |
| 6,212,529 B1 | 4/2001 | Boothby et al. |
| 6,219,694 B1 | 4/2001 | Lazaridis et al. |
| 6,221,877 B1 | 4/2001 | Aronov et al. |
| 6,223,187 B1 | 4/2001 | Boothby et al. |
| 6,226,686 B1 | 5/2001 | Rothschild et al. |
| 6,233,341 B1 | 5/2001 | Riggins |
| 6,243,705 B1 | 6/2001 | Kucala |
| 6,246,875 B1 | 6/2001 | Seazholtz et al. |
| 6,247,135 B1 | 6/2001 | Feague |
| 6,249,808 B1 | 6/2001 | Seshadri |
| 6,256,666 B1 | 7/2001 | Singhal |
| 6,263,201 B1 | 7/2001 | Hashimoto et al. |
| 6,263,340 B1 | 7/2001 | Green |
| 6,269,369 B1 | 7/2001 | Robertson |
| 6,272,545 B1 | 8/2001 | Flanagin et al. |
| 6,275,850 B1 | 8/2001 | Beyda et al. |
| 6,275,858 B1 | 8/2001 | Bates et al. |
| 6,289,212 B1 | 9/2001 | Stein et al. |
| 6,289,214 B1 | 9/2001 | Backstrom |
| 6,292,904 B1 | 9/2001 | Broomhall et al. |
| 6,295,541 B1 | 9/2001 | Bodnar et al. |
| 6,300,947 B1 | 10/2001 | Kanevsky |
| 6,304,881 B1 | 10/2001 | Halim et al. |
| 6,308,201 B1 | 10/2001 | Pivowar et al. |
| 6,317,594 B1 | 11/2001 | Gossman et al. |
| 6,320,943 B1 | 11/2001 | Borland |
| 6,324,541 B1 | 11/2001 | de l'Etraz et al. |
| 6,324,542 B1 | 11/2001 | Wright, Jr. et al. |
| 6,324,544 B1 | 11/2001 | Alam et al. |
| 6,324,587 B1 | 11/2001 | Trenbeath et al. |
| 6,327,586 B1 | 12/2001 | Kisiel |
| 6,336,117 B1 | 1/2002 | Massarani |
| 6,336,138 B1 | 1/2002 | Caswell et al. |
| 6,351,767 B1 | 2/2002 | Batchelder et al. |
| 6,356,937 B1 | 3/2002 | Montville et al. |
| 6,363,051 B1 | 3/2002 | Eslambolchi et al. |
| 6,363,352 B1 | 3/2002 | Dailey et al. |
| 6,370,566 B2 | 4/2002 | Discolo et al. |
| 6,377,810 B1 | 4/2002 | Geiger et al. |
| 6,380,959 B1 | 4/2002 | Wang et al. |
| 6,389,422 B1 | 5/2002 | Doi et al. |
| 6,389,455 B1 | 5/2002 | Fuisz |
| 6,389,457 B2 | 5/2002 | Lazaridis et al. |
| 6,397,057 B1 | 5/2002 | Malackowski et al. |
| 6,397,230 B1 | 5/2002 | Carmel et al. |
| 6,401,104 B1 | 6/2002 | LaRue et al. |
| 6,401,112 B1 | 6/2002 | Boyer et al. |
| 6,401,113 B2 | 6/2002 | Lazaridis et al. |
| 6,405,197 B2 | 6/2002 | Gilmour |
| 6,411,696 B1 | 6/2002 | Iverson et al. |
| 6,415,031 B1 | 7/2002 | Colligan et al. |
| 6,418,308 B1 | 7/2002 | Heinonen et al. |
| 6,421,669 B1 | 7/2002 | Gilmour et al. |
| 6,421,781 B1 | 7/2002 | Fox et al. |
| 6,430,602 B1 | 8/2002 | Kay et al. |
| 6,438,585 B2 | 8/2002 | Mousseau et al. |
| 6,438,612 B1 | 8/2002 | Ylonen et al. |
| 6,442,589 B1 | 8/2002 | Takahashi et al. |

(56) References Cited

U.S. PATENT DOCUMENTS

| | | |
|---|---|---|
| 6,442,637 B1 | 8/2002 | Hawkins et al. |
| 6,446,118 B1 | 9/2002 | Gottlieb |
| 6,463,463 B1 | 10/2002 | Godfrey et al. |
| 6,463,464 B1 | 10/2002 | Lazaridis et al. |
| 6,487,557 B1 | 11/2002 | Nagatomo |
| 6,487,560 B1 | 11/2002 | LaRue et al. |
| 6,490,353 B1 | 12/2002 | Tan |
| 6,496,802 B1 | 12/2002 | van Zoest et al. |
| 6,499,054 B1 | 12/2002 | Hesselink et al. |
| 6,505,214 B1 | 1/2003 | Sherman et al. |
| 6,516,327 B1 | 2/2003 | Zondervan et al. |
| 6,526,433 B1 | 2/2003 | Chang et al. |
| 6,526,506 B1 | 2/2003 | Lewis |
| 6,529,908 B1 | 3/2003 | Piett et al. |
| 6,532,446 B1 | 3/2003 | King |
| 6,535,892 B1 | 3/2003 | LaRue et al. |
| 6,546,005 B1 | 4/2003 | Berkley et al. |
| 6,549,939 B1 | 4/2003 | Ford et al. |
| 6,556,217 B1 | 4/2003 | Mäkipää et al. |
| 6,593,944 B1 | 7/2003 | Nicolas et al. |
| 6,601,026 B2 | 7/2003 | Appelt et al. |
| 6,615,253 B1 | 9/2003 | Bowman-Amuah |
| 6,618,710 B1 | 9/2003 | Zondervan et al. |
| 6,621,892 B1 | 9/2003 | Banister et al. |
| 6,625,621 B2 | 9/2003 | Tan et al. |
| 6,636,482 B2 | 10/2003 | Cloonan et al. |
| 6,639,693 B1 | 10/2003 | Ejiri et al. |
| 6,640,097 B2 | 10/2003 | Corrigan et al. |
| 6,640,244 B1 | 10/2003 | Bowman-Amuah |
| 6,640,249 B1 | 10/2003 | Bowman-Amuah |
| 6,643,650 B1 | 11/2003 | Slaughter et al. |
| 6,643,688 B1 | 11/2003 | Fuisz |
| 6,647,384 B2 | 11/2003 | Gilmour |
| 6,650,890 B1 | 11/2003 | Irlam et al. |
| 6,662,016 B1 | 12/2003 | Buckham et al. |
| 6,668,046 B1 | 12/2003 | Albal |
| 6,671,695 B2 | 12/2003 | McFadden |
| 6,671,700 B1 | 12/2003 | Creemer et al. |
| 6,671,702 B2 | 12/2003 | Kruglikov et al. |
| 6,671,757 B1 | 12/2003 | Multer et al. |
| 6,694,336 B1 | 2/2004 | Multer et al. |
| 6,697,807 B2 | 2/2004 | McGeachie |
| 6,701,378 B1 | 3/2004 | Gilhuly et al. |
| 6,707,801 B2 | 3/2004 | Hsu |
| 6,708,221 B1 | 3/2004 | Mendez et al. |
| 6,714,965 B2 | 3/2004 | Kakuta et al. |
| 6,721,787 B1 | 4/2004 | Hiscock |
| 6,727,917 B1 | 4/2004 | Chew et al. |
| 6,728,530 B1 | 4/2004 | Heinonen et al. |
| 6,728,786 B2 | 4/2004 | Hawkins et al. |
| 6,732,101 B1 | 5/2004 | Cook |
| 6,732,158 B1 | 5/2004 | Hesselink et al. |
| 6,735,591 B2 | 5/2004 | Khan |
| 6,741,232 B1 | 5/2004 | Siedlikowski et al. |
| 6,741,855 B1 | 5/2004 | Martin et al. |
| 6,742,015 B1 | 5/2004 | Bowman-Amuah |
| 6,742,059 B1 | 5/2004 | Todd et al. |
| 6,745,024 B1 | 6/2004 | DeJaco et al. |
| 6,745,326 B1 | 6/2004 | Wary |
| 6,756,882 B2 | 6/2004 | Benes et al. |
| 6,757,362 B1 | 6/2004 | Cooper et al. |
| 6,757,696 B2 | 6/2004 | Multer et al. |
| 6,757,708 B1 | 6/2004 | Craig et al. |
| 6,760,916 B2 | 7/2004 | Holtz et al. |
| 6,771,294 B1 | 8/2004 | Pulli et al. |
| 6,775,362 B1 | 8/2004 | Ransom |
| 6,779,019 B1 | 8/2004 | Mousseau et al. |
| 6,782,409 B1 | 8/2004 | Yoshida |
| 6,785,868 B1 | 8/2004 | Raff |
| 6,785,906 B1 | 8/2004 | Gaughan et al. |
| 6,799,190 B1 | 9/2004 | Boothby |
| 6,804,707 B1 | 10/2004 | Ronning |
| 6,816,849 B1 | 11/2004 | Halt, Jr. |
| 6,820,088 B1 | 11/2004 | Hind et al. |
| 6,820,204 B1 | 11/2004 | Desai et al. |
| 6,829,487 B2 | 12/2004 | Eiden et al. |
| 6,834,195 B2 | 12/2004 | Brandenberg et al. |
| 6,847,974 B2 | 1/2005 | Wachtel |
| 6,850,757 B2 | 2/2005 | Watanabe et al. |
| 6,859,212 B2 | 2/2005 | Kumar et al. |
| 6,867,774 B1 | 3/2005 | Halmshaw et al. |
| 6,868,447 B1 | 3/2005 | Slaughter et al. |
| 6,871,220 B1 | 3/2005 | Rajan et al. |
| 6,871,236 B2 | 3/2005 | Fishman et al. |
| 6,873,688 B1 | 3/2005 | Aarnio |
| 6,874,017 B1 | 3/2005 | Inoue et al. |
| 6,879,985 B2 | 4/2005 | Deguchi et al. |
| 6,886,030 B1 | 4/2005 | Easterbrook et al. |
| 6,892,070 B2 | 5/2005 | Warrier et al. |
| 6,892,196 B1 | 5/2005 | Hughes |
| 6,895,394 B1 | 5/2005 | Kremer et al. |
| 6,895,558 B1 | 5/2005 | Loveland |
| 6,898,427 B1 | 5/2005 | Griffith et al. |
| 6,922,547 B2 | 7/2005 | O'Neill et al. |
| 6,922,721 B1 | 7/2005 | Minborg et al. |
| 6,925,477 B1 | 8/2005 | Champagne et al. |
| 6,931,529 B2 | 8/2005 | Kunzinger |
| 6,938,079 B1 | 8/2005 | Anderson et al. |
| 6,944,447 B2 | 9/2005 | Portman et al. |
| 6,944,662 B2 | 9/2005 | Devine et al. |
| 6,947,770 B2 | 9/2005 | Rydbeck |
| 6,957,397 B1 | 10/2005 | Hawkins et al. |
| 6,965,917 B1 | 11/2005 | Aloni et al. |
| 6,966,058 B2 | 11/2005 | Earl et al. |
| 6,968,175 B2 | 11/2005 | Raivisto et al. |
| 6,970,879 B1 | 11/2005 | Gilmour |
| 6,972,682 B2 | 12/2005 | Lareau et al. |
| 6,973,299 B2 | 12/2005 | Apfel |
| 6,981,041 B2 | 12/2005 | Araujo et al. |
| 6,981,047 B2 | 12/2005 | Hanson et al. |
| 6,985,933 B1 | 1/2006 | Singhal et al. |
| 6,985,983 B2 | 1/2006 | Pellegrino et al. |
| 6,986,061 B1 | 1/2006 | Kunzinger |
| 6,987,734 B2 | 1/2006 | Hundemer |
| 6,990,472 B2 | 1/2006 | Rosenhaft et al. |
| 6,993,326 B2 | 1/2006 | Link, II et al. |
| 6,993,327 B2 | 1/2006 | Mathis |
| 6,996,627 B1 | 2/2006 | Carden |
| 6,999,753 B2 | 2/2006 | Beckmann et al. |
| 7,020,685 B1 | 3/2006 | Chen et al. |
| 7,024,491 B1 | 4/2006 | Hanmann et al. |
| 7,026,984 B1 | 4/2006 | Thandu et al. |
| 7,032,242 B1 | 4/2006 | Grabelsky et al. |
| 7,035,630 B2 | 4/2006 | Knowles |
| 7,046,993 B2 | 5/2006 | Haaramo et al. |
| 7,047,202 B2 | 5/2006 | Jaipuria et al. |
| 7,062,024 B2 | 6/2006 | Kreckel et al. |
| 7,069,308 B2 | 6/2006 | Abrams |
| 7,072,678 B2 | 7/2006 | Allison |
| 7,079,499 B1 | 7/2006 | Akhtar et al. |
| 7,080,371 B1 | 7/2006 | Arnaiz et al. |
| 7,082,316 B2 | 7/2006 | Eiden et al. |
| 7,085,365 B2 | 8/2006 | Kauppinen |
| 7,096,030 B2 | 8/2006 | Huomo |
| 7,100,821 B2 | 9/2006 | Rasti |
| 7,103,432 B2 | 9/2006 | Drader et al. |
| 7,120,692 B2 | 10/2006 | Hesselink et al. |
| 7,120,928 B2 | 10/2006 | Sheth et al. |
| 7,130,839 B2 | 10/2006 | Boreham et al. |
| 7,136,645 B2 | 11/2006 | Hanson et al. |
| 7,139,555 B2 | 11/2006 | Apfel |
| 7,139,565 B2 | 11/2006 | Fiatal et al. |
| 7,140,549 B2 | 11/2006 | de Jong |
| 7,146,645 B1 | 12/2006 | Hellsten et al. |
| 7,149,780 B2 | 12/2006 | Quine et al. |
| 7,149,789 B2 | 12/2006 | Slivka et al. |
| 7,149,959 B1 | 12/2006 | Jones et al. |
| 7,162,241 B2 | 1/2007 | Kim et al. |
| 7,165,727 B2 | 1/2007 | de Jong |
| 7,172,118 B2 | 2/2007 | Urken |
| 7,181,228 B2 | 2/2007 | Boesch |
| 7,184,790 B2 | 2/2007 | Dorenbosch et al. |
| 7,185,362 B2 | 2/2007 | Hawkes et al. |
| 7,194,273 B2 | 3/2007 | Vaudreuil |

(56) References Cited

U.S. PATENT DOCUMENTS

| | | |
|---|---|---|
| 7,200,390 B1 | 4/2007 | Henager et al. |
| 7,203,733 B1 | 4/2007 | Bern |
| 7,206,806 B2 | 4/2007 | Pineau |
| 7,209,757 B2 | 4/2007 | Naghian et al. |
| 7,210,121 B2 | 4/2007 | Xia et al. |
| 7,219,139 B2 | 5/2007 | Martin et al. |
| 7,219,222 B1 | 5/2007 | Durbin et al. |
| 7,224,957 B2 | 5/2007 | Spector |
| 7,231,206 B2 | 6/2007 | Cudak et al. |
| 7,233,795 B1 | 6/2007 | Ryden |
| 7,234,111 B2 | 6/2007 | Chu et al. |
| 7,239,877 B2 | 7/2007 | Corneille et al. |
| 7,240,095 B1 | 7/2007 | Lewis |
| 7,242,680 B2 | 7/2007 | Gallant |
| 7,245,926 B2 | 7/2007 | Liao et al. |
| 7,257,391 B2 | 8/2007 | Burgess et al. |
| 7,257,639 B1 | 8/2007 | Li et al. |
| 7,259,666 B1 | 8/2007 | Hermsmeyer et al. |
| 7,260,552 B2 | 8/2007 | Riera Jorba et al. |
| 7,260,590 B1 | 8/2007 | Williams |
| 7,260,651 B2 | 8/2007 | Parrella, Sr. et al. |
| 7,272,830 B2 | 9/2007 | de Jong |
| 7,277,408 B2 | 10/2007 | Sorsa |
| 7,284,664 B1 | 10/2007 | Ivchenko et al. |
| 7,289,792 B1 | 10/2007 | Turunen |
| 7,289,964 B1 | 10/2007 | Bowman-Amuah |
| 7,289,971 B1 | 10/2007 | O'Neil et al. |
| 7,293,107 B1 | 11/2007 | Hanson et al. |
| 7,295,853 B2 | 11/2007 | Jin et al. |
| 7,296,155 B1 | 11/2007 | Trostle et al. |
| 7,305,252 B2 | 12/2007 | Britt et al. |
| 7,305,700 B2 | 12/2007 | Boynton et al. |
| 7,310,350 B1 | 12/2007 | Shao et al. |
| 7,310,729 B2 | 12/2007 | Gordon et al. |
| 7,324,473 B2 | 1/2008 | Corneille et al. |
| 7,349,871 B2 | 3/2008 | Labrou et al. |
| 7,353,274 B1 | 4/2008 | Rouhi et al. |
| 7,359,720 B2 | 4/2008 | Hartmaier et al. |
| 7,373,386 B2 | 5/2008 | Gardner et al. |
| 7,374,099 B2 | 5/2008 | de Jong |
| 7,376,701 B2 | 5/2008 | Bhargava et al. |
| 7,382,879 B1 | 6/2008 | Miller |
| 7,388,950 B2 | 6/2008 | Elsey et al. |
| 7,389,412 B2 | 6/2008 | Sharma et al. |
| 7,392,483 B2 | 6/2008 | Wong et al. |
| 7,395,329 B1 | 7/2008 | Holt et al. |
| 7,398,271 B1 | 7/2008 | Borkovsky et al. |
| 7,430,609 B2 | 9/2008 | Brown et al. |
| 7,441,271 B2 | 10/2008 | Fiatal et al. |
| 7,443,847 B1 | 10/2008 | Albert et al. |
| 7,461,071 B2 | 12/2008 | Fitzpatrick et al. |
| 7,465,231 B2 | 12/2008 | Lewin et al. |
| 7,469,125 B2 | 12/2008 | Nurmi |
| 7,483,036 B2 | 1/2009 | Moore |
| 7,499,537 B2 | 3/2009 | Elsey et al. |
| 7,502,615 B2 | 3/2009 | Wilhoite et al. |
| 7,519,042 B2 | 4/2009 | Gorday et al. |
| 7,532,571 B1 | 5/2009 | Price et al. |
| 7,539,665 B2 | 5/2009 | Mendez |
| 7,548,947 B2 | 6/2009 | Kasriel et al. |
| 7,548,969 B2 | 6/2009 | Tripp et al. |
| 7,551,900 B2 | 6/2009 | Kang et al. |
| 7,567,575 B2 | 7/2009 | Chen et al. |
| 7,574,208 B2 | 8/2009 | Hanson et al. |
| 7,575,171 B2 | 8/2009 | Lev |
| 7,584,294 B2 | 9/2009 | Plamondon |
| 7,587,482 B2 | 9/2009 | Henderson et al. |
| 7,587,608 B2 | 9/2009 | Haller et al. |
| 7,593,714 B2 | 9/2009 | Schultz et al. |
| 7,596,608 B2 | 9/2009 | Alexander et al. |
| 7,596,791 B2 | 9/2009 | Wei et al. |
| 7,613,792 B2 | 11/2009 | Zervas et al. |
| 7,630,986 B1 | 12/2009 | Herz et al. |
| 7,634,558 B1 | 12/2009 | Mangal et al. |
| 7,643,818 B2 | 1/2010 | Backholm et al. |
| 7,644,166 B2 | 1/2010 | Appelman et al. |
| 7,650,416 B2 | 1/2010 | Wu et al. |
| 7,672,291 B2 | 3/2010 | Wang |
| 7,672,439 B2 | 3/2010 | Appelman et al. |
| 7,680,281 B2 | 3/2010 | Fiatal et al. |
| 7,684,346 B2 | 3/2010 | Valli |
| 7,689,664 B2 | 3/2010 | Karlberg |
| 7,693,555 B2 | 4/2010 | Srinivasan et al. |
| 7,693,944 B2 | 4/2010 | Appelman et al. |
| 7,694,008 B2 | 4/2010 | Chang et al. |
| 7,706,781 B2 | 4/2010 | Backholm et al. |
| 7,707,573 B1 | 4/2010 | Marmaros et al. |
| 7,752,633 B1 | 7/2010 | Fleming |
| 7,757,956 B2 | 7/2010 | Koenck et al. |
| 7,769,395 B2 | 8/2010 | Fiatal et al. |
| 7,769,400 B2 | 8/2010 | Backholm et al. |
| 7,769,805 B1 | 8/2010 | Barnes et al. |
| 7,778,792 B2 | 8/2010 | Huang et al. |
| 7,783,757 B2 | 8/2010 | Plamondon |
| 7,796,742 B1 | 9/2010 | Sutaria et al. |
| 7,797,064 B2 | 9/2010 | Loomis et al. |
| 7,809,818 B2 | 10/2010 | Plamondon |
| 7,827,055 B1 | 11/2010 | Snodgrass et al. |
| 7,827,597 B2 | 11/2010 | Boynton et al. |
| 7,853,563 B2 | 12/2010 | Alvarado et al. |
| 7,877,703 B1 | 1/2011 | Fleming |
| 7,881,745 B1 | 2/2011 | Rao et al. |
| 7,899,996 B1 | 3/2011 | Levin-Michael |
| 7,908,656 B1 | 3/2011 | Mu |
| 7,917,468 B2 | 3/2011 | Ariel et al. |
| 7,917,505 B2 | 3/2011 | van Gent et al. |
| 7,921,167 B2 | 4/2011 | Shroff et al. |
| 7,930,416 B2 | 4/2011 | Miller et al. |
| 7,933,929 B1 | 4/2011 | McClendon et al. |
| 7,937,091 B2 | 5/2011 | Roman et al. |
| 7,970,860 B2 | 6/2011 | Kline et al. |
| 7,996,487 B2 | 8/2011 | Snyder |
| 8,005,891 B2 | 8/2011 | Knowles et al. |
| 8,010,082 B2 | 8/2011 | Sutaria et al. |
| 8,032,409 B1 | 10/2011 | Mikurak |
| 8,064,583 B1 | 11/2011 | Sutaria et al. |
| 8,069,166 B2 | 11/2011 | Alvarado et al. |
| 8,078,158 B2 | 12/2011 | Backholm |
| 8,107,921 B2 | 1/2012 | Fiatal |
| 8,116,214 B2 | 2/2012 | Backholm et al. |
| 8,127,342 B2 | 2/2012 | Boynton et al. |
| 8,166,164 B1 | 4/2012 | Luna et al. |
| 8,190,701 B2 | 5/2012 | Luna et al. |
| 8,194,680 B1 | 6/2012 | Brandwine et al. |
| 8,204,953 B2 | 6/2012 | Luna et al. |
| 8,209,709 B2 | 6/2012 | Fleming |
| 8,260,852 B1 | 9/2012 | Cselle |
| 8,291,076 B2 | 10/2012 | Luna et al. |
| 8,634,809 B1 * | 1/2014 | Pfeffer .................. 709/246 |
| 2001/0009025 A1 | 7/2001 | Ahonen |
| 2001/0010046 A1 | 7/2001 | Muyres et al. |
| 2001/0013069 A1 | 8/2001 | Shah |
| 2001/0023414 A1 | 9/2001 | Kumar et al. |
| 2001/0032254 A1 | 10/2001 | Hawkins |
| 2001/0034225 A1 | 10/2001 | Gupte et al. |
| 2001/0034244 A1 | 10/2001 | Calder et al. |
| 2001/0037453 A1 | 11/2001 | Mitty et al. |
| 2001/0039191 A1 | 11/2001 | Maierhofer |
| 2001/0041566 A1 | 11/2001 | Xanthos et al. |
| 2001/0042009 A1 | 11/2001 | Montague |
| 2001/0042099 A1 | 11/2001 | Peng |
| 2001/0043148 A1 | 11/2001 | Stewart |
| 2001/0052052 A1 | 12/2001 | Peng |
| 2001/0053687 A1 | 12/2001 | Sivula |
| 2002/0002478 A1 | 1/2002 | Swart et al. |
| 2002/0002591 A1 | 1/2002 | Ketola |
| 2002/0007303 A1 | 1/2002 | Brookler et al. |
| 2002/0013727 A1 | 1/2002 | Lee |
| 2002/0019225 A1 | 2/2002 | Miyashita |
| 2002/0019812 A1 | 2/2002 | Board et al. |
| 2002/0035556 A1 | 3/2002 | Shah et al. |
| 2002/0035617 A1 | 3/2002 | Lynch et al. |
| 2002/0038253 A1 | 3/2002 | Seaman et al. |
| 2002/0042875 A1 | 4/2002 | Shukla |

(56) References Cited

U.S. PATENT DOCUMENTS

| | | |
|---|---|---|
| 2002/0049828 A1 | 4/2002 | Pekarek-Kostka |
| 2002/0053078 A1 | 5/2002 | Holtz et al. |
| 2002/0055351 A1 | 5/2002 | Elsey et al. |
| 2002/0059201 A1 | 5/2002 | Work |
| 2002/0059457 A1 | 5/2002 | Ballard et al. |
| 2002/0068559 A1 | 6/2002 | Sharma et al. |
| 2002/0073207 A1 | 6/2002 | Widger et al. |
| 2002/0077077 A1 | 6/2002 | Rezvani et al. |
| 2002/0077084 A1 | 6/2002 | Zellner et al. |
| 2002/0078384 A1 | 6/2002 | Hippelainen |
| 2002/0087549 A1 | 7/2002 | Mostafa |
| 2002/0087679 A1 | 7/2002 | Pulley et al. |
| 2002/0087883 A1 | 7/2002 | Wohlgemuth et al. |
| 2002/0089542 A1 | 7/2002 | Imamura |
| 2002/0091921 A1 | 7/2002 | Kunzinger |
| 2002/0095319 A1 | 7/2002 | Swart et al. |
| 2002/0095328 A1 | 7/2002 | Swart et al. |
| 2002/0095391 A1 | 7/2002 | Swart et al. |
| 2002/0095399 A1 | 7/2002 | Devine et al. |
| 2002/0098855 A1 | 7/2002 | Hartmaier et al. |
| 2002/0099613 A1 | 7/2002 | Swart et al. |
| 2002/0099809 A1 | 7/2002 | Lee |
| 2002/0101975 A1 | 8/2002 | Tiburtius et al. |
| 2002/0103934 A1 | 8/2002 | Fishman et al. |
| 2002/0107944 A1 | 8/2002 | Bai et al. |
| 2002/0107985 A1 | 8/2002 | Hwang et al. |
| 2002/0116499 A1 | 8/2002 | Ennus et al. |
| 2002/0116501 A1 | 8/2002 | Ho et al. |
| 2002/0120388 A1 | 8/2002 | Bullock |
| 2002/0120766 A1 | 8/2002 | Okajima et al. |
| 2002/0120779 A1 | 8/2002 | Teeple et al. |
| 2002/0126701 A1 | 9/2002 | Requena |
| 2002/0133504 A1 | 9/2002 | Vlahos et al. |
| 2002/0144109 A1 | 10/2002 | Benantar et al. |
| 2002/0146129 A1 | 10/2002 | Kaplan |
| 2002/0152379 A1 | 10/2002 | Gefwert et al. |
| 2002/0155848 A1 | 10/2002 | Suryanarayana |
| 2002/0156839 A1 | 10/2002 | Peterson et al. |
| 2002/0158908 A1 | 10/2002 | Vaajala et al. |
| 2002/0161587 A1 | 10/2002 | Pitts, III et al. |
| 2002/0161925 A1 | 10/2002 | Munger et al. |
| 2002/0161928 A1 | 10/2002 | Ndili |
| 2002/0164977 A1 | 11/2002 | Link, II et al. |
| 2002/0167484 A1 | 11/2002 | Hatanaka et al. |
| 2002/0174189 A1 | 11/2002 | Peng |
| 2002/0186848 A1 | 12/2002 | Shaik |
| 2002/0188940 A1 | 12/2002 | Breckner et al. |
| 2002/0193094 A1 | 12/2002 | Lawless et al. |
| 2002/0194209 A1 | 12/2002 | Bolosky et al. |
| 2002/0198027 A1 | 12/2002 | Rydbeck |
| 2003/0005151 A1 | 1/2003 | Ullman et al. |
| 2003/0014491 A1 | 1/2003 | Horvitz et al. |
| 2003/0022662 A1 | 1/2003 | Mittal |
| 2003/0023692 A1 | 1/2003 | Moroo |
| 2003/0023975 A1 | 1/2003 | Schrader et al. |
| 2003/0028430 A1 | 2/2003 | Zimmerman |
| 2003/0028441 A1 | 2/2003 | Barsness et al. |
| 2003/0046433 A1 | 3/2003 | Luzzatti et al. |
| 2003/0046586 A1 | 3/2003 | Bheemarasetti et al. |
| 2003/0046587 A1 | 3/2003 | Bheemarasetti et al. |
| 2003/0050041 A1 | 3/2003 | Wu |
| 2003/0051142 A1 | 3/2003 | Hidalgo et al. |
| 2003/0054810 A1 | 3/2003 | Chen et al. |
| 2003/0056096 A1 | 3/2003 | Albert et al. |
| 2003/0060188 A1 | 3/2003 | Gidron et al. |
| 2003/0063120 A1 | 4/2003 | Wong et al. |
| 2003/0065738 A1 | 4/2003 | Yang et al. |
| 2003/0065739 A1 | 4/2003 | Shnier |
| 2003/0065802 A1 | 4/2003 | Vitikainen et al. |
| 2003/0070061 A1 | 4/2003 | Wong et al. |
| 2003/0072451 A1 | 4/2003 | Pimentel et al. |
| 2003/0078880 A1 | 4/2003 | Alley et al. |
| 2003/0084165 A1 | 5/2003 | Kjellberg et al. |
| 2003/0088629 A1 | 5/2003 | Berkowitz et al. |
| 2003/0093691 A1 | 5/2003 | Simon et al. |
| 2003/0097381 A1 | 5/2003 | Detweiler et al. |
| 2003/0100321 A1 | 5/2003 | Rao et al. |
| 2003/0100326 A1 | 5/2003 | Grube et al. |
| 2003/0117432 A1 | 6/2003 | Kautto-Kiovula et al. |
| 2003/0120685 A1 | 6/2003 | Duncombe et al. |
| 2003/0125023 A1 | 7/2003 | Fishler |
| 2003/0126216 A1 | 7/2003 | Avila et al. |
| 2003/0130984 A1 | 7/2003 | Quinlan et al. |
| 2003/0145038 A1 | 7/2003 | Bin Tariq et al. |
| 2003/0146934 A1 | 8/2003 | Bailey et al. |
| 2003/0153338 A1 | 8/2003 | Herz et al. |
| 2003/0154212 A1 | 8/2003 | Schirmer et al. |
| 2003/0156146 A1 | 8/2003 | Suomela et al. |
| 2003/0157947 A1 | 8/2003 | Fiatal et al. |
| 2003/0169262 A1 | 9/2003 | Lavelle et al. |
| 2003/0177281 A1 | 9/2003 | McQuillan et al. |
| 2003/0182431 A1 | 9/2003 | Sturniolo et al. |
| 2003/0187984 A1 | 10/2003 | Banavar et al. |
| 2003/0204605 A1 | 10/2003 | Hudson et al. |
| 2003/0208529 A1 | 11/2003 | Pendyala et al. |
| 2003/0208559 A1 | 11/2003 | Velline et al. |
| 2003/0210666 A1 | 11/2003 | Trossen et al. |
| 2003/0211845 A1 | 11/2003 | Lohtia et al. |
| 2003/0217098 A1 | 11/2003 | Bobde et al. |
| 2003/0217142 A1 | 11/2003 | Bobde et al. |
| 2003/0223554 A1 | 12/2003 | Zhang |
| 2003/0227487 A1 | 12/2003 | Hugh |
| 2003/0227745 A1 | 12/2003 | Khoo |
| 2003/0235308 A1 | 12/2003 | Boynton et al. |
| 2003/0236857 A1 | 12/2003 | Takase et al. |
| 2003/0236981 A1 | 12/2003 | Marmigere et al. |
| 2004/0002324 A1 | 1/2004 | Juntunen et al. |
| 2004/0006630 A1 | 1/2004 | Friend et al. |
| 2004/0015504 A1 | 1/2004 | Ahad et al. |
| 2004/0024795 A1 | 2/2004 | Hind et al. |
| 2004/0024892 A1 | 2/2004 | Creswell et al. |
| 2004/0027326 A1 | 2/2004 | Hays et al. |
| 2004/0027375 A1 | 2/2004 | Ellis et al. |
| 2004/0027378 A1 | 2/2004 | Hays et al. |
| 2004/0043770 A1 | 3/2004 | Amit et al. |
| 2004/0049579 A1 | 3/2004 | Ims et al. |
| 2004/0049599 A1 | 3/2004 | Friend et al. |
| 2004/0051715 A1 | 3/2004 | Brokenshire et al. |
| 2004/0054739 A1 | 3/2004 | Friend et al. |
| 2004/0064445 A1 | 4/2004 | Pfleging et al. |
| 2004/0064488 A1 | 4/2004 | Sinha |
| 2004/0068579 A1 | 4/2004 | Marmigere et al. |
| 2004/0068698 A1 | 4/2004 | Wu et al. |
| 2004/0073476 A1 | 4/2004 | Donahue et al. |
| 2004/0073651 A1 | 4/2004 | Beaulieu et al. |
| 2004/0075675 A1 | 4/2004 | Raivisto et al. |
| 2004/0075695 A1 | 4/2004 | Chew et al. |
| 2004/0078814 A1 | 4/2004 | Allen |
| 2004/0080515 A1 | 4/2004 | Hagiwara |
| 2004/0082346 A1 | 4/2004 | Skytt et al. |
| 2004/0098625 A1 | 5/2004 | Lagadec et al. |
| 2004/0103147 A1 | 5/2004 | Flesher et al. |
| 2004/0107319 A1 | 6/2004 | D'Orto et al. |
| 2004/0110497 A1 | 6/2004 | Little |
| 2004/0120323 A1 | 6/2004 | Viikari et al. |
| 2004/0123095 A1 | 6/2004 | Marshall |
| 2004/0123304 A1 | 6/2004 | Black et al. |
| 2004/0127214 A1 | 7/2004 | Reddy et al. |
| 2004/0128375 A1 | 7/2004 | Rockwell |
| 2004/0133626 A1 | 7/2004 | Herrero et al. |
| 2004/0141011 A1 | 7/2004 | Smethers et al. |
| 2004/0147248 A1 | 7/2004 | Will |
| 2004/0147262 A1 | 7/2004 | Lescuyer et al. |
| 2004/0148375 A1 | 7/2004 | Levett et al. |
| 2004/0158611 A1 | 8/2004 | Daniell et al. |
| 2004/0167966 A1 | 8/2004 | Lee et al. |
| 2004/0170257 A1 | 9/2004 | Gross et al. |
| 2004/0172481 A1 | 9/2004 | Engstrom |
| 2004/0176128 A1 | 9/2004 | Grabelsky et al. |
| 2004/0177369 A1 | 9/2004 | Akins, III |
| 2004/0179513 A1 | 9/2004 | Smith et al. |
| 2004/0181550 A1 | 9/2004 | Warsta et al. |
| 2004/0184475 A1 | 9/2004 | Meier |
| 2004/0186902 A1 | 9/2004 | Stewart |

(56) References Cited

U.S. PATENT DOCUMENTS

| | | |
|---|---|---|
| 2004/0189610 A1 | 9/2004 | Friend |
| 2004/0199497 A1 | 10/2004 | Timmons |
| 2004/0199582 A1 | 10/2004 | Kucharewski et al. |
| 2004/0199663 A1 | 10/2004 | Horvitz et al. |
| 2004/0205248 A1 | 10/2004 | Little et al. |
| 2004/0205330 A1 | 10/2004 | Godfrey et al. |
| 2004/0209602 A1 | 10/2004 | Joyce et al. |
| 2004/0210639 A1 | 10/2004 | Ben-Yoseph et al. |
| 2004/0219940 A1 | 11/2004 | Kong et al. |
| 2004/0230619 A1 | 11/2004 | Blanco et al. |
| 2004/0233930 A1 | 11/2004 | Colby, Jr. |
| 2004/0236792 A1 | 11/2004 | Celik |
| 2004/0242209 A1 | 12/2004 | Kruis et al. |
| 2004/0252816 A1 | 12/2004 | Nicolas |
| 2004/0255126 A1 | 12/2004 | Reith |
| 2004/0258231 A1 | 12/2004 | Elsey et al. |
| 2004/0259535 A1 | 12/2004 | Elsey et al. |
| 2004/0259537 A1 | 12/2004 | Ackley |
| 2004/0260948 A1 | 12/2004 | Miyata et al. |
| 2004/0264396 A1 | 12/2004 | Ginzburg et al. |
| 2004/0266364 A1 | 12/2004 | Nguyen et al. |
| 2004/0268148 A1 | 12/2004 | Karjala et al. |
| 2005/0002501 A1 | 1/2005 | Elsey et al. |
| 2005/0002508 A1 | 1/2005 | Elsey et al. |
| 2005/0002509 A1 | 1/2005 | Elsey et al. |
| 2005/0002510 A1 | 1/2005 | Elsey et al. |
| 2005/0010694 A1 | 1/2005 | Ma et al. |
| 2005/0015432 A1 | 1/2005 | Cohen |
| 2005/0021750 A1 | 1/2005 | Abrams |
| 2005/0022000 A1 | 1/2005 | Inomata et al. |
| 2005/0022182 A1 | 1/2005 | Mittal |
| 2005/0027591 A9 | 2/2005 | Gailey et al. |
| 2005/0027716 A1 | 2/2005 | Apfel |
| 2005/0027869 A1 | 2/2005 | Johnson |
| 2005/0033812 A1 | 2/2005 | McCarthy et al. |
| 2005/0033926 A1 | 2/2005 | Dumont |
| 2005/0037741 A1 | 2/2005 | Gilbert |
| 2005/0038707 A1 | 2/2005 | Roever et al. |
| 2005/0038724 A1 | 2/2005 | Roever et al. |
| 2005/0038863 A1 | 2/2005 | Onyon et al. |
| 2005/0041793 A1 | 2/2005 | Fulton et al. |
| 2005/0044144 A1 | 2/2005 | Malik et al. |
| 2005/0055578 A1 | 3/2005 | Wright et al. |
| 2005/0063544 A1 | 3/2005 | Uusitalo et al. |
| 2005/0071489 A1 | 3/2005 | Parupudi et al. |
| 2005/0071674 A1 | 3/2005 | Chou et al. |
| 2005/0073982 A1 | 4/2005 | Corneille et al. |
| 2005/0076136 A1 | 4/2005 | Cho et al. |
| 2005/0076241 A1 | 4/2005 | Appelman |
| 2005/0086540 A1 | 4/2005 | Gunter et al. |
| 2005/0094625 A1 | 5/2005 | Bouat |
| 2005/0097225 A1 | 5/2005 | Glatt et al. |
| 2005/0097570 A1 | 5/2005 | Bomers |
| 2005/0101307 A1 | 5/2005 | Brugge et al. |
| 2005/0102257 A1 | 5/2005 | Onyon et al. |
| 2005/0102328 A1 | 5/2005 | Ring et al. |
| 2005/0102351 A1 | 5/2005 | Jiang et al. |
| 2005/0108427 A1 | 5/2005 | Datta |
| 2005/0117606 A1 | 6/2005 | Kim |
| 2005/0120082 A1 | 6/2005 | Hesselink et al. |
| 2005/0120084 A1 | 6/2005 | Hu et al. |
| 2005/0120181 A1 | 6/2005 | Arunagirinathan et al. |
| 2005/0122333 A1 | 6/2005 | Sumanaweera et al. |
| 2005/0124332 A1 | 6/2005 | Clark et al. |
| 2005/0138111 A1 | 6/2005 | Aton et al. |
| 2005/0138176 A1 | 6/2005 | Singh et al. |
| 2005/0144219 A1 | 6/2005 | Terada |
| 2005/0147130 A1 | 7/2005 | Hurwitz et al. |
| 2005/0154698 A1 | 7/2005 | Ikezawa et al. |
| 2005/0154796 A1 | 7/2005 | Forsyth |
| 2005/0154836 A1 | 7/2005 | Steely et al. |
| 2005/0155027 A1 | 7/2005 | Wei |
| 2005/0164703 A1 | 7/2005 | Huynh |
| 2005/0164721 A1 | 7/2005 | Yeh et al. |
| 2005/0165909 A1 | 7/2005 | Cromer et al. |
| 2005/0170776 A1 | 8/2005 | Siorpaes |
| 2005/0183143 A1 | 8/2005 | Anderholm et al. |
| 2005/0188038 A1 | 8/2005 | Yabe |
| 2005/0193036 A1 | 9/2005 | Phillips et al. |
| 2005/0193096 A1 | 9/2005 | Yu et al. |
| 2005/0198170 A1 | 9/2005 | LaMay et al. |
| 2005/0203966 A1 | 9/2005 | Labrou et al. |
| 2005/0210104 A1 | 9/2005 | Torvinen |
| 2005/0210125 A1 | 9/2005 | Li |
| 2005/0222891 A1 | 10/2005 | Chan et al. |
| 2005/0228812 A1 | 10/2005 | Hansmann et al. |
| 2005/0232295 A1 | 10/2005 | Young |
| 2005/0234860 A1 | 10/2005 | Roever et al. |
| 2005/0235214 A1 | 10/2005 | Shimizu et al. |
| 2005/0246139 A1 | 11/2005 | Rivenbark et al. |
| 2005/0248526 A1 | 11/2005 | Twerdahl et al. |
| 2005/0251555 A1 | 11/2005 | Little, II |
| 2005/0254443 A1 | 11/2005 | Campbell et al. |
| 2005/0262220 A1 | 11/2005 | Ecklund et al. |
| 2005/0273804 A1 | 12/2005 | Preisman |
| 2005/0278307 A1 | 12/2005 | Battagin et al. |
| 2005/0278641 A1 | 12/2005 | Mansour et al. |
| 2005/0278647 A1 | 12/2005 | Leavitt et al. |
| 2005/0288006 A1 | 12/2005 | Apfel |
| 2006/0012672 A1 | 1/2006 | Schrader et al. |
| 2006/0020525 A1 | 1/2006 | Borelli et al. |
| 2006/0020580 A1 | 1/2006 | Dettinger et al. |
| 2006/0020804 A1 | 1/2006 | Schleifer et al. |
| 2006/0020947 A1 | 1/2006 | Hallamaa et al. |
| 2006/0021023 A1 | 1/2006 | Stewart et al. |
| 2006/0022048 A1 | 2/2006 | Johnson |
| 2006/0026580 A1 | 2/2006 | Cabillic et al. |
| 2006/0029062 A1 | 2/2006 | Rao et al. |
| 2006/0029063 A1 | 2/2006 | Rao et al. |
| 2006/0029064 A1 | 2/2006 | Rao et al. |
| 2006/0031114 A1 | 2/2006 | Zommers |
| 2006/0031300 A1 | 2/2006 | Kock et al. |
| 2006/0031365 A1 | 2/2006 | Kay et al. |
| 2006/0031428 A1 | 2/2006 | Wikman |
| 2006/0031785 A1 | 2/2006 | Raciborski |
| 2006/0037071 A1 | 2/2006 | Rao et al. |
| 2006/0046686 A1 | 3/2006 | Hawkins et al. |
| 2006/0047844 A1 | 3/2006 | Deng |
| 2006/0048061 A1 | 3/2006 | Forlenza et al. |
| 2006/0052091 A1 | 3/2006 | Onyon et al. |
| 2006/0052137 A1 | 3/2006 | Randall et al. |
| 2006/0059495 A1 | 3/2006 | Spector |
| 2006/0063544 A1 | 3/2006 | Zhao et al. |
| 2006/0069686 A1 | 3/2006 | Beyda et al. |
| 2006/0069687 A1 | 3/2006 | Cui et al. |
| 2006/0069715 A1 | 3/2006 | Vayssiere |
| 2006/0069742 A1 | 3/2006 | Segre |
| 2006/0069746 A1 | 3/2006 | Davis et al. |
| 2006/0073810 A1 | 4/2006 | Pyhalammi et al. |
| 2006/0074951 A1 | 4/2006 | Beier et al. |
| 2006/0075028 A1 | 4/2006 | Zager et al. |
| 2006/0084410 A1 | 4/2006 | Sutaria et al. |
| 2006/0085503 A1 | 4/2006 | Stoye et al. |
| 2006/0093026 A1 | 5/2006 | Montojo et al. |
| 2006/0093135 A1 | 5/2006 | Fiatal et al. |
| 2006/0099969 A1 | 5/2006 | Staton et al. |
| 2006/0099970 A1 | 5/2006 | Morgan et al. |
| 2006/0112177 A1 | 5/2006 | Barkley et al. |
| 2006/0123042 A1 | 6/2006 | Xie et al. |
| 2006/0132495 A1 | 6/2006 | Anderson |
| 2006/0141962 A1 | 6/2006 | Forbes et al. |
| 2006/0143464 A1 | 6/2006 | Ananthanarayanan et al. |
| 2006/0149591 A1 | 7/2006 | Hanf et al. |
| 2006/0149843 A1 | 7/2006 | Rhoads et al. |
| 2006/0149970 A1 | 7/2006 | Imazu |
| 2006/0155822 A1 | 7/2006 | Yang et al. |
| 2006/0161621 A1 | 7/2006 | Rosenberg |
| 2006/0165226 A1 | 7/2006 | Ernst et al. |
| 2006/0167969 A1 | 7/2006 | Andreev et al. |
| 2006/0168043 A1 | 7/2006 | Eisenberger et al. |
| 2006/0168164 A1 | 7/2006 | Lemson |
| 2006/0179410 A1 | 8/2006 | Deeds |
| 2006/0188864 A1 | 8/2006 | Shah |
| 2006/0190428 A1 | 8/2006 | Jung et al. |

(56) References Cited

U.S. PATENT DOCUMENTS

| | | |
|---|---|---|
| 2006/0190569 A1 | 8/2006 | Neil et al. |
| 2006/0190984 A1 | 8/2006 | Heard et al. |
| 2006/0192014 A1 | 8/2006 | Hamilton et al. |
| 2006/0195570 A1 | 8/2006 | Zellner et al. |
| 2006/0209842 A1 | 9/2006 | Creamer et al. |
| 2006/0212531 A1 | 9/2006 | Kikkawa et al. |
| 2006/0224629 A1 | 10/2006 | Alexander et al. |
| 2006/0230394 A1 | 10/2006 | Forth et al. |
| 2006/0240804 A1 | 10/2006 | Backholm et al. |
| 2006/0240805 A1 | 10/2006 | Backholm et al. |
| 2006/0242137 A1 | 10/2006 | Shah et al. |
| 2006/0242210 A1 | 10/2006 | Ring et al. |
| 2006/0242320 A1 | 10/2006 | Nettle et al. |
| 2006/0242607 A1 | 10/2006 | Hudson |
| 2006/0252435 A1 | 11/2006 | Henderson et al. |
| 2006/0253456 A1 | 11/2006 | Pacholec et al. |
| 2006/0253605 A1 | 11/2006 | Sundarrajan et al. |
| 2006/0259923 A1 | 11/2006 | Chiu |
| 2006/0265595 A1 | 11/2006 | Scottodiluzio |
| 2006/0271884 A1 | 11/2006 | Hurst |
| 2006/0277265 A1 | 12/2006 | Backholm et al. |
| 2006/0277271 A1 | 12/2006 | Morse et al. |
| 2006/0294071 A1 | 12/2006 | Weare et al. |
| 2006/0294223 A1 | 12/2006 | Glasgow et al. |
| 2007/0005738 A1 | 1/2007 | Alexion-Tiernan et al. |
| 2007/0006317 A1 | 1/2007 | Asami et al. |
| 2007/0011367 A1 | 1/2007 | Scott et al. |
| 2007/0019610 A1 | 1/2007 | Backholm et al. |
| 2007/0022118 A1 | 1/2007 | Layne |
| 2007/0027775 A1 | 2/2007 | Hwang |
| 2007/0027832 A1 | 2/2007 | Fiatal et al. |
| 2007/0027886 A1 | 2/2007 | Gent et al. |
| 2007/0027917 A1 | 2/2007 | Ariel et al. |
| 2007/0027920 A1 | 2/2007 | Alvarado et al. |
| 2007/0027921 A1 | 2/2007 | Alvarado et al. |
| 2007/0027930 A1 | 2/2007 | Alvarado et al. |
| 2007/0033531 A1 | 2/2007 | Marsh |
| 2007/0038567 A1 | 2/2007 | Allaire et al. |
| 2007/0038931 A1 | 2/2007 | Allaire et al. |
| 2007/0044041 A1 | 2/2007 | Beynon et al. |
| 2007/0049258 A1 | 3/2007 | Thibeault |
| 2007/0060196 A1 | 3/2007 | Sharma |
| 2007/0061393 A1 | 3/2007 | Moore |
| 2007/0067147 A1 | 3/2007 | Huang |
| 2007/0067381 A1 | 3/2007 | Grant et al. |
| 2007/0067424 A1 | 3/2007 | Raciborski et al. |
| 2007/0070931 A1 | 3/2007 | Lewis et al. |
| 2007/0072617 A1 | 3/2007 | Lewis et al. |
| 2007/0078857 A1 | 4/2007 | Punaganti et al. |
| 2007/0078964 A1 | 4/2007 | East et al. |
| 2007/0088852 A1 | 4/2007 | Levkovitz |
| 2007/0105627 A1 | 5/2007 | Campbell |
| 2007/0111764 A1 | 5/2007 | Park et al. |
| 2007/0116223 A1 | 5/2007 | Burke et al. |
| 2007/0118620 A1 | 5/2007 | Cartmell et al. |
| 2007/0130108 A1 | 6/2007 | Simpson et al. |
| 2007/0130217 A1 | 6/2007 | Linyard et al. |
| 2007/0140193 A1 | 6/2007 | Dosa et al. |
| 2007/0147317 A1 | 6/2007 | Smith et al. |
| 2007/0147411 A1 | 6/2007 | Bijwaard et al. |
| 2007/0150881 A1 | 6/2007 | Khawand et al. |
| 2007/0156824 A1 | 7/2007 | Thompson |
| 2007/0156842 A1 | 7/2007 | Vermeulen et al. |
| 2007/0162514 A1 | 7/2007 | Civetta et al. |
| 2007/0167178 A1 | 7/2007 | Al-Harbi |
| 2007/0174433 A1 | 7/2007 | Mendez et al. |
| 2007/0175998 A1 | 8/2007 | Lev |
| 2007/0198698 A1 | 8/2007 | Boyd et al. |
| 2007/0202954 A1* | 8/2007 | Morrow et al. .............. 463/42 |
| 2007/0220080 A1 | 9/2007 | Humphrey |
| 2007/0220099 A1 | 9/2007 | Di Giorgio et al. |
| 2007/0233855 A1 | 10/2007 | Brown et al. |
| 2007/0237318 A1 | 10/2007 | McGary |
| 2007/0245010 A1 | 10/2007 | Arn et al. |
| 2007/0249365 A1 | 10/2007 | Jendbro |
| 2007/0250591 A1 | 10/2007 | Milic-Frayling et al. |
| 2007/0254631 A1 | 11/2007 | Spooner |
| 2007/0255848 A1 | 11/2007 | Sewall et al. |
| 2007/0264993 A1 | 11/2007 | Hughes |
| 2007/0267492 A1 | 11/2007 | Maclaine Pont |
| 2007/0276925 A1 | 11/2007 | LaJoie et al. |
| 2007/0276926 A1 | 11/2007 | LaJoie et al. |
| 2007/0288469 A1 | 12/2007 | Shenfield |
| 2007/0290787 A1 | 12/2007 | Fiatal et al. |
| 2007/0293207 A1 | 12/2007 | Guedalia et al. |
| 2007/0293238 A1 | 12/2007 | Fiatal et al. |
| 2007/0293958 A1 | 12/2007 | Stehle et al. |
| 2007/0294295 A1 | 12/2007 | Finkelstein et al. |
| 2007/0294763 A1 | 12/2007 | Udezue et al. |
| 2007/0296701 A1 | 12/2007 | Pope et al. |
| 2007/0299918 A1 | 12/2007 | Roberts |
| 2008/0001717 A1 | 1/2008 | Fiatal |
| 2008/0008095 A1 | 1/2008 | Gilfix |
| 2008/0009344 A1 | 1/2008 | Graham et al. |
| 2008/0016236 A1 | 1/2008 | Beverly et al. |
| 2008/0032718 A1 | 2/2008 | Suresh |
| 2008/0034031 A1 | 2/2008 | Weisbrot et al. |
| 2008/0037787 A1 | 2/2008 | Boynton et al. |
| 2008/0059308 A1 | 3/2008 | Gerken |
| 2008/0059398 A1 | 3/2008 | Tsutsui |
| 2008/0061142 A1 | 3/2008 | Howcroft et al. |
| 2008/0068519 A1 | 3/2008 | Adler et al. |
| 2008/0077506 A1 | 3/2008 | Rampell et al. |
| 2008/0077571 A1 | 3/2008 | Harris et al. |
| 2008/0085719 A1 | 4/2008 | Kuchibhotla et al. |
| 2008/0085724 A1 | 4/2008 | Cormier et al. |
| 2008/0086379 A1 | 4/2008 | Dion et al. |
| 2008/0091773 A1 | 4/2008 | Hameen-Anttila |
| 2008/0103877 A1 | 5/2008 | Gerken |
| 2008/0104666 A1 | 5/2008 | Dillaway |
| 2008/0108298 A1 | 5/2008 | Selen et al. |
| 2008/0114881 A1 | 5/2008 | Lee et al. |
| 2008/0125225 A1 | 5/2008 | Lazaridis et al. |
| 2008/0130663 A1 | 6/2008 | Fridman et al. |
| 2008/0133326 A1 | 6/2008 | Goncalves et al. |
| 2008/0133641 A1 | 6/2008 | Gent et al. |
| 2008/0133708 A1 | 6/2008 | Alvarado et al. |
| 2008/0134292 A1 | 6/2008 | Ariel et al. |
| 2008/0140665 A1 | 6/2008 | Ariel et al. |
| 2008/0151817 A1 | 6/2008 | Fitchett et al. |
| 2008/0154870 A1 | 6/2008 | Evermann et al. |
| 2008/0155613 A1 | 6/2008 | Benya et al. |
| 2008/0166999 A1 | 7/2008 | Guedalia et al. |
| 2008/0167019 A1 | 7/2008 | Guedalia et al. |
| 2008/0168145 A1 | 7/2008 | Wilson |
| 2008/0178294 A1 | 7/2008 | Hu et al. |
| 2008/0183800 A1 | 7/2008 | Herzog et al. |
| 2008/0192820 A1 | 8/2008 | Brooks et al. |
| 2008/0198995 A1 | 8/2008 | McGary et al. |
| 2008/0201362 A1 | 8/2008 | Multer et al. |
| 2008/0201751 A1 | 8/2008 | Ahmed et al. |
| 2008/0207182 A1 | 8/2008 | Maharajh et al. |
| 2008/0209491 A1 | 8/2008 | Hasek |
| 2008/0214148 A1 | 9/2008 | Ramer et al. |
| 2008/0216094 A1 | 9/2008 | Anderson et al. |
| 2008/0220797 A1 | 9/2008 | Meiby et al. |
| 2008/0232290 A1 | 9/2008 | Elzur et al. |
| 2008/0233983 A1 | 9/2008 | Park et al. |
| 2008/0242370 A1 | 10/2008 | Lando et al. |
| 2008/0263170 A1 | 10/2008 | Caron et al. |
| 2008/0270379 A1 | 10/2008 | Ramakrishna |
| 2008/0273498 A1 | 11/2008 | Jalil et al. |
| 2008/0281798 A1 | 11/2008 | Chatterjee et al. |
| 2008/0288659 A1 | 11/2008 | Hasha et al. |
| 2008/0298386 A1 | 12/2008 | Fiatal |
| 2008/0299956 A1 | 12/2008 | Bailey et al. |
| 2008/0301231 A1 | 12/2008 | Mehta et al. |
| 2008/0301300 A1 | 12/2008 | Toub |
| 2008/0313282 A1 | 12/2008 | Warila et al. |
| 2009/0010204 A1 | 1/2009 | Pratt, Jr. et al. |
| 2009/0010259 A1 | 1/2009 | Sirotkin |
| 2009/0012841 A1 | 1/2009 | Saft et al. |
| 2009/0016526 A1 | 1/2009 | Fiatal et al. |
| 2009/0019485 A1 | 1/2009 | Ellis et al. |

(56) References Cited

U.S. PATENT DOCUMENTS

| | | |
|---|---|---|
| 2009/0019532 A1 | 1/2009 | Jacobsen et al. |
| 2009/0024794 A1 | 1/2009 | Iyer et al. |
| 2009/0031006 A1 | 1/2009 | Johnson |
| 2009/0052372 A1 | 2/2009 | Durazzo et al. |
| 2009/0054034 A1 | 2/2009 | Backholm et al. |
| 2009/0055353 A1 | 2/2009 | Meema |
| 2009/0059950 A1 | 3/2009 | Gao et al. |
| 2009/0063647 A1 | 3/2009 | Backholm et al. |
| 2009/0075683 A1 | 3/2009 | Backholm et al. |
| 2009/0077263 A1 | 3/2009 | Koganti et al. |
| 2009/0077326 A1 | 3/2009 | Motohashi |
| 2009/0094317 A1 | 4/2009 | Venkitaraman |
| 2009/0100416 A1 | 4/2009 | Brown et al. |
| 2009/0110179 A1 | 4/2009 | Elsey et al. |
| 2009/0119266 A1 | 5/2009 | Fitzpatrick et al. |
| 2009/0125523 A1 | 5/2009 | Fitzpatrick et al. |
| 2009/0144632 A1 | 6/2009 | Mendez |
| 2009/0147008 A1 | 6/2009 | Do et al. |
| 2009/0149203 A1 | 6/2009 | Backholm et al. |
| 2009/0156178 A1 | 6/2009 | Elsey et al. |
| 2009/0157792 A1 | 6/2009 | Fiatal |
| 2009/0164433 A1 | 6/2009 | R et al. |
| 2009/0164560 A1 | 6/2009 | Fiatal |
| 2009/0172565 A1 | 7/2009 | Jackson et al. |
| 2009/0181641 A1 | 7/2009 | Fiatal |
| 2009/0182500 A1 | 7/2009 | Dicke |
| 2009/0187939 A1 | 7/2009 | Lajoie |
| 2009/0191903 A1 | 7/2009 | Fiatal |
| 2009/0193130 A1 | 7/2009 | Fiatal |
| 2009/0193338 A1 | 7/2009 | Fiatal |
| 2009/0215504 A1 | 8/2009 | Lando |
| 2009/0221326 A1 | 9/2009 | Roussel et al. |
| 2009/0228545 A1 | 9/2009 | Mendez et al. |
| 2009/0241180 A1 | 9/2009 | Fiatal |
| 2009/0248670 A1 | 10/2009 | Fiatal |
| 2009/0248696 A1 | 10/2009 | Rowles et al. |
| 2009/0248794 A1 | 10/2009 | Helms et al. |
| 2009/0248878 A1 | 10/2009 | Tran et al. |
| 2009/0252136 A1 | 10/2009 | Mahany et al. |
| 2009/0254589 A1 | 10/2009 | Nair et al. |
| 2009/0254971 A1 | 10/2009 | Herz et al. |
| 2009/0264138 A1 | 10/2009 | Kang et al. |
| 2009/0282125 A1 | 11/2009 | Jeide et al. |
| 2009/0286531 A1 | 11/2009 | Bhatt et al. |
| 2009/0287750 A1 | 11/2009 | Banavar et al. |
| 2009/0299817 A1 | 12/2009 | Fok et al. |
| 2009/0307133 A1 | 12/2009 | Holloway et al. |
| 2009/0318171 A1 | 12/2009 | Backholm et al. |
| 2009/0323678 A1 | 12/2009 | Wang |
| 2009/0325565 A1 | 12/2009 | Backholm |
| 2009/0327390 A1 | 12/2009 | Tran et al. |
| 2010/0042691 A1 | 2/2010 | Maguire |
| 2010/0049872 A1 | 2/2010 | Roskind |
| 2010/0057924 A1 | 3/2010 | Rauber et al. |
| 2010/0069127 A1 | 3/2010 | Fiennes |
| 2010/0077035 A1 | 3/2010 | Li et al. |
| 2010/0077083 A1 | 3/2010 | Tran et al. |
| 2010/0083255 A1 | 4/2010 | Bane et al. |
| 2010/0087167 A1 | 4/2010 | Tsurutome et al. |
| 2010/0088722 A1 | 4/2010 | Jiang |
| 2010/0093273 A1 | 4/2010 | Hohl |
| 2010/0115050 A1 | 5/2010 | Sultenfuss et al. |
| 2010/0118190 A1 | 5/2010 | Salfati et al. |
| 2010/0131593 A1 | 5/2010 | Kihara et al. |
| 2010/0131617 A1 | 5/2010 | Osborne et al. |
| 2010/0146107 A1 | 6/2010 | Fiatal |
| 2010/0149975 A1 | 6/2010 | Tripathi et al. |
| 2010/0174735 A1 | 7/2010 | Fiatal |
| 2010/0174939 A1 | 7/2010 | Vexler |
| 2010/0186011 A1 | 7/2010 | Magenheimer |
| 2010/0207870 A1 | 8/2010 | Cho |
| 2010/0211651 A1 | 8/2010 | Guedalia et al. |
| 2010/0214984 A1 | 8/2010 | Cho et al. |
| 2010/0227594 A1 | 9/2010 | DeVries |
| 2010/0228863 A1 | 9/2010 | Kawauchi |
| 2010/0229096 A1 | 9/2010 | Maiocco et al. |
| 2010/0238915 A1 | 9/2010 | Cayla et al. |
| 2010/0250706 A1 | 9/2010 | Burckart et al. |
| 2010/0250986 A1 | 9/2010 | Black et al. |
| 2010/0268757 A1 | 10/2010 | Fisher |
| 2010/0274983 A1 | 10/2010 | Murphy et al. |
| 2010/0279662 A1 | 11/2010 | Kuusinen et al. |
| 2010/0293335 A1 | 11/2010 | Muthiah et al. |
| 2010/0299223 A1 | 11/2010 | Crouch |
| 2010/0313018 A1 | 12/2010 | Jorgensen |
| 2010/0319054 A1 | 12/2010 | Mehta et al. |
| 2010/0322124 A1 | 12/2010 | Luoma et al. |
| 2010/0325306 A1 | 12/2010 | Vimpari et al. |
| 2011/0028129 A1 | 2/2011 | Hutchison et al. |
| 2011/0040718 A1 | 2/2011 | Tendjoukian et al. |
| 2011/0065424 A1 | 3/2011 | Estevez et al. |
| 2011/0066646 A1 | 3/2011 | Danado et al. |
| 2011/0099363 A1 | 4/2011 | Boynton et al. |
| 2011/0113109 A1 | 5/2011 | LeVasseur et al. |
| 2011/0119134 A1 | 5/2011 | Zivkovic et al. |
| 2011/0126060 A1 | 5/2011 | Grube et al. |
| 2011/0138102 A1 | 6/2011 | Glikson et al. |
| 2011/0138402 A1 | 6/2011 | Fleming |
| 2011/0153937 A1 | 6/2011 | Annamalaisami et al. |
| 2011/0158239 A1 | 6/2011 | Mohaban |
| 2011/0165889 A1 | 7/2011 | Fiatal et al. |
| 2011/0179138 A1 | 7/2011 | Van Geest et al. |
| 2011/0179377 A1 | 7/2011 | Fleming |
| 2011/0182220 A1 | 7/2011 | Black et al. |
| 2011/0184827 A1 | 7/2011 | Hubert |
| 2011/0185355 A1 | 7/2011 | Chawla et al. |
| 2011/0190014 A1 | 8/2011 | Fiatal |
| 2011/0191474 A1 | 8/2011 | Fiatal |
| 2011/0201304 A1 | 8/2011 | Sutaria et al. |
| 2011/0207436 A1 | 8/2011 | van Gent et al. |
| 2011/0208810 A1 | 8/2011 | Li et al. |
| 2011/0213800 A1 | 9/2011 | Saros et al. |
| 2011/0213898 A1 | 9/2011 | Fiatal et al. |
| 2011/0214182 A1 | 9/2011 | Adams et al. |
| 2011/0238772 A1 | 9/2011 | Fiatal |
| 2011/0246950 A1 | 10/2011 | Luna et al. |
| 2011/0252088 A1 | 10/2011 | Fiatal |
| 2011/0264622 A1 | 10/2011 | Vargas et al. |
| 2011/0264731 A1 | 10/2011 | Knowles et al. |
| 2011/0294463 A1 | 12/2011 | Fiatal |
| 2011/0294464 A1 | 12/2011 | Fiatal |
| 2011/0296050 A1 | 12/2011 | Cherukuri |
| 2011/0296120 A1 | 12/2011 | Khan |
| 2011/0296415 A1 | 12/2011 | Khan et al. |
| 2011/0302154 A1 | 12/2011 | Snyder |
| 2012/0005276 A1 | 1/2012 | Guo et al. |
| 2012/0008536 A1 | 1/2012 | Tervahauta et al. |
| 2012/0022980 A1 | 1/2012 | Angelone |
| 2012/0023190 A1 | 1/2012 | Backholm et al. |
| 2012/0023226 A1 | 1/2012 | Petersen et al. |
| 2012/0023236 A1 | 1/2012 | Backholm et al. |
| 2012/0030280 A1 | 2/2012 | Wang et al. |
| 2012/0030750 A1 | 2/2012 | Bhargara et al. |
| 2012/0054386 A1 | 3/2012 | Hanes |
| 2012/0072910 A1* | 3/2012 | Martin et al. .................. 718/1 |
| 2012/0077482 A1 | 3/2012 | Backholm |
| 2012/0078996 A1 | 3/2012 | Shah |
| 2012/0096092 A1 | 4/2012 | Davidge et al. |
| 2012/0108225 A1 | 5/2012 | Luna et al. |
| 2012/0110109 A1 | 5/2012 | Luna et al. |
| 2012/0110110 A1 | 5/2012 | Luna et al. |
| 2012/0110111 A1 | 5/2012 | Luna et al. |
| 2012/0110112 A1 | 5/2012 | Luna et al. |
| 2012/0110118 A1 | 5/2012 | Luna et al. |
| 2012/0110171 A1 | 5/2012 | Luna et al. |
| 2012/0110173 A1 | 5/2012 | Luna et al. |
| 2012/0110174 A1 | 5/2012 | Wootton et al. |
| 2012/0110275 A1 | 5/2012 | Ganti et al. |
| 2012/0130973 A1 | 5/2012 | Tamm et al. |
| 2012/0131095 A1 | 5/2012 | Luna et al. |
| 2012/0131184 A1 | 5/2012 | Luna et al. |
| 2012/0135726 A1 | 5/2012 | Luna et al. |
| 2012/0140750 A1 | 6/2012 | Yan et al. |
| 2012/0149352 A1 | 6/2012 | Backholm et al. |

(56) References Cited

U.S. PATENT DOCUMENTS

| | | |
|---|---|---|
| 2012/0151044 A1 | 6/2012 | Luna et al. |
| 2012/0157170 A1 | 6/2012 | Backholm et al. |
| 2012/0158837 A1 | 6/2012 | Kaul |
| 2012/0158908 A1 | 6/2012 | Luna et al. |
| 2012/0170496 A1 | 7/2012 | Yang et al. |
| 2012/0173616 A1 | 7/2012 | Luna et al. |
| 2012/0174220 A1 | 7/2012 | Rodriguez |
| 2012/0176968 A1 | 7/2012 | Luna |
| 2012/0178414 A1 | 7/2012 | Fiatal |
| 2012/0179801 A1 | 7/2012 | Luna et al. |
| 2012/0185597 A1 | 7/2012 | Luna |
| 2012/0185918 A1 | 7/2012 | Backholm et al. |
| 2012/0210121 A1 | 8/2012 | Boynton et al. |
| 2012/0226767 A1 | 9/2012 | Luna et al. |
| 2012/0227059 A1 | 9/2012 | Fleming |
| 2012/0246333 A1 | 9/2012 | Fiatal |
| 2013/0086228 A1* | 4/2013 | Goldman ............. 709/219 |

FOREIGN PATENT DOCUMENTS

| | | |
|---|---|---|
| EP | 1422899 A1 | 5/2004 |
| EP | 1466261 A1 | 10/2004 |
| EP | 1466435 A1 | 10/2004 |
| EP | 1482702 A1 | 12/2004 |
| EP | 1815634 A1 | 8/2007 |
| EP | 1815652 A1 | 8/2007 |
| EP | 1817883 A1 | 8/2007 |
| FI | 117152 B | 6/2006 |
| FI | 118288 B | 9/2007 |
| FI | 119581 B | 12/2008 |
| JP | 4154233 A | 5/1992 |
| JP | 10-336372 A | 12/1998 |
| JP | 2001-218185 A | 8/2001 |
| JP | 2001-350718 A | 12/2001 |
| JP | 2001-356973 A | 12/2001 |
| JP | 2005-515664 T | 5/2005 |
| JP | 2009-207177 A | 9/2009 |
| JP | 4386732 B2 | 10/2009 |
| KR | 2001-0018568 A | 3/2001 |
| KR | 2006-0068186 A | 6/2006 |
| KR | 2007-0071858 A1 | 7/2007 |
| KR | 10-0765238 B1 | 10/2007 |
| KR | 2007-0102091 A1 | 10/2007 |
| KR | 2007-0117874 A | 12/2007 |
| KR | 2009-0077515 A | 7/2009 |
| KR | 2010-0064605 A | 6/2010 |
| WO | WO 97/41661 A2 | 11/1997 |
| WO | WO 98/24257 A1 | 6/1998 |
| WO | WO 98/58322 A2 | 12/1998 |
| WO | WO 01/30130 A2 | 5/2001 |
| WO | WO 03/007570 A1 | 1/2003 |
| WO | WO 03/058483 A1 | 7/2003 |
| WO | WO 03/058879 A1 | 7/2003 |
| WO | WO 03/065701 A1 | 8/2003 |
| WO | WO 03/098890 A1 | 11/2003 |
| WO | WO 2004/017591 A2 | 2/2004 |
| WO | WO 2004/045171 A1 | 5/2004 |
| WO | WO 2005/015925 A2 | 2/2005 |
| WO | WO 2005/020108 A1 | 3/2005 |
| WO | WO 2006/045005 A2 | 4/2006 |
| WO | WO 2006/045102 A2 | 4/2006 |
| WO | WO 2006/053952 A1 | 5/2006 |
| WO | WO 2006/053954 A1 | 5/2006 |
| WO | WO 2006/058967 A1 | 6/2006 |
| WO | WO 2007/015725 A2 | 2/2007 |
| WO | WO 2007/015726 A1 | 2/2007 |
| WO | WO 2007/149526 A2 | 12/2007 |
| WO | WO 2007/149540 A2 | 12/2007 |
| WO | WO 2008/061042 A | 5/2008 |
| WO | WO 2011/126889 A2 | 10/2011 |
| WO | WO 2012/018430 A1 | 2/2012 |
| WO | WO 2012/018431 A1 | 2/2012 |
| WO | WO 2012/018477 A2 | 2/2012 |
| WO | WO 2012/018479 A2 | 2/2012 |
| WO | WO 2012/018556 A2 | 2/2012 |
| WO | WO 2012/024030 A2 | 2/2012 |
| WO | WO 2012/060995 A2 | 5/2012 |
| WO | WO 2012/060996 A2 | 5/2012 |
| WO | WO 2012/060997 A2 | 5/2012 |
| WO | WO 2012/061430 A2 | 5/2012 |
| WO | WO 2012/061433 A2 | 5/2012 |
| WO | WO 2012/061437 A1 | 5/2012 |
| WO | WO 2012/071283 A1 | 5/2012 |
| WO | WO 2012/071384 A2 | 5/2012 |
| WO | WO 2012/094675 A2 | 7/2012 |

OTHER PUBLICATIONS

Android Developers, "Date," 10 pages, Oct. 27, 2011.
Augun, Audrey, "Integrating Lotus Notes With Enterprise Data," Lotus Notes Advisory, pp. 22-25, Jul.-Aug. 1996.
Balaban, Bob, "This Is Not Your Father's Basic: LotusScript In Notes Release 4," The View, vol. 1, Issue 5, 32 pages, Nov.-Dec. 1995.
Bedell, Doug, "Meeting Your New Best Friends Six Degrees Widens Your Contacts In Exchange For Sampling Web Sites," The Dallas Morning News, 4 pages, Oct. 27, 1998.
Bergman, Lawrence D. et al., "Programming-By-Demonstration For Behavior-Based User Interface Customization," IBM Research Report, RC23116, 5 pages, Feb. 20, 2004.
B'Far, Reza et al., "Designing Effective User Interfaces For Wireless Devices," Publication Unknown, 14 pages, Published prior to Feb. 23, 2006.
Blaney, Jeff, "You Can Take It With You—An Introduction To Mobile Computing With Notes R4," The View, vol. 2, Issue 1, 14 pages, Jan.-Feb. 1996.
Braden, R., "Requirements For Internet Hosts—Application And Support," RFC 1123, 80 pages, Oct. 1989.
Brown, Kevin et al., "Mastering Lotus Notes®," Sybex Inc., 996 pages, 1995.
"Chapter: About NotesPump," Publication Unknown, 480 pages, Published prior to Jan. 8, 2003.
"Chapter 13-1—Anatomy Of A Note ID," Publication Unknown, 8 pages, Published prior to Jan. 8, 2003.
Cole, Barb et al., "Lotus Airs Notes-To-Database Integration Tool," Network World, 2 pages, Oct. 2, 1995.
"CR 3483 to Release 8 TS 25.331, Rev. 2," 3GPP TSG-RAN2 Meeting #64, Prague, Czech Republic, 11 pages, Nov. 10-14, 2008.
"CR 4100 to Release 8 TS 25.331, Rev. 1," 3GPP TSG-RAN WG2 Meeting #69, San Francisco, U.S., 6 pages, Feb. 22-26, 2010.
Dahl, Andrew, "Lotus Notes® 4 Administrator's Survival Guide," Sams Publishing, 64 pages, 1996.
Decker, Stefan et al., "The Social Semantic Desktop," Digital Enterprise Research Institute, DERI Technical Report May 2, 2004, 7 pages, May 2004.
Elz, R. et al., "Clarifications To The DNS Specification," RFC 2181, 12 pages, Jul. 1997.
Eronen, "TCP Wake-Up: Reducing Keep-Alive Traffic In Mobile IPv4 And Ipsec NAT Traversal," NRC-TR-2008-002, Nokia, 10 pages, Jan. 31, 2008.
European Patent Application No. EP 03705704.9, Supplementary European Search Report, 4 pages, Jun. 9, 2010.
European Patent Application No. EP 03707338.4, Supplementary European Search Report, 2 pages, Apr. 18, 2011.
European Patent Application No. EP 05815115.0, Supplementary European Search Report, 7 pages, Nov. 17, 2011.
Falkner, Mike, "How To Plan, Develop, And Implement Lotus Notes® In Your Organization," John Wiley & Sons, Inc., 539 pages, 1996.
Freeland, Pat et al., "Lotus Notes 3-3.1 For Dummies™," IDG Books Worldwide, 389 pages, 1994.
Frenkel, Garry, "Pumping For Info: Notes and Database Integration," Network Computing, 10 pages, May 1, 1996.
Gameline, Advertisement, 1 page, 1982.
Gewirtz, David, "Lotus Notes 3 Revealed!," Prima Publishing, 261 pages, 1994.
Grous, Paul J., "Creating And Managing A Web Site With Lotus Internotes Web Publisher," The View, vol. 1, Issue 4, 20 pages, Sep.-Oct. 1995.

(56) References Cited

OTHER PUBLICATIONS

GSM Association, "Network Efficiency Task Force Fast Dormancy Best Practices," V1.0, 21 pages, May 26, 2010.
Haas, Zygmunt J. et al., "Mobile-TCP: An Asymmetric Transport Protocol Design For Mobile Systems," IEEE, pp. 1054-1058, 1997.
Haas, Zygmunt J. et al., "The Design And Performance Of Mobile TCP For Wireless Networks," Journal of High Speed Networks, vol. 10, pp. 187-207, 2001.
Hajdu, Kalman et al., "Lotus Notes Release 4 In A Multiplatform Environment," IBM Corporation, 173 pages, Feb. 1996.
Hardy, Ed, "Microsoft Proposes Two New Thumb-Driven User Interfaces," Brighthand Consulting, Inc., 2 pages, 2003.
IBM Corporation, "The Architecture Of Lotus Notes," White Paper No. 114654, 26 pages, May 31, 1995.
IBM Corporation, "The History Of Notes And Domino," Lotus Developer Domain, 11 pages, Sep. 29, 2003.
ImTOO, "ImTOO iPod Movie Converter," 3 pages, Nov. 9, 2005.
IntelliLink Corporation, "IntelliLink® For Windows User's Guide," Version 3.0, 167 pages, 1994.
International Application No. PCT/US2003/000618, International Search Report, 1 page, Apr. 4, 2003.
International Application No. PCT/US2003/000624, International Search Report, 2 pages, May 13, 2003.
International Application No. PCT/US2005/037702, International Preliminary Examination Report, 6 pages, Nov. 20, 2007.
International Application No. PCT/US2005/037702, International Search Report, 1 page, Nov. 5, 2007.
International Application No. PCT/US2005/037702, Written Opinion, 6 pages, Nov. 5, 2007.
International Application No. PCT/US2005/038135, International Search Report, 2 pages, Aug. 8, 2008.
International Application No. PCT/US2005/038135, Written Opinion, 8 pages, Aug. 8, 2008.
International Application No. PCT/US2005/038135, International Preliminary Report on Patentability, 9 pages, Oct. 31, 2011.
International Application No. PCT/FI2005/050424, International Search Report, 4 pages, Mar. 2, 2006.
International Application No. PCT/FI2005/050426, International Search Report, 3 pages, Mar. 1, 2006.
International Application No. PCT/FI2005/050441, International Search Report, 3 pages, Mar. 1, 2006.
International Application No. PCT/US2006/023426, International Search Report, 1 page, Feb. 21, 2007.
International Application No. PCT/US2006/023427, International Search Report, 1 page, Oct. 12, 2006.
International Application No. PCT/US2007/014462, International Search Report, 1 page, Jul. 2, 2008.
International Application No. PCT/US2007/014497, International Search Report, 1 page, Aug. 25, 2008.
International Application No. PCT/US2011/030534, International Search Report & Written Opinion, 10 pages, Dec. 29, 2011.
International Application No. PCT/US2011/037932, International Search Report & Written Opinion, 9 pages, Jan. 2, 2012.
International Application No. PCT/US2011/037943, International Search Report & Written Opinion, 11 pages, Jan. 2, 2012.
International Application No. PCT/US2011/043322, International Search Report & Written Opinion, 9 pages, Feb. 9, 2012.
International Application No. PCT/US2011/043328, International Search Report & Written Opinion, 12 pages, Feb. 27, 2012.
International Application No. PCT/US2011/043409, International Search Report, 11 pages, Feb. 9, 2012.
International Application No. PCT/US2011/044974, International Search Report, 15 pages, Jun. 1, 2012.
International Application No. PCT/US2011/056474, International Search Report & Written Opinion, 9 pages, May 4, 2012.
International Application No. PCT/US2011/056476, International Search Report & Written Opinion, 12 pages, May 24, 2012.
International Application No. PCT/US2011/056478, International Search Report & Written Opinion, 11 pages, May 31, 2012.
International Application No. PCT/US2011/058840, International Search Report & Written Opinion, 10 pages, Apr. 26, 2012.
International Application No. PCT/US2011/058843, International Search Report & Written Opinion, 11 pages, May 16, 2012.
International Application No. PCT/US2011/058848, International Search Report & Written Opinion, 10 pages, Apr. 10, 2012.
International Application No. PCT/US2011/061512, International Search Report, 10 pages, May 10, 2012.
International Application No. PCT/US2011/061795, International Search Report & Written Opinion, 10 pages, Jul. 31, 2012.
International Application No. PCT/US2012/020669, International Search Report & Written Opinion, 10 pages, Sep. 12, 2012.
International Application No. PCT/US2012/021459, International Search Report & Written Opinion, 10 pages, Jun. 1, 2012.
International Application No. PCT/US2012/022121, International Search Report & Written Opinion, 11 pages, May 14, 2012.
Japanese Patent Application No. 2003-558726, Office Action, 2 pages, Jun. 10, 2008.
Karlson, Amy K. et al., "AppLens And LaunchTile: Two Designs For One-Handed Thumb Use On Small Devices," Proceedings of CHI 2005, 10 pages, Apr. 2-7, 2005.
Kent, S. et al., "Security Architecture For The Internet Protocol," RFC 2401, The Internet Society, 62 pages, Nov. 1998.
Kleinberg, Jon, "The Small-World Phenomenon: An Algorithmic Perspective," Cornell Computer Science Technical Report 99-1776, 14 pages, Oct. 1999.
Koeppel, Dan, "GUIs Just Want To Have Fun," Wired Magazine, Issue 8.10, 12 pages, Oct. 2000.
Kornblith, Polly Russell, "Lotus Notes Answers: Certified Tech Support," Covers Release 3, McGraw-Hill, Inc., 326 pages, 1994.
Kreisle, Bill, "Teach Yourself . . . Lotus Notes 4," MIS Press, 464 pages, 1996.
Lamb, John P. et al., "Lotus Notes Network Design," McGraw-Hill, 278 pages, 1996.
Londergan, Stephen et al., "Lotus Notes® Release 4 For Dummies®," IDG Books Worldwide, 229 pages, 1996.
Lotus Development Corporation, "Firewall Security Overview And How Firewalls Relate To Lotus Notes," Lotus Notes Knowledge Base, 9 pages, May 22, 1996.
Lotus Development Corporation, "How To Set Up 'Firewall' Protection For A Notes Domain," Lotus Notes Knowledge Base, 2 pages, Nov. 6, 1995.
Lotus Development Corporation, "Lotus Announces Lotus NotesPump 1.0," Lotus Notes Knowledge Base, 6 pages, Oct. 31, 1995.
Lotus Development Corporation, "Lotus Inside Notes—The Architecture Of Notes And The Domino Server," 207 pages, 2000.
Lotus Development Corporation, "Lotus NotesPump 1.0 Q & A," Lotus Notes Knowledge Base, 3 pages, Oct. 31, 1995.
Lotus Development Corporation, "Lotus NotesPump: Database Integration For Lotus Notes," Lotus Notes Knowledge Base, 5 pages, Oct. 31, 1995.
Lotus Development Corporation, "Lotus Notes Administration," Release 3.3, 20 pages, 1995.
Lotus Development Corporation, "Lotus Notes Administrator's Guide," Release 4, 499 pages, 1995.
Lotus Development Corporation, "Lotus Notes Administrator's Guide—Server For NetWare, OS-2, And Unix," Release 3.1, 509 pages, 1994.
Lotus Development Corporation, "Lotus Notes Administrator's Guide—Server For Windows," Release 3.1, 345 pages, 1994.
Lotus Development Corporation, "Lotus Notes Application Developer's Guide," Release 4, 475 pages, 1995.
Lotus Development Corporation, "Lotus Notes Customer Service Application Guide," Release 3.1, 46 pages, 1994.
Lotus Development Corporation, "Lotus Notes Customer Support Guide," 33 pages, Published prior to Jan. 8, 2003.
Lotus Development Corporation, "Lotus Notes Customer Support Guide—North American Guide," Release 4.1, 51 pages, Published prior to Jan. 8, 2003.
Lotus Development Corporation, "Lotus Notes Database Manager's Guide," Release 4, 115 pages, 1995.

(56) References Cited

OTHER PUBLICATIONS

Lotus Development Corporation, "Lotus Notes Deployment Guide," Release 4, 104 pages, 1995.
Lotus Development Corporation, "Lotus Notes For Windows, OS-2, And Macintosh," Release 3.3, 89 pages, 1995.
Lotus Development Corporation, "Lotus Notes Getting Started With Application Development," Release 3.1, 151 pages, 1994.
Lotus Development Corporation, "Lotus Notes Install Guide For Servers," Release 4, 68 pages, 1996.
Lotus Development Corporation, "Lotus Notes Install Guide For Workstations," Release 4, 28 pages, 1995.
Lotus Development Corporation, "Lotus Notes Install Guide For Workstations," Release 4.1, 67 pages, 1996.
Lotus Development Corporation, "Lotus Notes Install Guide For Workstations," Release 4.5, 81 pages, 1996.
Lotus Development Corporation, "Lotus Notes Internet Cookbook For Notes Release 3," 21 pages, Jan. 16, 1996.
Lotus Development Corporation, "Lotus Notes Internet Cookbook For Notes Release 4," 35 pages, Feb. 14, 1996.
Lotus Development Corporation, "Lotus Notes Internotes Web Navigator Administrator's Guide," Release 4, 60 pages, 1995.
Lotus Development Corporation, "Lotus Notes Internotes Web Navigator User's Guide," Release 4, 56 pages, 1995.
Lotus Development Corporation, "Lotus Notes Internotes Web Publisher Guide," Release 4, 122 pages, 1996.
Lotus Development Corporation, "Lotus Notes LotusScript Classes For Notes," Release 4, 6 pages, Published prior to Jan. 8, 2003.
Lotus Development Corporation, "Lotus Notes Migration Guide," Release 4, 110 pages, 1996.
Lotus Development Corporation, "Lotus Notes Network Configuration Guide," Release 4.5, 121 pages, 1996.
Lotus Development Corporation, "Lotus Notes Network Driver Documentation," Release 3.1, 100 pages, 1994.
Lotus Development Corporation, "Lotus Notes Programmer's Guide—Part 1," Release 4, 614 pages, 1995.
Lotus Development Corporation, "Lotus Notes Programmer's Guide—Part 2," Release 4, 462 pages, 1995.
Lotus Development Corporation, "Lotus Notes Quick Reference For Application Developers," Release 3, 6 pages, Published prior to Jan. 8, 2003.
Lotus Development Corporation, "Lotus Notes Quick Reference For Macintosh," Release 3, 6 pages, Published prior to Jan. 8, 2003.
Lotus Development Corporation, "Lotus Notes Quick Reference For SmartIcons," Release 3.1, 4 pages, Published prior to Jan. 8, 2003.
Lotus Development Corporation, "Lotus Notes Quick Reference For Windows And Presentation Manager," Release 3, 6 pages, Published prior to Jan. 8, 2003.
Lotus Development Corporation, "Lotus Notes Release Notes," Release 4, 139 pages, 1995.
Lotus Development Corporation, "Lotus Notes Release Notes," Release 4.1, 197 pages, 1996.
Lotus Development Corporation, "Lotus Notes Server For Windows," Release 3.3, 7 pages, 1994.
Lotus Development Corporation, "Lotus Notes Server Up And Running!," Release 4, 13 pages, 1996.
Lotus Development Corporation, "Lotus Notes Site And Systems Planning Guide," Release 3.1, 169 pages, 1994.
Lotus Development Corporation, "Lotus Notes Start Here—Workstation Install For Windows, OS-2 And Macintosh," Release 3.3, 47 pages, 1995.
Lotus Development Corporation, "Lotus Notes Step By Step—A Beginner's Guide To Lotus Notes," Release 4, 179 pages, 1995.
Lotus Development Corporation, "Lotus Notes Step By Step—A Beginner's Guide To Lotus Notes," Release 4.1, 167 pages, 1996.
Lotus Development Corporation, "Lotus Software Agreement," 8 pages, Published prior to Jan. 8, 2003.
Lotus Development Corporation, "What Is The Notes Replicator?," Lotus Notes Knowledge Base, 8 pages, Jul. 5, 1995.
"Lotus Notes Advisor," Advisor Publications Inc., 55 pages, Jun. 1995.
"Lotus Notes Advisor," Advisor Publications Inc., 55 pages, Aug. 1995.
"Lotus Notes Advisor," Advisor Publications Inc., 55 pages, Oct. 1995.
"Lotus Notes Advisor," Advisor Publications Inc., 55 pages, Dec. 1995.
"Lotus Notes Advisor," Advisor Publications Inc., 63 pages, Jan.-Feb. 1996.
"Lotus Notes Advisor," Advisor Publications Inc., 55 pages, Apr. 1996.
"Lotus Notes Advisor," Advisor Publications Inc., 55 pages, Jun. 1996.
"Lotus Notes Advisor," Advisor Publications Inc., 55 pages, Aug. 1996.
"Lotus Notes Advisor," Advisor Publications Inc., 55 pages, Oct. 1996.
"Lotus Notes Advisor," Advisor Publications Inc., 63 pages, Dec. 1996.
"Lotus Notes—Notes Administration Help," Screen Shots, 17 pages, Published prior to Jan. 8, 2003.
MacGregor, Rob et al., "The Domino Defense: Security In Lotus Notes And The Internet," IBM Corporation, 183 pages, Dec. 1997.
Maltz, David A. et al., "MSOCKS: An Architecture For Transport Layer Mobility," IEEE, pp. 1037-1045, 1998.
Marmel, Elaine, "Easy Lotus® Notes Release 4.0," Que Corporation, 237 pages, 1996.
Mason, Luke, "Windows XP: New GUI Design Shows Skin Is In," TechRepublic, 4 pages, Apr. 4, 2001.
McMullen, Melanie, "Network Remote Access And Mobile Computing," Miller Freeman Inc., 226 pages, 1994.
Microsoft, Definition of "Access," Microsoft Computer Dictionary, Fifth Edition, 2 pages, May 1, 2002.
Microsoft, Definition of "Synchronization," Microsoft Computer Dictionary, Fifth Edition, 2 pages, May 1, 2002.
Milgram, Stanley, "The Small-World Problem," Psychology Today, vol. 2, pp. 60-67, 1967.
Miller, Victor S., "Use of Elliptic Curves In Cryptography," Advances in Cryptology—CRYPTO '85 Proceedings, vol. 218, pp. 417-426, 1985.
Mockapetris, P., "Domain Names—Concepts And Facilities," RFC 1034, 43 pages, Nov. 1987.
Mockapetris, P., "Domain Names—Implementation And Specification," RFC 1035, 43 pages, Nov. 1987.
Myers, Brad A. et al., "Extending The Windows Desktop Interface With Connected Handheld Computers," WSS'00 Proceedings of the 4th Conference on USENIX Windows Systems Symposium, vol. 4, 10 pages, 2000.
Myers, Brad A. et al., "User Interfaces That Span Hand-Held And Fixed Devices," CHI'2001 Workshop on Distributed and Disappearing User Interfaces in Ubiquitous Computer, 4 pages, 2001.
National Institute of Standards and Technology, "Advanced Encryption Standard (AES)," Federal Information Processing Standards Publication 197, 52 pages, Nov. 26, 2001.
National Institute of Standards and Technology, "Secure Hash Standard," Federal Information Processing Standards Publication 180-2, 83 pages, Aug. 1, 2002.
Netscape Communications Corporation, "Netscape Mail Server Administrator's Guide," Version 2.0, 172 pages, 1996.
Netscape Communications Corporation, "Netscape Mail Server Installation Guide," Version 2.0 for Unix, 62 pages, 1996.
Netscape Communications Corporation, "Netscape Mail Server User's Guide," Version 2.0, 35 pages, 1996.
Netscape Communications Corporation, "Netscape News Server Administrator's Guide For Windows NT," Version 2.0, 119 pages, 1996.
Newton, Harry, "Newton's Telecom Dictionary," 20th Edition, pp. 67, 127, 542, Mar. 2004.
Niederée, Claudia et al., "A Multi-Dimensional, Unified User Model For Cross-System Personalization," Proceedings of the AVI 2004 Workshop on Environments for Personalized Information Access, 11 pages, 2004.
Nokia, "Developer Platforms," 3 pages, 2005.

(56) References Cited

OTHER PUBLICATIONS

"NotesPump 1.0 Release Notes," Publication Unknown, 8 pages, Published prior to Jan. 8, 2003.
Opyt, Barbara et al., "Use The Internet As Your Lotus Notes WAN," Lotus Notes Advisor, pp. 17-20, Nov.-Dec. 1996.
Ortiz, C. Enrique, "An Introduction To The Symbian OS™ Platform For Palm OS® Developers," Metrowerks Corp., 21 pages, 2002.
"Overview—What Is Lotus NotesPump?," Publication Unknown, 88 pages, Published prior to Jan. 8, 2003.
Perez, Sarah, "Onavo's Data-Compressing Mobile App Raises $10 Million Series B From Horizons, Motorola Ventures," 2 pages, Jan. 24, 2012.
Phillips, Joshua et al., "Modeling The Intelligence Analysis Process For Intelligent User Agent Development," Research and Practice in Human Resource Management, vol. 9, No. 1, pp. 59-73, 2001.
Pyle, Hugh, "The Architecture Of Lotus Notes," Lotus Notes Advisor, Premiere Issue, pp. 18-27, 1995.
Pyle, Lisa, "A Jump Start To The Top Ten R3-To-R4 Migration Considerations," The View, vol. 1, Issue 5, 22 pages, Nov.-Dec. 1995.
Qualcomm Incorporated, "Managing Background Data Traffic In Mobile Devices," 16 pages, Jan. 2012.
Qualcomm, "System Parameter Recommendations To Optimize PS Data User Experience And UE Battery Life," 80-W1112-1, Revision B, 9 pages, Mar. 2007.
Ringel, Meredith et al., "iStuff: A Scalable Architecture For Lightweight, Wireless Devices For Ubicomp User Interfaces," Proceedings of UbiComp 2002, 2 pages, 2002.
Seven Networks, Inc., "Seven Optimizing The Mobile Ecosystem," www.seven.com/products.traffic_optimization.php, 1 page, May 29, 2012.
Shafran, Andrew Bryce, "Easy Lotus Notes® For Windows™," Que Corporation, 199 pages, 1994.
Signorini, Eugene, "Seven's Service-Based Wireless Solutions Enable Enterprises To Untether E-Mail," Wireless/Mobile Enterprise & Commerce, 16 pages, Oct. 2004.
Swedeen, Bret et al., "Under The Microscope—Domino Replication," LDD Today, 8 pages, Oct. 1, 1998.
Tamura, Randall A., "Lotus® Notes™ 4 Unleashed," Sams Publishing, 928 pages, 1996.
U.S. Appl. No. 60/663,463, File History, 113 pages, Mar. 18, 2005.
Vivacqua, Adriana et al., "Profiling And Matchmaking Strategies In Support Of Opportunistic Collaboration," CoopIS/DOA/ODBASE 2003, LNCS 2888, pp. 162-177, 2003.
Wainwright, Andrew, "Secrets To Running Lotus Notes: The Decisions No One Tells You How To Make," IBM Corporation, 193 pages, Oct. 1996.
Wikipedia, Definition for "General Packet Radio Service," 7 pages, downloaded on May 31, 2012.
Wilcox, Adam A., "PC Learning Labs Teaches Lotus Notes 3.0," Ziff-Davis Press, 381 pages, 1993.
Wong, Harry, "Casahl's Replic-Action: Delivering True Notes-DBMS Integration," The View, vol. 2, Issue 1, pp. 33-50, Jan.-Feb. 1996.

\* cited by examiner

| Mobile Application/Widget 455 | Local Proxy 465 | Host server 485<br>Server Cache 435 or Caching Proxy 475 | Application Server/<br>Content Provider 495 |
|---|---|---|---|
| Polls application server/provider 432 | Poll intercepted 434 | | |
| | Proxy detects that cache content is available for the polled content and is valid and thus retrieves a response to satisfy the poll 436 | | |
| Receives a response to the poll from a cache entry 438 | | | |
| Polls application server/provider 440 | Poll intercepted 442 | | |
| | Proxy detects that cache content is unavailable and decides to setup the polled source for caching 444 | | |
| | Poll request forwarded to the source 446 | | Receives the poll request from the application and provides a response to satisfy the current request 448 |
| Receives the response to satisfy the request from the application server/provider 450 | | | |
| | Tracks polling frequency of the application and sets up a polling schedule to the host server 452 | | |
| | Sends the cache setup to the host server 454 | Receives the cache setup including an identification of the application server/provider to be polled and a polling schedule 456 | |
| | | Polls the Application server/provider to monitor the response to the request 458 | Receives poll from host server and sends the response 460 |
| | | Same response received, pulls the application based on the polling schedule 462 | Receives poll from host server and sends the response 464 |
| | | Detects changed or new response; notifies the local proxy 466 | |
| | | Changed or new response stored in the server cache or the caching proxy 468 | |
| | Receives notification that new or changed data is available; invalidates relevant cache entries 470 | | |
| Polls application server/content provider 472 | Determines that no valid cache entry is available and retrieves the response from the server cache 474 | Receives request for the new response and sends the response to the local proxy 476 | |
| Request satisfied from the server cache or caching proxy 478 | | | |
| Polls application server/content provider 480 | Determines that no valid cache entry is available and forwards the poll to the application server/provider 482 | | Receives poll from and sends the response 484 |
| Request satisfied from the application server/provider 486 | | | |

*FIG. 4B*

APPLICATION AND NETWORK-BASED LONG POLL REQUEST DETECTION AND CACHEABILITY ASSESSMENT THEREFOR

CROSS-REFERENCE TO RELATED APPLICATIONS

This application is a continuation of U.S. application Ser. No. 13/412,338 entitled "APPLICATION AND NETWORK-BASED LONG POLL REQUEST DETECTION AND CACHEABILITY ASSESSMENT THEREFOR," filed Mar. 5, 2012, now U.S. Pat. No. 8,291,076 issued on Oct. 16, 2012, which is a continuation of U.S. application Ser. No. 13/274,248 entitled "APPLICATION AND NETWORK-BASED LONG POLL REQUEST DETECTION AND CACHEABILITY ASSESSMENT THEREFOR," filed on Oct. 14, 2011, now U.S. Pat. No. 8,166,164 issued on Apr. 24, 2012, which claims benefit of U.S. Provisional Patent Application No. 61/408,858 entitled "CROSS APPLICATION TRAFFIC COORDINATION", which was filed on Nov. 1, 2010, U.S. Provisional Patent Application No. 61/408,839 entitled "ACTIVITY SESSION AS METHOD OF OPTIMIZING NETWORK RESOURCE USE", which was filed on Nov. 1, 2010, U.S. Provisional Patent Application No. 61/408,829 entitled "DISTRIBUTED POLICY MANAGEMENT", which was filed on Nov. 1, 2010, U.S. Provisional Patent Application No. 61/408,846 entitled "INTELLIGENT CACHE MANAGEMENT IN CONGESTED WIRELESS NETWORKS", which was filed on Nov. 1, 2010, U.S. Provisional Patent Application No. 61/408,854 entitled "INTELLIGENT MANAGEMENT OF NON-CACHEABLE CONTENT IN WIRELESS NETWORKS", which was filed on Nov. 1, 2010, U.S. Provisional Patent Application No. 61/408,826 entitled "ONE WAY INTELLIGENT HEARTBEAT", which was filed on Nov. 1, 2010, U.S. Provisional Patent Application No. 61/408,820 entitled "TRAFFIC CATEGORIZATION AND POLICY DRIVING RADIO STATE", which was filed on Nov. 1, 2010, U.S. Provisional Patent Application No. 61/416,020 entitled "ALIGNING BURSTS FROM SERVER TO CLIENT", which was filed on Nov. 22, 2010, U.S. Provisional Patent Application No. 61/416,033 entitled "POLLING INTERVAL FUNCTIONS", which was filed on Nov. 22, 2010, U.S. Provisional Patent Application No. 61/430,828 entitled "DOMAIN NAME SYSTEM WITH NETWORK TRAFFIC HARMONIZATION", which was filed on Jan. 7, 2011, U.S. Provisional Patent Application No. 61/532,857 entitled "CACHE DEFEAT DETECTION AND CACHING OF CONTENT ADDRESSED BY IDENTIFIERS INTENDED TO DEFEAT CACHE", which was filed on Sep. 9, 2011, U.S. Provisional Patent Application No. 61/533,007 entitled "DISTRIBUTED CACHING IN A WIRELESS NETWORK OF CONTENT DELIVERED FOR A MOBILE APPLICATION OVER A LONG-HELD REQUEST", which was filed on Sep. 9, 2011, and U.S. Provisional Patent Application No. 61/533,021 entitled "APPLICATION AND NETWORK-BASED LONG POLL REQUEST DETECTION AND CACHEABILITY ASSESSMENT THEREFOR", which was filed on Sep. 9, 2011, the contents of which are all incorporated by reference herein.

This application is related to U.S. patent application Ser. No. 13/176,537 entitled "DISTRIBUTED CACHING AND RESOURCE AND MOBILE NETWORK TRAFFIC MANAGEMENT," which was filed on Jul. 5, 2011, the contents of which are herein incorporated by reference.

This application is related to U.S. patent application Ser. No. 13/274,250 entitled "Distributed Caching In A Wireless Network Of Content Delivered For A Mobile Application Over A Long-Held Request", filed Oct. 14, 2011, and the contents of which are herein incorporated by reference.

This application is related to U.S. patent application Ser. No. 13/274,265 entitled "Caching Adapted for Mobile Application Behavior and Network Conditions," filed Oct. 14, 2011, and the contents of which are herein incorporated by reference.

This application is related to U.S. patent application Ser. No. 13/274,501 entitled "Request and Response Characteristics based Adaptation of Distributed Caching In A Mobile Network", filed Oct. 17, 2011, and the contents of which are herein incorporated by reference.

BACKGROUND

The mobile application model has significantly changed consumption of content managed on the Internet. For example, joining social media and instant messaging applications, increasingly popular mobile gaming applications such as Angry Birds, are some of the latest types of applications to send mobile signaling and data consumption skyrocketing. Angry Birds is just one example of the many available applications that constantly signal the mobile network for updates at hundreds and even thousands of times per hour. As such, traditional practices of providing all-you-can-eat data plans have become a thing of the past. The data tsunami is affecting the mobile ecosystem as a whole, and end-users are feeling the brunt of the wrath as operators scramble to find the best solution.

The applications that contribute to mobile data consumption can further include, for example, push email, instant messaging, visual voicemail, voice and video telephony, and others which may require an always-on of frequent IP connections and frequent transmit of small bits of data. Further, these applications poll their host servers with varying polling characteristics, due to the nature of the application, user activity, and/or nature of data being exchanged. For example, one category of polling can be represented by a persistent IP connection, such as one established by long polling or COMET style push, which is a web application model where long-held request (e.g., long-held HTTP requests) allows server to push data to the client when this data becomes available.

The persistent connection allows emulation of content push from server to client (e.g., mobile client). Specifically, when a response is not available when the request is sent, the server holds the request until information becomes available to be sent to the client. In general, the client immediately re-issues a request to the server, which the server then responds to or holds until a response is available. This behavior of long polls or other types of persistent connections is different from other types of polling. Due to the different caching requirements of different types of polling, different classes of polling patterns, such as long poll patterns and characteristics need to be detected for effective caching and assessment of cacheability.

BRIEF DESCRIPTION OF THE DRAWINGS

FIG. 4B depicts an interaction diagram showing how application polls having data requests from a mobile device (e.g., any wireless device) to an application server/content provider in a wireless network (or broadband network) can be can be cached on the local proxy and managed by the distributed caching system.

DETAILED DESCRIPTION

Figure 1A:
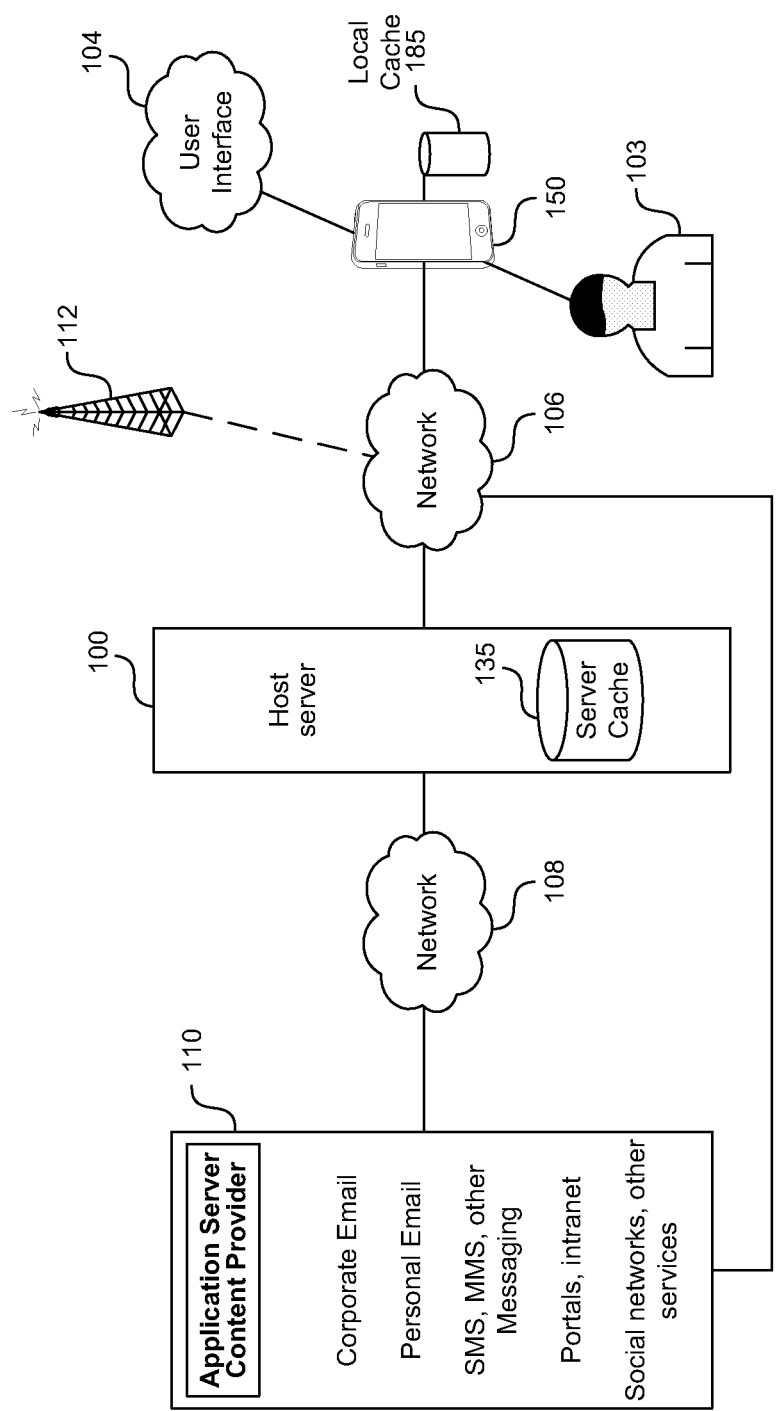
FIG. 1A illustrates an example diagram of a system where a host server facilitates management of traffic, content caching, and/or resource conservation between mobile devices (e.g., wireless devices) and an application server or content provider in a wireless network (or broadband network) for resource conservation.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way.

Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions will control.

Embodiments of the present disclosure include systems and methods for application and network-based long poll request detection and cacheability assessment therefor.

For example, a long poll request initiated at a mobile device can be detected by determining relative timings between a first request initiated by the application, a response received responsive to the first request, and a second request initiated subsequent to the first request also by the application. The relative timings can be used to determine whether requests generated by the application are long poll requests. Furthermore, using the relative timings and received responsive to the requests generated by the application, it can be determined that content received for the application is cacheable, when the received responses indicate repeatability, and/or when the relative timings depict some pattern that may be reproducible.

A long-held request generally includes and can refer to, connections between a client (e.g., an application, a mobile application on a device, or a device such as a mobile device or wireless device) and a server that is held open even if content is not available to be sent back to the client. The connection can be maintained between the client and server, until content becomes available at the server to be sent to the client. In general, once a response with content is sent back to the client (e.g., end user computer or mobile device such as a mobile phone, or a Machine to Machine (M2M) device)) the connection terminates (e.g., terminated by the server). The client typically will immediately re-issue a request to connect again to the server which holds the connection open until requested content becomes available for the client device.

A long-held requested connection can include, for example, a persistent connection, a persistent HTTP connection, long poll-type request, HTTP streaming, or any other types of connections suited for push or emulated content push.

One embodiment of the disclosed technology includes, a system that optimizes multiple aspects of the connection with wired and wireless networks, broadband networks, and devices through a comprehensive view of device and application activity including: loading, current application needs on a device, controlling the type of access (push vs. pull or hybrid), location, concentration of users in a single area, time of day, how often the user interacts with the application, content or device, and using this information to shape traffic to a cooperative client/server or simultaneously mobile devices without a cooperative client. Because the disclosed server is not tied to any specific network provider it has visibility into the network performance across all service providers. This enables optimizations to be applied to devices regardless of the operator or service provider, thereby enhancing the user experience and managing network utilization while roaming. Bandwidth has been considered a major issue in wireless networks today. More and more research has been done related to the need for additional bandwidth to solve access problems—many of the performance enhancing solutions and next generation standards, such as those commonly referred to as 4G, namely LTE, 4G, and WiMAX are focused on providing increased bandwidth. Although partially addressed by the standards a key problem that remains is lack of bandwidth on the signaling channel more so than the data channel and the standard does not address battery life very well.

Embodiments of the disclosed technology includes, for example, alignment of requests from multiple applications to minimize the need for several polling requests; leverage specific content types to determine how to proxy/manage a connection/content; and apply specific heuristics associated with device, user behavioral patterns (how often they interact with the device/application) and/or network parameters.

Embodiments of the present technology can further include, moving recurring HTTP polls performed by various widgets, RSS readers, etc., to remote network node (e.g., Network Operation Center (NOC)), thus considerably lowering device battery/power consumption, radio channel signaling and bandwidth usage. Additionally, the offloading can be performed transparently so that existing applications do not need to be changed.

In some embodiments, this can be implemented using a local proxy on the mobile device (e.g., any wireless device) which automatically detects recurring requests for the same content (RSS feed, Widget data set) that matches a specific rule (e.g., happens every 15 minutes). The local proxy can automatically cache the content on the mobile device while delegating the polling to the server (e.g., a proxy server operated as an element of a communications network). The server can then notify the mobile/client proxy if the content changes, and if content has not changed (or not changed sufficiently, or in an identified manner or amount) the mobile proxy provides the latest version in its cache to the user (without need to utilize the radio at all). This way the mobile or wireless device (e.g., a mobile phone, smart phone, M2M module/MODEM, or any other wireless devices, etc.) does not need to open (e.g., thus powering on the radio) or use a data connection if the request is for content that is monitored and that has been not flagged as new/changed.

The logic for automatically adding content sources/application servers (e.g., including URLs/content) to be monitored can also check for various factors like how often the content is the same, how often the same request is made (is there a fixed interval/pattern?), which application is requesting the data, etc. Similar rules to decide between using the cache and request the data from the original source may also be implemented and executed by the local proxy and/or server.

For example, when the request comes at an unscheduled/unexpected time (user initiated check), or after every (n) consecutive times the response has been provided from the cache, etc., or if the application is running in the background vs. in a more interactive mode of the foreground. As more and more mobile applications or wireless enabled applications base their features on resources available in the network, this becomes increasingly important. In addition, the disclosed technology allows elimination of unnecessary chatter from the network, benefiting the operators trying to optimize the wireless spectrum usage.

Intelligent Cache Management

By detecting the rate and type of requests to a content source or application server (which may be identified by a URI or URL), combined with determining the state information of the mobile device (e.g., whether the backlight is on or off) or the user, the distributed proxy system (e.g., the local proxy and/or the proxy server) can, for example, determine the difference between content that is programmatically refreshed and content that is requested by the user in the foreground. Using this information, along with the network conditions such as the TCP connection delay and/or Round Trip Time (RTT), current radio coverage statistics, the disclosed proxy system can determine whether to and when to cache content locally on the mobile device (e.g., any wireless device), to satisfy future content requests. If content is already cached, then the cached version can be presented to the user. If not, the request is passed through over the mobile network to the content server and the retrieved content can be presented.

To preserve user experience, the disclosed distributed proxy system can determine and utilize the "criticality of an application" as a factor. For example, financial applications may be considered time critical so that these application requests are not cached but instead allowed to go over the wireless broadband or mobile network to retrieve current data. An application, by name or type, can be considered critical at the time of provisioning or determined by programmatic observation of user interaction over time. That is, the sever-side component of the distributed proxy system can be provisioned with "profiles" which indicate the criticality of the application. This profile can be communicated to the device-side component of the proxy system during initialization or subsequent establishment of polling requests.

A set of criteria (e.g., including application profile information) can be applied to content sources/application servers (e.g., each associated resource or resource identifier) to determine the suitability of related content for caching (size, etc.). The profile can further be used to identify applications for which caching will typically not be appropriate, such as the Google Market. Additionally, the pattern (e.g., periodicity or time interval) of each request as identified by a specific identifier (e.g., a resource of resource identifier) associated with a content source/application server can be monitored by the distributed system such that polling behavior can be determined, and the content cached accordingly.

When content from a content source/application server has been identified as suitable for caching, a message can be transmitted to the server-side component of the disclosed proxy system requesting that that the content associated with the content source/application server be monitored for changes. When the server detects that the content has been altered, the server transmits a message to the device-side component instructing it to invalidate whatever cache elements are associated with that URI.

In some instances, memory usage parameters of a mobile device (e.g., as described by the carrier configuration) are factored in when caching. As such, the client-side component of the disclosed distributed proxy will usually not use more than the specified percentage of available memory space for cache entries (e.g., as specified by the device manufacturer, operating system, applications, etc.). In addition to total memory usage, the client-side component of the distributed proxy can implement a configurable limit on the total number of cache entries stored across multiple applications or on a per-application basis.

Cache entries stored on the mobile device (e.g., any wireless device) can be aged out automatically by the client-side component of the distributed proxy as determined, for example, by configurable parameters (e.g., by the user, based on application-need, network service provider requirements, OS requirements, etc.). Additionally, cache elements may be removed to remain in compliance with disk usage or entry count restrictions. In some instances, the client-side component can invalidate the entire cache storage should the server-side proxy become unavailable. In one embodiment, the client-side component of the distributed proxy system can encrypt cached content.

FIG. 1A illustrates an example diagram of a system where a host server 100 facilitates management of traffic, content caching, and/or resource conservation between clients (e.g., mobile devices, any wireless device or clients/applications on client devices 150) and an application server or content provider 110 in a wireless network (or broad band network) 106 or 108 for resource conservation.

The client devices 150 can be any system and/or device, and/or any combination of devices/systems that is able to establish a connection, including wired, wireless, cellular connections with another device, a server and/or other systems such as host server 100 and/or application server/content provider 110. Client devices 150 will typically include a display and/or other output functionalities to present information and data exchanged between among the devices 150 and/or the host server 100 and/or application server/content provider 110.

For example, the client devices 150 can include mobile, hand held or portable devices, wireless devices, or non-portable devices and can be any of, but not limited to, a server desktop, a desktop computer, a computer cluster, or portable devices, including a notebook, a laptop computer, a handheld computer, a palmtop computer, a mobile phone, a cell phone, a smart phone, a PDA, a Blackberry device, a Palm device, a handheld tablet (e.g., an iPad or any other tablet), a hand held console, a hand held gaming device or console, any SuperPhone such as the iPhone, and/or any other portable, mobile, hand held devices, or fixed wireless interface such as a M2M device, etc. In one embodiment, the client devices 150, host server 100, and application server 110 are coupled via a network 106 and/or a network 108. In some embodiments, the devices 150 and host server 100 may be directly connected to one another.

The input mechanism on client devices 150 can include touch screen keypad (including single touch, multi-touch, gesture sensing in 2D or 3D, etc.), a physical keypad, a mouse, a pointer, a track pad, motion detector (e.g., including 1-axis, 2-axis, 3-axis accelerometer, etc.), a light sensor, capacitance sensor, resistance sensor, temperature sensor, proximity sensor, a piezoelectric device, device orientation detector (e.g., electronic compass, tilt sensor, rotation sensor, gyroscope, accelerometer), or a combination of the above.

Signals received or detected indicating user activity at client devices 150 through one or more of the above input mechanism, or others, can be used in the disclosed technology in acquiring context awareness at the client device 150. Context awareness at client devices 150 generally includes, by way of example but not limitation, client device 150 operation or state acknowledgement, management, user activity/behavior/interaction awareness, detection, sensing, tracking, trending, and/or application (e.g., mobile applications) type, behavior, activity, operating state, etc.

Context awareness in the present disclosure also includes knowledge and detection of network side contextual data and can include network information such as network capacity, bandwidth, traffic, type of network/connectivity, and/or any other operational state data. Network side contextual data can be received from and/or queried from network service providers (e.g., cell provider 112 and/or Internet service providers) of the network 106 and/or network 108 (e.g., by the host server and/or devices 150). In addition to application context awareness as determined from the client 150 side, the application context awareness may also be received from or obtained/queried from the respective application/service providers 110 (by the host 100 and/or client devices 150).

The host server 100 can use, for example, contextual information obtained for client devices 150, networks 106/108, applications (e.g., mobile applications), application server/provider 110, or any combination of the above, to manage the traffic in the system to satisfy data needs of the client devices 150 (e.g., to satisfy application or any other request including HTTP request). In one embodiment, the traffic is managed by the host server 100 to satisfy data requests made in response to explicit or non-explicit user 103 requests and/or device/application maintenance tasks. The traffic can be managed such that network consumption, for example, use of the cellular network is conserved for effective and efficient bandwidth utilization. In addition, the host server 100 can manage and coordinate such traffic in the system such that use of device 150 side resources (e.g., including but not limited to battery power consumption, radio use, processor/memory use) are optimized with a general philosophy for resource conservation while still optimizing performance and user experience.

For example, in context of battery conservation, the device 150 can observe user activity (for example, by observing user keystrokes, backlight status, or other signals via one or more input mechanisms, etc.) and alters device 150 behaviors. The device 150 can also request the host server 100 to alter the behavior for network resource consumption based on user activity or behavior.

In one embodiment, the traffic management for resource conservation is performed using a distributed system between the host server 100 and client device 150. The distributed system can include proxy server and cache components on the server side 100 and on the device/client side, for example, as shown by the server cache 135 on the server 100 side and the local cache 185 on the client 150 side.

Functions and techniques disclosed for context aware traffic management for resource conservation in networks (e.g., network 106 and/or 108) and devices 150, reside in a distributed proxy and cache system. The proxy and cache system can be distributed between, and reside on, a given client device 150 in part or in whole and/or host server 100 in part or in whole. The distributed proxy and cache system are illustrated with further reference to the example diagram shown in FIG. 1B. Functions and techniques performed by the proxy and cache components in the client device 150, the host server 100, and the related components therein are described, respectively, in detail with further reference to the examples of FIG. 2-3.

In one embodiment, client devices 150 communicate with the host server 100 and/or the application server 110 over network 106, which can be a cellular network and/or a broadband network. To facilitate overall traffic management between devices 150 and various application servers/content providers 110 to implement network (bandwidth utilization) and device resource (e.g., battery consumption), the host server 100 can communicate with the application server/providers 110 over the network 108, which can include the Internet (e.g., a broadband network).

In general, the networks 106 and/or 108, over which the client devices 150, the host server 100, and/or application server 110 communicate, may be a cellular network, a broadband network, a telephonic network, an open network, such as the Internet, or a private network, such as an intranet and/or the extranet, or any combination thereof. For example, the Internet can provide file transfer, remote log in, email, news, RSS, cloud-based services, instant messaging, visual voicemail, push mail, VoIP, and other services through any known or convenient protocol, such as, but is not limited to the TCP/IP protocol, UDP, HTTP, DNS, FTP, UPnP, NSF, ISDN, PDH, RS-232, SDH, SONET, etc.

The networks 106 and/or 108 can be any collection of distinct networks operating wholly or partially in conjunction to provide connectivity to the client devices 150 and the host server 100 and may appear as one or more networks to the serviced systems and devices.

In one embodiment, communications to and from the client devices 150 can be achieved by, an open network, such as the Internet, or a private network, broadband network, such as an intranet and/or the extranet. In one embodiment, communications can be achieved by a secure communications protocol, such as secure sockets layer (SSL), or transport layer security (TLS).

In addition, communications can be achieved via one or more networks, such as, but are not limited to, one or more of WiMax, a Local Area Network (LAN), Wireless Local Area Network (WLAN), a Personal area network (PAN), a Campus area network (CAN), a Metropolitan area network (MAN), a Wide area network (WAN), a Wireless wide area network (WWAN), or any broadband network, and further enabled with technologies such as, by way of example, Global System for Mobile Communications (GSM), Personal Communications Service (PCS), Bluetooth, WiFi, Fixed Wireless Data, 2G, 2.5G, 3G, 4G, IMT-Advanced, pre-4G, LTE Advanced, mobile WiMax, WiMax 2, WirelessMAN-Advanced networks, enhanced data rates for GSM evolution (EDGE), General packet radio service (GPRS), enhanced GPRS, iBurst, UMTS, HSPDA, HSUPA, HSPA, UMTS-TDD, 1xRTT, EV-DO, messaging protocols such as, TCP/IP, SMS, MMS, extensible messaging and presence protocol (XMPP), real time messaging protocol (RTMP), instant messaging and presence protocol (IMPP), instant messaging, USSD, IRC, or any other wireless data networks, broadband networks, or messaging protocols.

Figure 1B:
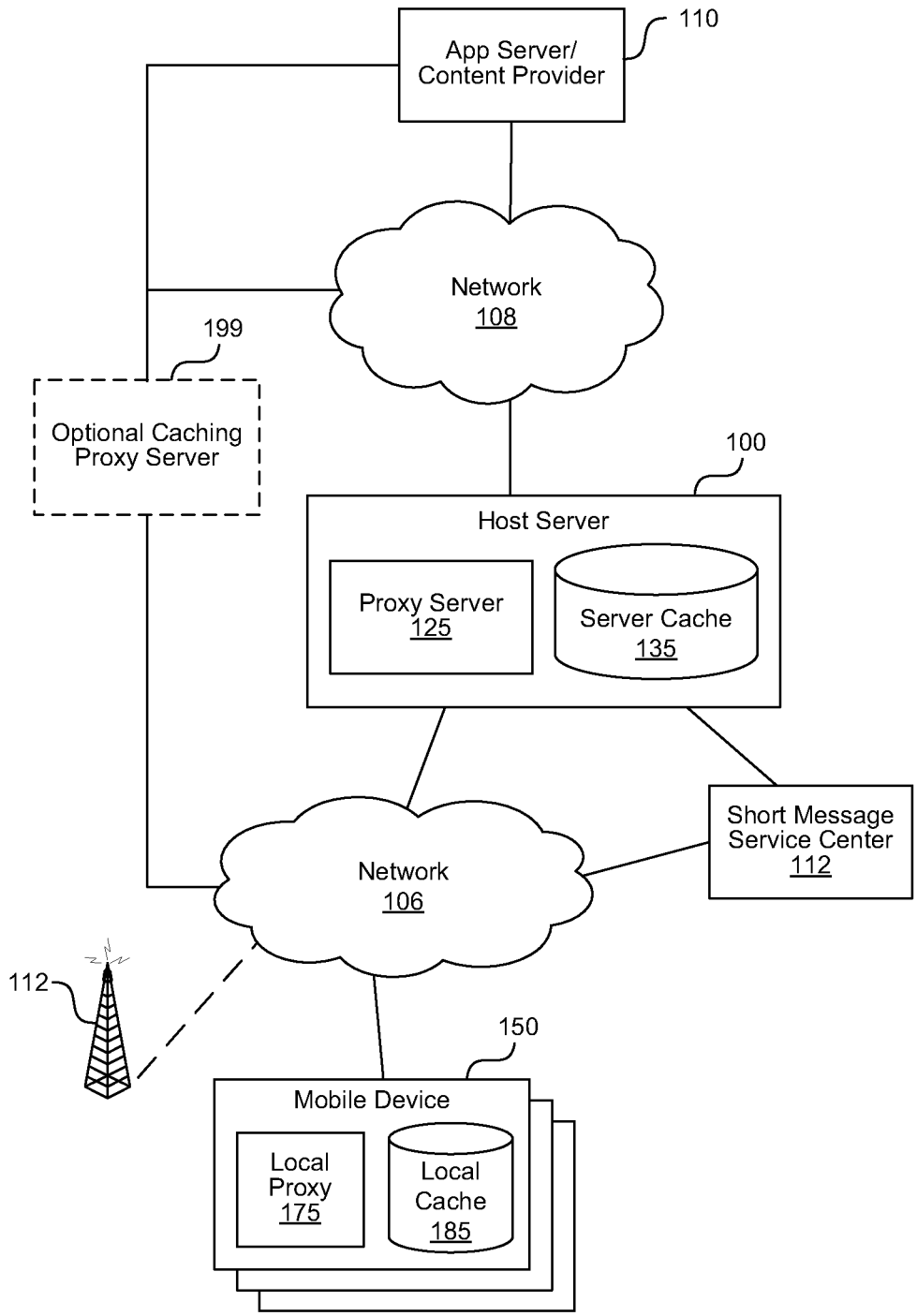
FIG. 1B illustrates an example diagram of a proxy and cache system distributed between the host server and device which facilitates network traffic management between a device and an application server/content provider for resource conservation and content caching.

FIG. 1B illustrates an example diagram of a proxy and cache system distributed between the host server 100 and device 150 which facilitates network traffic management between the device 150 and an application server/content provider 100 (e.g., a source server) for resource conservation and content caching.

The distributed proxy and cache system can include, for example, the proxy server 125 (e.g., remote proxy) and the server cache, 135 components on the server side. The server-side proxy 125 and cache 135 can, as illustrated, reside internal to the host server 100. In addition, the proxy server 125 and cache 135 on the server-side can be partially or wholly external to the host server 100 and in communication via one or more of the networks 106 and 108. For example, the proxy server 125 may be external to the host server and the server cache 135 may be maintained at the host server 100. Alternatively, the proxy server 125 may be within the host server 100 while the server cache is external to the host server 100. In addition, each of the proxy server 125 and the cache 135 may be partially internal to the host server 100 and partially external to the host server 100.

The distributed system can also, include, in one embodiment, client-side components, including by way of example but not limitation, a local proxy 175 (e.g., a mobile client on a mobile device) and/or a local cache 185, which can, as illustrated, reside internal to the device 150 (e.g., a mobile device).

In addition, the client-side proxy 175 and local cache 185 can be partially or wholly external to the device 150 and in communication via one or more of the networks 106 and 108. For example, the local proxy 175 may be external to the device 150 and the local cache 185 may be maintained at the device 150. Alternatively, the local proxy 175 may be within the device 150 while the local cache 185 is external to the device 150. In addition, each of the proxy 175 and the cache 185 may be partially internal to the host server 100 and partially external to the host server 100.

In one embodiment, the distributed system can include an optional caching proxy server 199. The caching proxy server 199 can be a component which is operated by the application server/content provider 110, the host server 100, or a network service provider 112, and or any combination of the above to facilitate network traffic management for network and device resource conservation. Proxy server 199 can be used, for example, for caching content to be provided to the device 150, for example, from one or more of, the application server/provider 110, host server 100, and/or a network service provider 112. Content caching can also be entirely or partially performed by the remote proxy 125 to satisfy application requests or other data requests at the device 150.

In context aware traffic management and optimization for resource conservation in a network (e.g., cellular or other wireless networks), characteristics of user activity/behavior and/or application behavior at a mobile device (e.g., any wireless device) 150 can be tracked by the local proxy 175 and communicated, over the network 106 to the proxy server 125 component in the host server 100, for example, as connection metadata. The proxy server 125 which in turn is coupled to the application server/provider 110 provides content and data to satisfy requests made at the device 150.

In addition, the local proxy 175 can identify and retrieve mobile device properties, including one or more of, battery level, network that the device is registered on, radio state, or whether the mobile device is being used (e.g., interacted with by a user). In some instances, the local proxy 175 can delay, expedite (prefetch), and/or modify data prior to transmission to the proxy server 125, when appropriate, as will be further detailed with references to the description associated with the examples of FIG. 2-3.

The local database 185 can be included in the local proxy 175 or coupled to the local proxy 175 and can be queried for a locally stored response to the data request prior to the data request being forwarded on to the proxy server 125. Locally cached responses can be used by the local proxy 175 to satisfy certain application requests of the mobile device 150, by retrieving cached content stored in the cache storage 185, when the cached content is still valid.

Similarly, the proxy server 125 of the host server 100 can also delay, expedite, or modify data from the local proxy prior to transmission to the content sources (e.g., the application server/content provider 110). In addition, the proxy server 125 uses device properties and connection metadata to generate rules for satisfying request of applications on the mobile device 150. The proxy server 125 can gather real time traffic information about requests of applications for later use in optimizing similar connections with the mobile device 150 or other mobile devices.

In general, the local proxy 175 and the proxy server 125 are transparent to the multiple applications executing on the mobile device. The local proxy 175 is generally transparent to the operating system or platform of the mobile device and may or may not be specific to device manufacturers. In some instances, the local proxy 175 is optionally customizable in part or in whole to be device specific. In some embodiments, the local proxy 175 may be bundled into a wireless model, a firewall, and/or a router.

In one embodiment, the host server 100 can in some instances, utilize the store and forward functions of a short message service center (SMSC) 112, such as that provided by the network service provider, in communicating with the device 150 in achieving network traffic management. Note that 112 can also utilize any other type of alternative channel including USSD or other network control mechanisms. As will be further described with reference to the example of FIG. 3, the host server 100 can forward content or HTTP responses to the SMSC 112 such that it is automatically forwarded to the device 150 if available, and for subsequent forwarding if the device 150 is not currently available.

In general, the disclosed distributed proxy and cache system allows optimization of network usage, for example, by serving requests from the local cache 185, the local proxy 175 reduces the number of requests that need to be satisfied over the network 106. Further, the local proxy 175 and the proxy server 125 may filter irrelevant data from the communicated data. In addition, the local proxy 175 and the proxy server 125 can also accumulate low priority data and send it in batches to avoid the protocol overhead of sending individual data fragments. The local proxy 175 and the proxy server 125 can also compress or transcode the traffic, reducing the amount of data sent over the network 106 and/or 108. The signaling traffic in the network 106 and/or 108 can be reduced, as the networks are now used less often and the network traffic can be synchronized among individual applications.

With respect to the battery life of the mobile device 150, by serving application or content requests from the local cache 185, the local proxy 175 can reduce the number of times the radio module is powered up. The local proxy 175 and the proxy server 125 can work in conjunction to accumulate low priority data and send it in batches to reduce the number of times and/or amount of time when the radio is powered up. The local proxy 175 can synchronize the network use by performing the batched data transfer for all connections simultaneously.

Figure 2A:
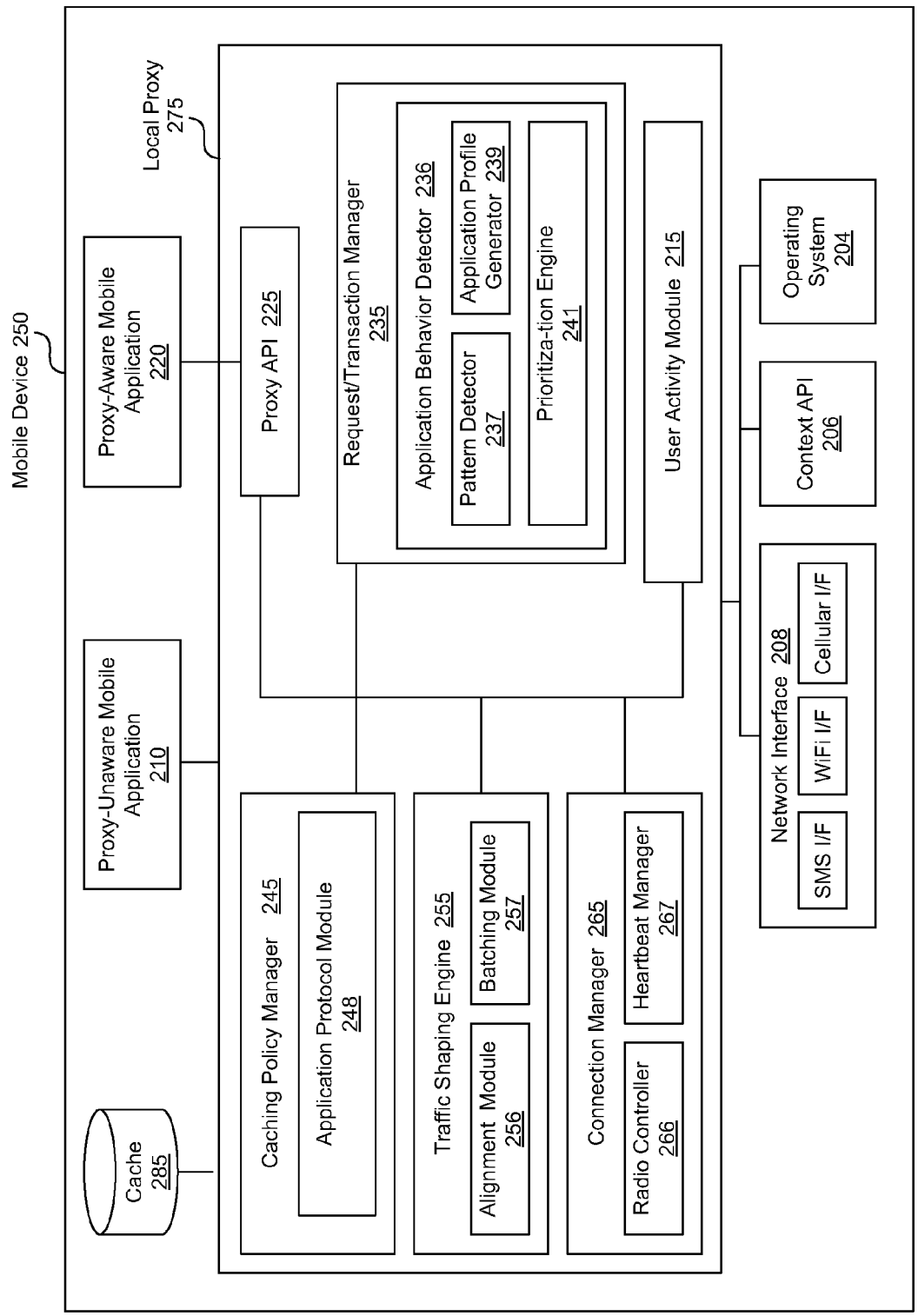
FIG. 2A depicts a block diagram illustrating an example of client-side components in a distributed proxy and cache system residing on a mobile device (e.g., wireless device) that manages traffic in a wireless network (or broadband network) for resource conservation, content caching, and/or traffic management.

FIG. 2A depicts a block diagram illustrating an example of client-side components in a distributed proxy and cache system residing on a device 250 that manages traffic in a wireless network for resource conservation, content caching, and/or traffic management.

The device 250, which can be a portable or mobile device (e.g., any wireless device), such as a portable phone, generally includes, for example, a network interface 208208 an operating system 204, a context API 206, and mobile applications which may be proxy-unaware 210 or proxy-aware 220. Note that the device 250 is specifically illustrated in the example of FIG. 2 as a mobile device, such is not a limitation and that device 250 may be any portable/mobile or non-portable device able to receive, transmit signals to satisfy data requests over a network including wired or wireless networks (e.g., WiFi, cellular, Bluetooth, etc.).

The network interface 208 can be a networking module that enables the device 250 to mediate data in a network with an entity that is external to the host server 250, through any known and/or convenient communications protocol supported by the host and the external entity. The network interface 208 can include one or more of a network adaptor card, a wireless network interface card (e.g., SMS interface, WiFi interface, interfaces for various generations of mobile communication standards including but not limited to 2G, 3G, 3.5G, 4G, LTE, etc.), Bluetooth, or whether or not the connection is via a router, an access point, a wireless router, a switch, a multilayer switch, a protocol converter, a gateway, a bridge, a bridge router, a hub, a digital media receiver, and/or a repeater.

Device 250 can further include, client-side components of the distributed proxy and cache system which can include, a local proxy 275 (e.g., a mobile client of a mobile device) and a cache 285. In one embodiment, the local proxy 275 includes a user activity module 215, a proxy API 225, a request/transaction manager 235, a caching policy manager 245 having an application protocol module 248, a traffic shaping engine 255, and/or a connection manager 265. The traffic shaping engine 255 may further include an alignment module 256 and/or a batching module 257, the connection manager 265 may further include a radio controller 266. The request/transaction manager 235 can further include an application behavior detector 236 and/or a prioritization engine 241, the application behavior detector 236 may further include a pattern detector 237 and/or and application profile generator 239. Additional or less components/modules/engines can be included in the local proxy 275 and each illustrated component.

As used herein, a "module," "a manager," a "handler," a "detector," an "interface," a "controller," a "normalizer," a "generator," an "invalidator," or an "engine" includes a general purpose, dedicated or shared processor and, typically, firmware or software modules that are executed by the processor. Depending upon implementation-specific or other considerations, the module, manager, handler, detector, interface, controller, normalizer, generator, invalidator, or engine can be centralized or its functionality distributed. The module, manager, handler, detector, interface, controller, normalizer, generator, invalidator, or engine can include general or special purpose hardware, firmware, or software embodied in a computer-readable (storage) medium for execution by the processor.

As used herein, a computer-readable medium or computer-readable storage medium is intended to include all mediums that are statutory (e.g., in the United States, under 35 U.S.C. 101), and to specifically exclude all mediums that are non-statutory in nature to the extent that the exclusion is necessary for a claim that includes the computer-readable (storage) medium to be valid. Known statutory computer-readable mediums include hardware (e.g., registers, random access memory (RAM), non-volatile (NV) storage, to name a few), but may or may not be limited to hardware.

In one embodiment, a portion of the distributed proxy and cache system for network traffic management resides in or is in communication with device 250, including local proxy 275 (mobile client) and/or cache 285. The local proxy 275 can provide an interface on the device 250 for users to access device applications and services including email, IM, voice mail, visual voicemail, feeds, Internet, games, productivity tools, or other applications, etc.

Figure 3A:
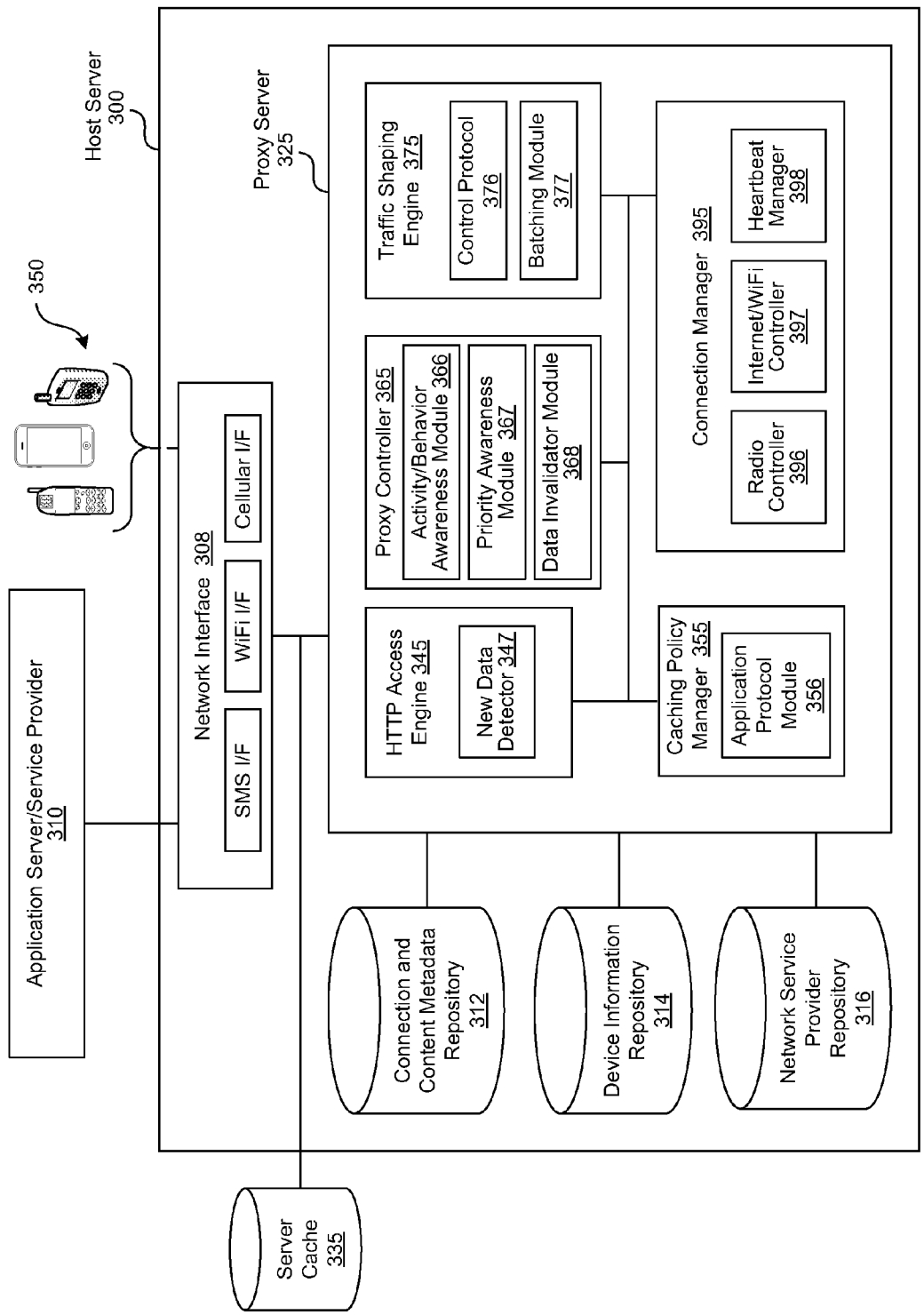
FIG. 3A depicts a block diagram illustrating an example of server-side components in a distributed proxy and cache system that manages traffic in a wireless network (or broadband network) for resource conservation, content caching, and/or traffic management.

The proxy 275 is generally application independent and can be used by applications (e.g., both proxy-aware and proxy-unaware applications 210 and 220 or mobile applications) to open TCP connections to a remote server (e.g., the server 100 in the examples of FIG. 1A-1B and/or server proxy 125/325 shown in the examples of FIG. 1B and FIG. 3A). In some instances, the local proxy 275 includes a proxy API 225 which can be optionally used to interface with proxy-aware applications 220 (or applications (e.g., mobile applications) on a mobile device (e.g., any wireless device)).

The applications 210 and 220 can generally include any user application, widgets, software, HTTP-based application, web browsers, video or other multimedia streaming or downloading application, video games, social network applications, email clients, RSS management applications, application stores, document management applications, productivity enhancement applications, etc. The applications can be provided with the device OS, by the device manufacturer, by the network service provider, downloaded by the user, or provided by others.

One embodiment of the local proxy 275 includes or is coupled to a context API 206, as shown. The context API 206 may be a part of the operating system 204 or device platform or independent of the operating system 204, as illustrated. The operating system 204 can include any operating system including but not limited to, any previous, current, and/or future versions/releases of, Windows Mobile, iOS, Android, Symbian, Palm OS, Brew MP, Java 2 Micro Edition (J2ME), Blackberry, etc.

The context API 206 may be a plug-in to the operating system 204 or a particular client/application on the device 250. The context API 206 can detect signals indicative of user or device activity, for example, sensing motion, gesture, device location, changes in device location, device backlight, keystrokes, clicks, activated touch screen, mouse click or detection of other pointer devices. The context API 206 can be coupled to input devices or sensors on the device 250 to identify these signals. Such signals can generally include input received in response to explicit user input at an input device/mechanism at the device 250 and/or collected from ambient signals/contextual cues detected at or in the vicinity of the device 250 (e.g., light, motion, piezoelectric, etc.).

In one embodiment, the user activity module 215 interacts with the context API 206 to identify, determine, infer, detect, compute, predict, and/or anticipate, characteristics of user activity on the device 250. Various inputs collected by the context API 206 can be aggregated by the user activity module 215 to generate a profile for characteristics of user activity. Such a profile can be generated by the user activity module 215 with various temporal characteristics. For instance, user activity profile can be generated in real-time for a given instant to provide a view of what the user is doing or not doing at a given time (e.g., defined by a time window, in the last minute, in the last 30 seconds, etc.), a user activity profile can also be generated for a 'session' defined by an application or web page that describes the characteristics of user behavior with respect to a specific task they are engaged in on the device 250, or for a specific time period (e.g., for the last 2 hours, for the last 5 hours).

Additionally, characteristic profiles can be generated by the user activity module 215 to depict a historical trend for user activity and behavior (e.g., 1 week, 1 mo., 2 mo., etc.). Such historical profiles can also be used to deduce trends of user behavior, for example, access frequency at different times of day, trends for certain days of the week (weekends or week days), user activity trends based on location data (e.g., IP address, GPS, or cell tower coordinate data) or changes in location data (e.g., user activity based on user location, or user activity based on whether the user is on the go, or traveling outside a home region, etc.) to obtain user activity characteristics.

In one embodiment, user activity module 215 can detect and track user activity with respect to applications, documents, files, windows, icons, and folders on the device 250. For example, the user activity module 215 can detect when an application or window (e.g., a web browser or any other type of application) has been exited, closed, minimized, maximized, opened, moved into the foreground, or into the background, multimedia content playback, etc.

In one embodiment, characteristics of the user activity on the device 250 can be used to locally adjust behavior of the device (e.g., mobile device or any wireless device) to optimize its resource consumption such as battery/power consumption and more generally, consumption of other device resources including memory, storage, and processing power. In one embodiment, the use of a radio on a device can be adjusted based on characteristics of user behavior (e.g., by the radio controller 266 of the connection manager 265) coupled to the user activity module 215. For example, the radio controller 266 can turn the radio on or off, based on characteristics of the user activity on the device 250. In addition, the radio controller 266 can adjust the power mode of the radio (e.g., to be in a higher power mode or lower power mode) depending on characteristics of user activity.

In one embodiment, characteristics of the user activity on device 250 can also be used to cause another device (e.g., other computers, a mobile device, a wireless device, or a non-portable device) or server (e.g., host server 100 and 300 in the examples of FIG. 1A-B and FIG. 3A) which can communicate (e.g., via a cellular or other network) with the device 250 to modify its communication frequency with the device 250. The local proxy 275 can use the characteristics information of user behavior determined by the user activity module 215 to instruct the remote device as to how to modulate its communication frequency (e.g., decreasing communication frequency, such as data push frequency if the user is idle, requesting that the remote device notify the device 250 if new data, changed, data, or data of a certain level of importance becomes available, etc.).

In one embodiment, the user activity module 215 can, in response to determining that user activity characteristics indicate that a user is active after a period of inactivity, request that a remote device (e.g., server host server 100 and 300 in the examples of FIG. 1A-B and FIG. 3A) send the data that was buffered as a result of the previously decreased communication frequency.

In addition, or in alternative, the local proxy 275 can communicate the characteristics of user activity at the device 250 to the remote device (e.g., host server 100 and 300 in the examples of FIG. 1A-B and FIG. 3A) and the remote device determines how to alter its own communication frequency with the device 250 for network resource conservation and conservation of device 250 resources.

One embodiment of the local proxy 275 further includes a request/transaction manager 235, which can detect, identify, intercept, process, manage, data requests initiated on the device 250, for example, by applications 210 and/or 220, and/or directly/indirectly by a user request. The request/transaction manager 235 can determine how and when to process a given request or transaction, or a set of requests/transactions, based on transaction characteristics.

The request/transaction manager 235 can prioritize requests or transactions made by applications and/or users at the device 250, for example by the prioritization engine 241. Importance or priority of requests/transactions can be determined by the request/transaction manager 235 by applying a rule set, for example, according to time sensitivity of the transaction, time sensitivity of the content in the transaction, time criticality of the transaction, time criticality of the data transmitted in the transaction, and/or time criticality or importance of an application making the request.

In addition, transaction characteristics can also depend on whether the transaction was a result of user-interaction or other user-initiated action on the device (e.g., user interaction with a application (e.g., a mobile application)). In general, a time critical transaction can include a transaction resulting from a user-initiated data transfer, and can be prioritized as such. Transaction characteristics can also depend on the amount of data that will be transferred or is anticipated to be transferred as a result of the requested transaction. For example, the connection manager 265, can adjust the radio mode (e.g., high power or low power mode via the radio controller 266) based on the amount of data that will need to be transferred.

In addition, the radio controller 266/connection manager 265 can adjust the radio power mode (high or low) based on time criticality/sensitivity of the transaction. The radio controller 266 can trigger the use of high power radio mode when a time-critical transaction (e.g., a transaction resulting from a user-initiated data transfer, an application running in the foreground, any other event meeting a certain criteria) is initiated or detected.

In general, the priorities can be set by default, for example, based on device platform, device manufacturer, operating system, etc. Priorities can alternatively or in additionally be set by the particular application; for example, the Facebook application (e.g., a mobile application) can set its own priorities for various transactions (e.g., a status update can be of higher priority than an add friend request or a poke request, a message send request can be of higher priority than a message delete request, for example), an email client or IM chat client may have its own configurations for priority. The prioritization engine 241 may include set of rules for assigning priority.

The prioritization engine 241 can also track network provider limitations or specifications on application or transaction priority in determining an overall priority status for a request/transaction. Furthermore, priority can in part or in whole be determined by user preferences, either explicit or implicit. A user, can in general, set priorities at different tiers, such as, specific priorities for sessions, or types, or applications (e.g., a browsing session, a gaming session, versus an IM chat session, the user may set a gaming session to always have higher priority than an IM chat session, which may have higher priority than web-browsing session). A user can set application-specific priorities, (e.g., a user may set Facebook-related transactions to have a higher priority than LinkedIn-related transactions), for specific transaction types (e.g., for all send message requests across all applications to have higher priority than message delete requests, for all calendar-related events to have a high priority, etc.), and/or for specific folders.

The prioritization engine 241 can track and resolve conflicts in priorities set by different entities. For example, manual settings specified by the user may take precedence over device OS settings, network provider parameters/limitations (e.g., set in default for a network service area, geographic locale, set for a specific time of day, or set based on service/fee type) may limit any user-specified settings and/or application-set priorities. In some instances, a manual synchronization request received from a user can override some, most, or all priority settings in that the requested synchronization is performed when requested, regardless of the individually assigned priority or an overall priority ranking for the requested action.

Priority can be specified and tracked internally in any known and/or convenient manner, including but not limited to, a binary representation, a multi-valued representation, a graded representation and all are considered to be within the scope of the disclosed technology.

TABLE I

| Change (initiated on device) | Priority | Change (initiated on server) | Priority |
|---|---|---|---|
| Send email | High | Receive email | High |
| Delete email | Low | Edit email | Often not possible to sync (Low if possible) |
| (Un)read email | Low | | |
| Move message | Low | New email in deleted items | Low |
| Read more | High | | |
| Download attachment | High | Delete an email | Low |
| | | (Un)Read an email | Low |
| New Calendar event | High | Move messages | Low |
| Edit/change Calendar event | High | Any calendar change | High |
| | | Any contact change | High |
| Add a contact | High | Wipe/lock device | High |
| Edit a contact | High | Settings change | High |
| Search contacts | High | Any folder change | High |
| Change a setting | High | Connector restart | High (if no changes nothing is sent) |
| Manual send/receive | High | | |
| IM status change | Medium | Social Network Status Updates | Medium |
| Auction outbid or change notification | High | Sever Weather Alerts | High |
| Weather Updates | Low | News Updates | Low |

Table I above shows, for illustration purposes, some examples of transactions with examples of assigned priorities in a binary representation scheme. Additional assignments are possible for additional types of events, requests, transactions, and as previously described, priority assignments can be made at more or less granular levels, e.g., at the session level or at the application level, etc.

As shown by way of example in the above table, in general, lower priority requests/transactions can include, updating message status as being read, unread, deleting of messages, deletion of contacts; higher priority requests/transactions, can in some instances include, status updates, new IM chat message, new email, calendar event update/cancellation/deletion, an event in a mobile gaming session, or other entertainment related events, a purchase confirmation through a web purchase or online, request to load additional or download content, contact book related events, a transaction to change a device setting, location-aware or location-based events/transactions, or any other events/request/transactions initiated by a user or where the user is known to be, expected to be, or suspected to be waiting for a response, etc.

Inbox pruning events (e.g., email, or any other types of messages), are generally considered low priority and absent other impending events, generally will not trigger use of the radio on the device 250. Specifically, pruning events to remove old email or other content can be 'piggy backed' with other communications if the radio is not otherwise on, at the time of a scheduled pruning event. For example, if the user has preferences set to 'keep messages for 7 days old,' then instead of powering on the device radio to initiate a message delete from the device 250 the moment that the message has exceeded 7 days old, the message is deleted when the radio is powered on next. If the radio is already on, then pruning may occur as regularly scheduled.

The request/transaction manager 235, can use the priorities for requests (e.g., by the prioritization engine 241) to manage outgoing traffic from the device 250 for resource optimization (e.g., to utilize the device radio more efficiently for battery conservation). For example, transactions/requests below a certain priority ranking may not trigger use of the radio on the device 250 if the radio is not already switched on, as controlled by the connection manager 265. In contrast, the radio controller 266 can turn on the radio such a request can be sent when a request for a transaction is detected to be over a certain priority level.

In one embodiment, priority assignments (such as that determined by the local proxy 275 or another device/entity) can be used cause a remote device to modify its communication with the frequency with the mobile device or wireless device. For example, the remote device can be configured to send notifications to the device 250 when data of higher importance is available to be sent to the mobile device or wireless device.

In one embodiment, transaction priority can be used in conjunction with characteristics of user activity in shaping or managing traffic, for example, by the traffic shaping engine 255. For example, the traffic shaping engine 255 can, in response to detecting that a user is dormant or inactive, wait to send low priority transactions from the device 250, for a period of time. In addition, the traffic shaping engine 255 can allow multiple low priority transactions to accumulate for batch transferring from the device 250 (e.g., via the batching module 257). In one embodiment, the priorities can be set, configured, or readjusted by a user. For example, content depicted in Table I in the same or similar form can be accessible in a user interface on the device 250 and for example, used by the user to adjust or view the priorities.

The batching module 257 can initiate batch transfer based on certain criteria. For example, batch transfer (e.g., of multiple occurrences of events, some of which occurred at different instances in time) may occur after a certain number of low priority events have been detected, or after an amount of time elapsed after the first of the low priority event was initiated. In addition, the batching module 257 can initiate batch transfer of the cumulated low priority events when a higher priority event is initiated or detected at the device 250. Batch transfer can otherwise be initiated when radio use is triggered for another reason (e.g., to receive data from a remote device such as host server 100 or 300). In one embodiment, an impending pruning event (pruning of an inbox), or any other low priority events, can be executed when a batch transfer occurs.

In general, the batching capability can be disabled or enabled at the event/transaction level, application level, or session level, based on any one or combination of the following: user configuration, device limitations/settings, manufacturer specification, network provider parameters/limitations, platform-specific limitations/settings, device OS settings, etc. In one embodiment, batch transfer can be initiated when an application/window/file is closed out, exited, or moved into the background; users can optionally be prompted before initiating a batch transfer; users can also manually trigger batch transfers.

In one embodiment, the local proxy 275 locally adjusts radio use on the device 250 by caching data in the cache 285. When requests or transactions from the device 250 can be satisfied by content stored in the cache 285, the radio controller 266 need not activate the radio to send the request to a remote entity (e.g., the host server 100, 300, as shown in FIG. 1A and FIG. 3A or a content provider/application server such as the server/provider 110 shown in the examples of FIG. 1A and FIG. 1B). As such, the local proxy 275 can use the local cache 285 and the cache policy manager 245 to locally store data for satisfying data requests to eliminate or reduce the use of the device radio for conservation of network resources and device battery consumption.

In leveraging the local cache, once the request/transaction manager 225 intercepts a data request by an application on the device 250, the local repository 285 can be queried to determine if there is any locally stored response, and also determine whether the response is valid. When a valid response is available in the local cache 285, the response can be provided to the application on the device 250 without the device 250 needing to access the cellular network or wireless broadband network.

If a valid response is not available, the local proxy 275 can query a remote proxy (e.g., the server proxy 325 of FIG. 3A) to determine whether a remotely stored response is valid. If so, the remotely stored response (e.g., which may be stored on the server cache 135 or optional caching server 199 shown in the example of FIG. 1B) can be provided to the mobile device, possibly without the mobile device 250 needing to access the cellular network, thus relieving consumption of network resources.

If a valid cache response is not available, or if cache responses are unavailable for the intercepted data request, the local proxy 275, for example, the caching policy manager 245, can send the data request to a remote proxy (e.g., server proxy 325 of FIG. 3A) which forwards the data request to a content source (e.g., application server/content provider 110 of FIG. 1A) and a response from the content source can be provided through the remote proxy, as will be further described in the description associated with the example host server 300 of FIG. 3A. The cache policy manager 245 can manage or process requests that use a variety of protocols, including but not limited to HTTP, HTTPS, IMAP, POP, SMTP, XMPP, and/or ActiveSync. The caching policy manager 245 can locally store responses for data requests in the local database 285 as cache entries, for subsequent use in satisfying same or similar data requests.

The caching policy manager 245 can request that the remote proxy monitor responses for the data request and the remote proxy can notify the device 250 when an unexpected response to the data request is detected. In such an event, the cache policy manager 245 can erase or replace the locally stored response(s) on the device 250 when notified of the unexpected response (e.g., new data, changed data, additional data, etc.) to the data request. In one embodiment, the caching policy manager 245 is able to detect or identify the protocol used for a specific request, including but not limited to HTTP, HTTPS, IMAP, POP, SMTP, XMPP, and/or ActiveSync. In one embodiment, application specific handlers (e.g., via the application protocol module 246 of the caching policy manager 245) on the local proxy 275 allows for optimization of any protocol that can be port mapped to a handler in the distributed proxy (e.g., port mapped on the proxy server 325 in the example of FIG. 3A).

In one embodiment, the local proxy 275 notifies the remote proxy such that the remote proxy can monitor responses received for the data request from the content source for changed results prior to returning the result to the device 250, for example, when the data request to the content source has yielded same results to be returned to the mobile device. In general, the local proxy 275 can simulate application server responses for applications on the device 250, using locally cached content. This can prevent utilization of the cellular network for transactions where new/changed data is not available, thus freeing up network resources and preventing network congestion.

In one embodiment, the local proxy 275 includes an application behavior detector 236 to track, detect, observe, monitor, applications (e.g., proxy-aware and/or unaware applications 210 and 220) accessed or installed on the device 250. Application behaviors, or patterns in detected behaviors (e.g., via the pattern detector 237) of one or more applications accessed on the device 250 can be used by the local proxy 275 to optimize traffic in a wireless network needed to satisfy the data needs of these applications.

For example, based on detected behavior of multiple applications, the traffic shaping engine 255 can align content requests made by at least some of the applications over the network (wireless network) (e.g., via the alignment module 256). The alignment module 256 can delay or expedite some earlier received requests to achieve alignment. When requests are aligned, the traffic shaping engine 255 can utilize the connection manager to poll over the network to satisfy application data requests. Content requests for multiple applications can be aligned based on behavior patterns or rules/settings including, for example, content types requested by the multiple applications (audio, video, text, etc.), device (e.g., mobile or wireless device) parameters, and/or network parameters/traffic conditions, network service provider constraints/specifications, etc.

In one embodiment, the pattern detector 237 can detect recurrences in application requests made by the multiple applications, for example, by tracking patterns in application behavior. A tracked pattern can include, detecting that certain applications, as a background process, poll an application server regularly, at certain times of day, on certain days of the week, periodically in a predictable fashion, with a certain frequency, with a certain frequency in response to a certain type of event, in response to a certain type user query, frequency that requested content is the same, frequency with which a same request is made, interval between requests, applications making a request, or any combination of the above, for example.

Such recurrences can be used by traffic shaping engine 255 to offload polling of content from a content source (e.g., from an application server/content provider 110 of FIG. 1A) that would result from the application requests that would be performed at the mobile device or wireless device 250 to be performed instead, by a proxy server (e.g., proxy server 125 of FIG. 1B or proxy server 325 of FIG. 3A) remote from the device 250. Traffic shaping engine 255 can decide to offload the polling when the recurrences match a rule. For example, there are multiple occurrences or requests for the same resource that have exactly the same content, or returned value, or based on detection of repeatable time periods between requests and responses such as a resource that is requested at specific times during the day. The offloading of the polling can decrease the amount of bandwidth consumption needed by the mobile device 250 to establish a wireless (cellular or other wireless broadband) connection with the content source for repetitive content polls.

As a result of the offloading of the polling, locally cached content stored in the local cache 285 can be provided to satisfy data requests at the device 250, when content change is not detected in the polling of the content sources. As such, when data has not changed, application data needs can be satisfied without needing to enable radio use or occupying cellular bandwidth in a wireless network. When data has changed and/or new data has been received, the remote entity to which polling is offloaded, can notify the device 250. The remote entity may be the host server 300 as shown in the example of FIG. 3A.

In one embodiment, the local proxy 275 can mitigate the need/use of periodic keep-alive messages (heartbeat messages) to maintain TCP/IP connections, which can consume significant amounts of power thus having detrimental impacts on mobile device battery life. The connection manager 265 in the local proxy (e.g., the heartbeat manager 267) can detect, identify, and intercept any or all heartbeat (keep-alive) messages being sent from applications.

The heartbeat manager 267 can prevent any or all of these heartbeat messages from being sent over the cellular, or other network, and instead rely on the server component of the distributed proxy system (e.g., shown in FIG. 1B) to generate the and send the heartbeat messages to maintain a connection with the backend (e.g., application server/provider 110 in the example of FIG. 1A).

The local proxy 275 generally represents any one or a portion of the functions described for the individual managers, modules, and/or engines. The local proxy 275 and device 250 can include additional or less components; more or less functions can be included, in whole or in part, without deviating from the novel art of the disclosure.

Figure 2B:
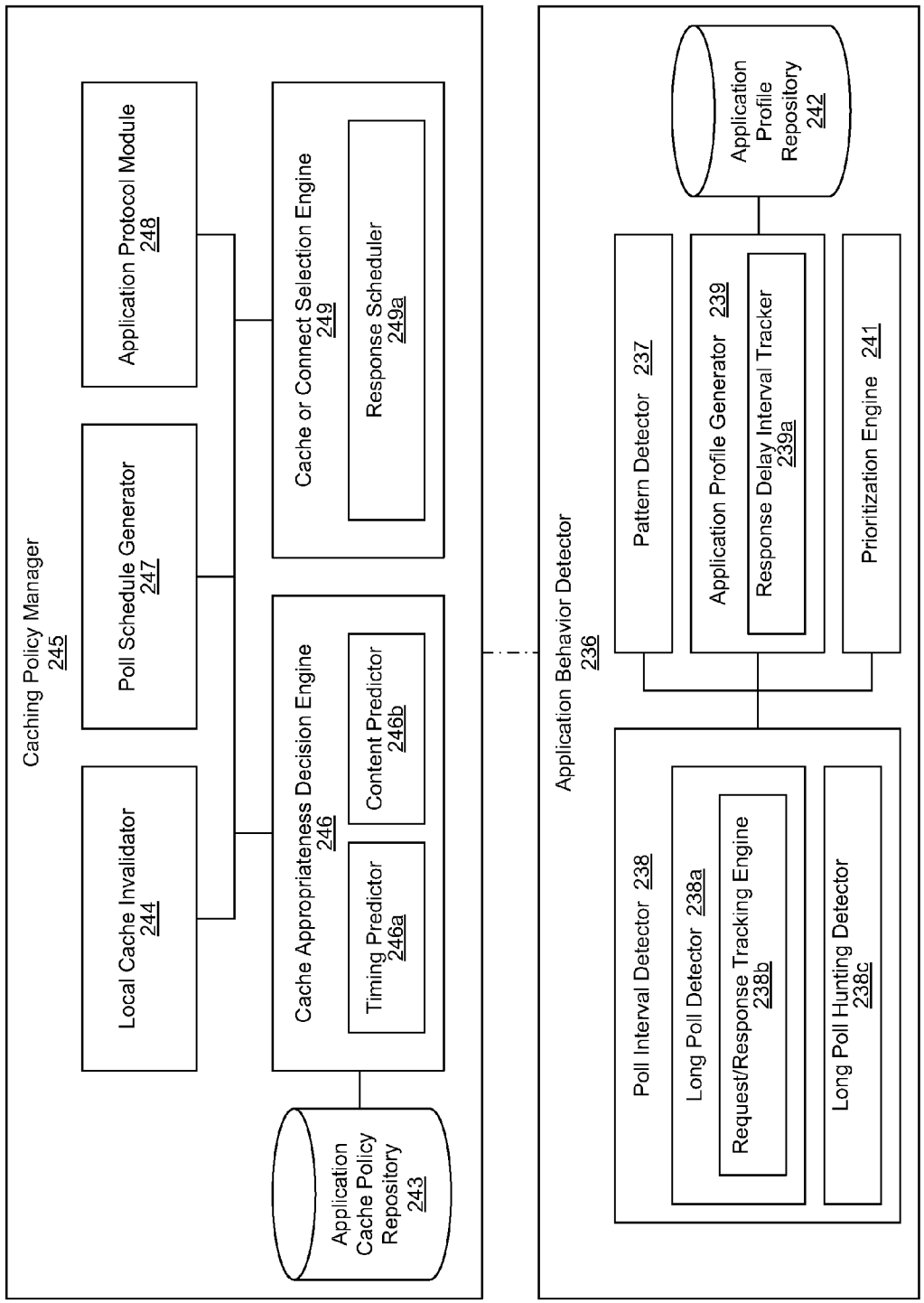
FIG. 2B depicts a block diagram illustrating another example of components in the application behavior detector and the caching policy manager in the local proxy on the client-side of the distributed proxy system shown in the example of FIG. 2A.

FIG. 2B depicts a block diagram illustrating another example of components in the application behavior detector 236 and the caching policy manager 245 in the local proxy 275 on the client-side of the distributed proxy system shown in the example of FIG. 2A.

In one embodiment, the caching policy manager 245 includes a cache appropriateness decision engine 246, a poll schedule generator 247, an application protocol module 248, a cache or connect selection engine 249 and/or a local cache invalidator 244. The cache appropriateness decision engine 246 can further include a timing predictor 246a and/or a content predictor 246b and the cache or connect selection engine 249 includes a response scheduler 249a. One embodiment of caching policy manager 245 includes an application cache policy repository 243.

In one embodiment, the application behavior detector 236 includes a pattern detector 237, a poll interval detector 238, an application profile generator 239, and/or a priority engine 241. The poll interval detector 238 may further include a long poll detector 238a having a response/request tracking engine 238b. The poll interval detector 238 may further include a long poll hunting detector 238c. The application profile generator 239 can further include a response delay interval tracker 239a.

The pattern detector 237, application profile generator 239, and the priority engine 241 were also described in association with the description of the pattern detector shown in the example of FIG. 2A. One embodiment further includes an application profile repository 242 which can be used by the local proxy 275 to store information or metadata regarding application profiles (e.g., behavior, patterns, type of HTTP requests, etc.)

The cache appropriateness decision engine 246 can detect, assess, or determine, whether content from a content source (e.g., application server/content provider 110 in the example of FIG. 1B) with which a mobile device (e.g., any wireless device) 250 interacts, has content that may be suitable for caching. In some instances, content from a given application server/content provider (e.g., the server/content provider 110 of FIG. 1B) is determined to be suitable for caching based on a set of criteria, for example, criteria specifying time criticality of the content that is being requested from the content source. In one embodiment, the local proxy (e.g., the local proxy 175 or 275 of FIG. 1B and FIG. 2A) applies a selection criteria to store the content from the host server which is requested by an application as cached elements in a local cache on the mobile device to satisfy subsequent requests made by the application.

The cache appropriateness decision engine 246, further based on detected patterns of requests sent from the mobile device 250 (e.g., by a application (e.g., a mobile application) or other types of clients on the device 250) and/or patterns of received responses can detect predictability in requests and/or responses. If the requests are made with some identifiable pattern (e.g., regular intervals, intervals having a detectable pattern, or trend (e.g., increasing, decreasing, constant) etc.) the timing predictor 246a can determine that the requests made by a given application on a device is predictable and identify it to be potentially appropriate for caching, at least from a timing standpoint. An identifiable pattern or trend can generally include any application or client behavior which may be simulated either locally, for example, on the local proxy 275 on the mobile device 250 or simulated remotely, for example, by the proxy server 325 on the host 300, or a combination of local and remote simulation to emulate application behavior.

In one embodiment, for a long poll type request, the local proxy 175 can begin to cache responses on a third request when the response delay times for the first two responses are the same, substantially the same, or detected to be increasing in intervals. In general, the received responses for the first two responses should be the same, and upon verifying that the third response received for the third request is the same (e.g., if R0=R1=R2), the third response can be locally cached on the mobile device. Less or more same responses may be required to begin caching, depending on the type of application, type of data, type of content, or user preferences, or carrier/network operator specifications.

Figure 8:
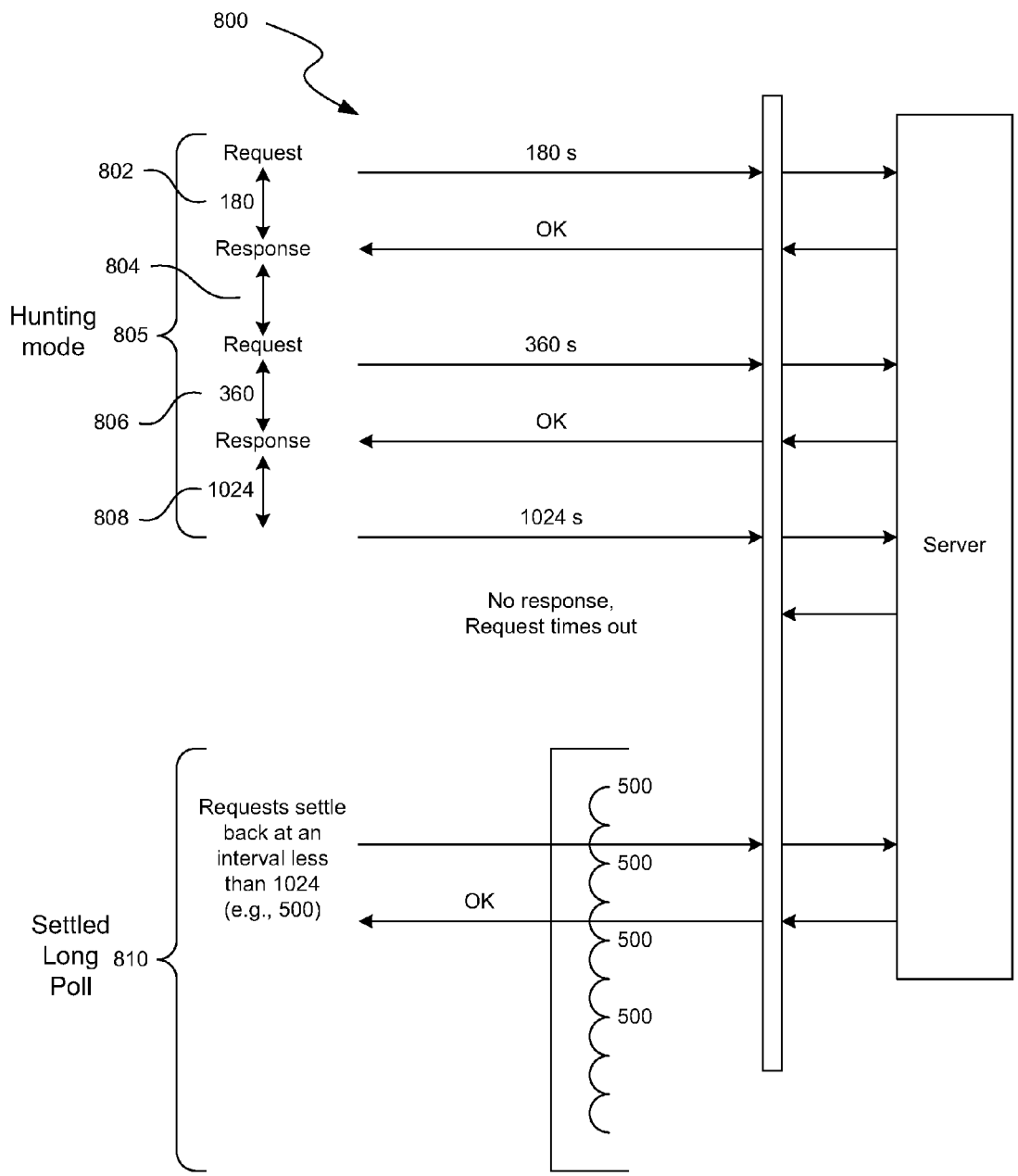
FIG. 8 depicts a timing diagram showing hunting mode behavior in a long poll request and a timing diagram showing timing characteristics when the long poll has settled.

Increasing response delays with same responses for long polls can indicate a hunting period (e.g., a period in which the application/client on the mobile device is seeking the longest time between a request and response that a given network will allow, a timing diagram showing timing characteristics is illustrated in FIG. 8), as detected by the long poll hunting detector 238c of the application behavior detector 236.

An example can be described below using T0, T1, T2, where T indicates the delay time between when a request is sent and when a response (e.g., the response header) is detected/received for consecutive requests:

$$T0 = Response0(t) - Request0(t) = 180 \text{ s. (+/-tolerance)}$$

$$T1 = Response1(t) - Request1(t) = 240 \text{ s. (+/-tolerance)}$$

$$T2 = Response2(t) - Request2(t) = 500 \text{ s. (+/-tolerance)}$$

In the example timing sequence shown above, T0<T1<T2, this may indicate a hunting pattern for a long poll when network timeout has not yet been reached or exceeded. Furthermore, if the responses R0, R1, and R2 received for the three requests are the same, R2 can be cached. In this example, R2 is cached during the long poll hunting period, without waiting for the long poll to settle, thus expediting response caching (e.g., this is optional accelerated caching behavior which can be implemented for all or select applications).

As such, the local proxy 275 can specify information that can be extracted from the timing sequence shown above (e.g., polling schedule, polling interval, polling type) to the proxy server and begin caching and to request the proxy server to begin polling and monitoring the source (e.g., using any of T0, T1, T2 as polling intervals but typically T2, or the largest detected interval without timing out, and for which responses from the source is received will be sent to the proxy server 325 of FIG. 3A for use in polling the content source (e.g., application server/service provider 310)).

However, if the time intervals are detected to be getting shorter, the application (e.g., a mobile application)/client may still be hunting for a time interval for which a response can be reliably received from the content source (e.g., application/server server/provider 110 or 310), and as such caching typically should not begin until the request/response intervals indicate the same time interval or an increasing time interval, for example, for a long poll type request.

An example of handling a detected decreasing delay can be described below using T0, T1, T2, T3, and T4 where T indicates the delay time between when a request is sent and when a response (e.g., the response header) is detected/received for consecutive requests:

$T0 = Response0(t) - Request0(t) = 180$ s. (+/−tolerance)

$T1 = Response1(t) - Request1(t) = 240$ s. (+/−tolerance)

$T2 = Response2(t) - Request2(t) = 500$ s. (+/−tolerance)

$T3 =$ Time out at 700 s. (+/−tolerance)

$T4 = Response4(t) - Request4(t) = 600$ (+/−tolerance)

If a pattern for response delays $T1 < T2 < T3 > T4$ is detected, as shown in the above timing sequence, (e.g., detected by the long poll hunting detector 238c of the application behavior detector 236), it can be determined that T3 likely exceeded the network time out during a long poll hunting period. In Request 3, a response likely was not received since the connection was terminated by the network, application, server, or other reason before a response was sent or available. On Request 4 (after T4), if a response (e.g., Response 4) is detected or received, the local proxy 275 can then use the response for caching (if the content repeatability condition is met). The local proxy can also use T4 as the poll interval in the polling schedule set for the proxy server to monitor/poll the content source.

Note that the above description shows that caching can begin while long polls are in hunting mode in the event of detecting increasing response delays, as long as responses are received and not timed out for a given request. This can be referred to as the optional accelerated caching during long poll hunting. Caching can also begin after the hunting mode (e.g., after the poll requests have settled to a constant or near constant delay value) has completed. Note that hunting may or may not occur for long polls and when hunting occurs, the proxy 275 can generally detect this and determine whether to begin to cache during the hunting period (increasing intervals with same responses) or wait until the hunt settles to a stable value.

In one embodiment, the timing predictor 246a of the cache appropriateness decision engine 246 can track timing of responses received from outgoing requests from a application (e.g., a mobile application) or client, to detect any identifiable patterns which can be partially wholly reproducible, such that locally cached responses can be provided to the requesting client on the mobile device 250 in a manner that simulates content source (e.g., application server/content provider 110 or 310) behavior. For example, the manner in which (e.g., from a timing standpoint) responses or content would be delivered to the requesting application/client on the device 250. This ensures preservation of user experience when responses to application or mobile client requests are served from a local and/or remote cache instead of being retrieved/received directly from the content source (e.g., application, content provider 110 or 310).

In one embodiment, the decision engine 246 or the timing predictor 246a determines the timing characteristics a given application (e.g., a mobile application) or client from, for example, the request/response tracking engine 238a and/or the application profile generator 239 (e.g., the response delay interval tracker 239a). Using the timing characteristics, the predictor 246a determines whether the content received in response to the requests are suitable or are potentially suitable for caching. For example, poll request intervals between two consecutive requests from a given application can be used to determine whether request intervals are repeatable (e.g., constant, near constant, increasing with a pattern, decreasing with a pattern, etc.) and can be predicted and thus reproduced at least some of the times either exactly or approximated within a tolerance level.

In some instances, the timing characteristics of a given request type for a specific application, or for multiple requests of an application, or for multiple applications can be stored in the application profile repository 242. The application profile repository 242 can generally store any type of information or metadata regarding application request/response characteristics including timing patterns, timing repeatability, content repeatability, etc.

The application profile repository 242 can also store metadata indicating the type of request used by a given application (e.g., long polls, long-held HTTP requests, HTTP streaming, push, COMET push, etc.) Application profiles indicating request type by applications can be used when subsequent same/similar requests are detected, or when requests are detected from an application which has already been categorized. In this manner, timing characteristics for the given request type or for requests of a specific application which has been tracked and/or analyzed, need not be reanalyzed.

Application profiles can be associated with a time-to-live (e.g., or a default expiration time). The use of an expiration time for application profiles, or for various aspects of an application or request's profile can be used on a case by case basis. The time-to-live or actual expiration time of application profile entries can be set to a default value or determined individually, or a combination thereof. Application profiles can also be specific to wireless networks, physical networks, network operators, or specific carriers, for example.

A given application profile may also be treated or processed differently (e.g., different behavior of the local proxy 275 and the remote proxy 325) depending on the mobile account associated with a mobile device from which the application is being accessed. For example, a higher paying account, or a premier account may allow more frequent access of the wireless network or higher bandwidth allowance thus affecting the caching policies implemented between the local proxy 275 and proxy server 325 with an emphasis on better performance compared to conservation of resources. A given application profile may also be treated or processed differently under different wireless network conditions (e.g., based on congestion or network outage, etc.).

The cache appropriateness decision engine 246 (e.g., the content predictor 246b) can definitively identify repeatability or identify indications of repeatability, potential repeatability, or predictability in responses received from a content source (e.g., the content host/application server 110 shown in the example of FIG. 1A-B). Repeatability can be detected by, for example, tracking at least two responses received from the content source and determines if the two responses are the same. The two responses may or may not be responses sent in response to consecutive requests. In one embodiment, hash values of the responses received for requests from a given application are used to determine repeatability of content (with or without heuristics) for the application in general and/or for the specific request. Additional same responses may be required for some applications or under certain circumstances.

Repeatability in received content need not be 100% ascertained. For example, responses can be determined to be repeatable if a certain number or a certain percentage of responses are the same, or similar. The certain number or certain percentage of same/similar responses can be tracked over a select period of time, set by default or set based on the application generating the requests (e.g., whether the application is highly dynamic with constant updates or less dynamic with infrequent updates). Any indicated predictability or repeatability, or possible repeatability can be utilized by the distributed system in caching content to be provided to a requesting application or client on the mobile device 250, Note that cache appropriateness can be determined, tracked, and managed for multiple clients or applications on the mobile device 250. Cache appropriateness can also be determined for different requests or request types initiated by a given client or application on the mobile device 250. The caching policy manager 245, along with the timing predictor 246a and/or the content predictor 246b which heuristically determines or estimates predictability or potential predictability, can track, manage and store cacheability information for various application or various requests for a given application. Cacheability information may also include conditions (e.g., an application can be cached at certain times of the day, or certain days of the week, or certain requests of a given application can be cached, or all requests with a given destination address can be cached) under which caching is appropriate which can be determined and/or tracked by the cache appropriateness decision engine 246 and stored and/or updated when appropriate in the application cache policy repository 243 coupled to the cache appropriateness decision engine 246.

The information in the application cache policy repository 243 regarding cacheability of requests, applications, and/or associated conditions can be used later on when same requests are detected. In this manner, the decision engine 246, and/or the timing and content predictors 246a/b need not track and reanalyze request/response timing and content characteristics to make an assessment regarding cacheability. In addition, the cacheability information can in some instances be shared with local proxies of other mobile devices, by way of direct communication or via the host server (e.g., proxy server 325 of host server 300).

For example, cacheability information detected by the local proxy 275 on various mobile devices can be sent to a remote host server or a proxy server 325 on the host server (e.g., host server 300 or proxy server 325 shown in the example of FIG. 3A, host 100 and proxy server 125 in the example of FIG. 1A-B). The remote host or proxy server can then distribute the information regarding application-specific, request-specific cacheability information and/or any associated conditions to various mobile devices or their local proxies in a wireless network or across multiple wireless networks (same service provider or multiple wireless service providers) for their use.

The selection criteria can further include, by way of example, but not limitation, state of the mobile device indicating whether the mobile device is active or inactive, network conditions, and/or radio coverage statistics. The cache appropriateness decision engine 246 can any one or any combination of the criteria, and in any order, in identifying sources for which caching may be suitable.

Once application servers/content providers having identified or detected content that is potentially suitable for local caching on the mobile device 250, the cache policy manager 245 can proceed to cache the associated content received from the identified sources by storing content received from the content source as cache elements in a local cache (e.g., local cache 185 or 285 shown in the examples of FIG. 1B and FIG. 2A, respectively) on the mobile device 250. The content source can also be identified to a proxy server (e.g., proxy server 125 or 325 shown in the examples of FIG. 1B and FIG. 3A, respectively) remote from and in wireless communication with the mobile device 250 such that the proxy server can monitor the content source (e.g., application server/content provider 110) for new or changed data. Similarly, the local proxy (e.g., the local proxy 175 or 275 of FIG. 1B and FIG. 2A, respectively) can identify to the proxy server that content received from a specific application server/content provider is being stored as cached elements in the local cache.

Once content has been locally cached, the cache policy manager 245 can, upon receiving future polling requests to contact the application server/content host (e.g., 110 or 310), can retrieve the cached elements from the local cache to respond to the polling request made at the mobile device 250 such that a radio of the mobile device is not activated to service the polling request. Such servicing and fulfilling application (e.g., a mobile application) requests locally via a local cache entries allow for more efficient resource and mobile network traffic utilization and management since network bandwidth and other resources need not be used to request/receive poll responses which may have not changed from a response that has already been received at the mobile device 250.

For example, the local proxy 275, upon receipt of an outgoing request from its mobile device 250 or from an application or other type of client on the mobile device 250 can intercept the request and determine whether a cached response is available in the local cache 285 of the mobile device 250. If so, the outgoing request is responded to, by the local proxy 275 using the cached response on the cache of the mobile device. As such, the outgoing request can be filled or satisfied without a need to send the outgoing request over the wireless network, thus conserving network resources and battery consumption.

In one embodiment, the responding to the requesting application/client on the device 250 is timed to correspond to a manner in which the content server would have responded to the outgoing request over a persistent connection (e.g., over the persistent connection, or long-held HTTP connection, long poll type connection, that would have been established absent interception by the local proxy). The timing of the response can be emulated or simulated by the local proxy 275 to preserve application behavior such that end user experience is not affected, or minimally affected by serving stored content from the local cache 285 rather than fresh content received from the intended content source (e.g., content host/application server 110 of FIG. 1A-B). The timing can be replicated exactly or estimated within a tolerance parameter, which may go unnoticed by the user or treated similarly by the application so as to not cause operation issues.

For example, the outgoing request can be a request for a persistent connection intended for the content server (e.g., application server/content provider of examples of FIG. 1A-1B). In a persistent connection (e.g., long poll, COMET-style push or any other push simulation in asynchronous HTTP requests, long-held HTTP request, HTTP streaming, or others) with a content source (server), the connection is held for some time after a request is sent. The connection can typically be persisted between the mobile device and the server until content is available at the server to be sent to the mobile device. Thus, there typically can be some delay in time between when a long poll request is sent and when a response is received from the content source. If a response is not provided by the content source for a certain amount of time, the connection may also terminate due to network reasons (e.g., socket closure) if a response is not sent.

Thus, to emulate a response from a content server sent over a persistent connection (e.g., a long poll style connection), the manner of response of the content server can be simulated by allowing a time interval to elapse before responding to the outgoing request with the cached response. The length of the time interval can be determined on a request by request basis or on an application by application (client by client basis), for example.

In one embodiment, the time interval is determined based on request characteristics (e.g., timing characteristics) of an application on the mobile device from which the outgoing request originates. For example, poll request intervals (e.g., which can be tracked, detected, determined by the long poll detector 238a of the poll interval detector 238) can be used to determine the time interval to wait before responding to a request with a local cache entry and managed by the response scheduler 249a.

One embodiment of the cache policy manager 245 includes a poll schedule generator 247 which can generate a polling schedule for one or more applications on the mobile device 250. The polling schedule can specify a polling interval that can be employed by the proxy server (e.g., proxy server 125 or 325 shown in the examples of FIG. 1B and FIG. 3A) in monitoring the content source for one or more applications. The polling schedule can be determined, for example, based on the interval between the polling requests directed to the content source from the mobile device. In one embodiment, the poll interval detector 238 of the application behavior detector 236 can monitor polling requests directed to a content source from the mobile device 250 in order to determine an interval between the polling requests made from any or all applications (e.g., including mobile applications).

For example, the poll interval detector 238 can track requests and responses for applications or clients on the device 250. In one embodiment, consecutive requests are tracked prior to detection of an outgoing request initiated from the application (e.g., a mobile application) on the mobile device 250, by the same mobile client or application. In one embodiment, an outgoing request from a mobile device 250 is detected to be for a persistent connection (e.g., a long poll, COMET style push, and long-held (HTTP) request) based on timing characteristics of prior requests from the same application or client on the mobile device 250. For example, requests and/or corresponding responses can be tracked by the request/response tracking engine 238b of the long poll detector 238a of the poll interval detector 238.

The timing characteristics of the consecutive requests can be determined to set up a polling schedule for the application or client. The polling schedule can be used to monitor the content source (content source/application server) for content changes such that cached content stored on the local cache in the mobile device 250 can be appropriated managed (e.g., updated or discarded). In one embodiment, the timing characteristics can include, for example, a response delay time ('D') and/or an idle time ('IT').

The response delay time and idle time typical of a long poll are illustrated in the timing diagram shown below and also described further in detail with references to FIG. 17A-B. In one embodiment, the response/request tracking engine 238b can track requests and responses to determine, compute, and/or estimate, the timing diagrams for applicant or client requests.

For example, the response/request tracking engine 238b detects a first request (Request 0) initiated by a client on the mobile device and a second request (Request 1) initiated by the client on the mobile device after a response is received at the mobile device responsive to the first request. The second request is one that is subsequent to the first request. The relationship between requests can be seen in the following timing diagrams of FIG. 17A-17B.

In one embodiment, the response/request tracking engine 238b can track requests and responses to determine, compute, and/or estimate, the timing diagrams for applicant or client requests. The response/request tracking engine 238b can detect a first request initiated by a client on the mobile device and a second request initiated by the client on the mobile device after a response is received at the mobile device responsive to the first request. The second request is one that is subsequent to the first request.

The response/request tracking engine 238b further determines relative timings between the first, second requests, and the response received in response to the first request. In general, the relative timings can be used by the long poll detector 238a to determine whether requests generated by the application are long poll requests.

Note that in general, the first and second requests that are used by the response/request tracking engine 238b in computing the relative timings are selected for use after a long poll hunting period has settled or in the event when long poll hunting does not occur. Timing characteristics that are typical of a long poll hunting period is illustrated in the example of FIG. 8 and can be, for example, detected by the long poll hunting detector 238c. In other words, the requests tracked by the response/request tracking engine 238b and used for determining whether a given request is a long poll occurs after the long poll has settled (e.g., shown in 810 of FIG. 8 after the hunting mode 805 has completed).

In one embodiment, the long poll hunting detector 238c can identify or detect hunting mode, by identifying increasing request intervals (e.g., increasing delays), for example. The long poll hunting detector 238a can also detect hunting mode by detecting increasing request intervals, followed by a request with no response (e.g., connection timed out), or by detecting increasing request intervals followed by a decrease in the interval. In addition, the long poll hunting detector 238c can apply a filter value or a threshold value to request-response time delay value (e.g., an absolute value) above which the detected delay can be considered to be a long poll request-response delay, The filter value can be any suitable value characteristic of long polls and/or network conditions (e.g., 2 s, 5 s, 10 s, 15 s, 20 s., etc.) can be used as a filter or threshold value.

The response delay time ('D') refers to the start time to receive a response after a request has been sent and the idle refers to time to send a subsequent request after the response has been received. In one embodiment, the outgoing request is detected to be for a persistent connection based on a comparison (e.g., performed by the tracking engine 238b) of the response delay time relative ('D') or average of ('D') (e.g., any average over any period of time) to the idle time ('IT'), for example, by the long poll detector 238a. The number of averages used can be fixed, dynamically adjusted, or changed over a longer period of time. For example, the requests initiated by the client are determined to be long poll requests if the response delay time interval is greater than the idle time interval (D>IT or D>>IT). In one embodiment, the tracking engine 238b of the long poll detector computes, determines, or estimates the response delay time interval as the amount of time elapsed between time of the first request and initial detection or full receipt of the response.

In one embodiment, a request is detected to be for a persistent connection when the idle time ('IT') is short since persistent connections, established in response to long poll requests or long poll HTTP requests, for example, can also be characterized in detecting immediate or near-immediate issuance of a subsequent request after receipt of a response to a previous request (e.g., IT~0). As such the idle time ('IT") can also be used to detect such immediate or near-immediate re-request to identify long poll requests. The absolute or relative timings determined by the tracking engine 238b are used to determine whether the second request is immediately or near-immediately re-requested after the response to the first request is received. For example, a request may be categorized as a long poll request if D+RT+IT~D+RT since IT is small for this to hold true. IT may be determined to be small if it is less than a threshold value. Note that the threshold value could be fixed or calculated over a limited time period (a session, a day, a month, etc.), or calculated over a longer time period (e.g., several months or the life of the analysis). For example, for every request, the average IT can be determined, and the threshold can be determined using this average IT (e.g., the average IT less a certain percentage may be used as the threshold). This can allow the threshold to automatically adapt over time to network conditions and changes in server capability, resource availability or server response. A fixed threshold can take upon any value including by way of example but not limitation (e.g., 1 s. 2 s. 3 s. . . . etc.).

In one embodiment, the long poll detector 238a can compare the relative timings (e.g., determined by the tracker engine 238b) to request-response timing characteristics for other applications to determine whether the requests of the application are long poll requests. For example, the requests initiated by a client or application can be determined to be long poll requests if the response delay interval time ('D') or the average response delay interval time (e.g., averaged over x number of requests or any number of delay interval times averaged over x amount of time) is greater than a threshold value.

The threshold value can be determined using response delay interval times for requests generated by other clients, for example by the request/response tracking engine 238b and/or by the application profile generator 239 (e.g., the response delay interval tracker 239a). The other clients may reside on the same mobile device and the threshold value is determined locally by components on the mobile device. The threshold value can be determined for all requests over all resources server over all networks, for example. The threshold value can be set to a specific constant value (e.g., 30 seconds, for example) to be used for all requests, or any request which does not have an applicable threshold value (e.g., long poll is detected if D>30 seconds).

In some instances, the other clients reside on different mobile devices and the threshold can be determined by a proxy server (e.g., proxy server 325 of the host 300 shown in the example of FIG. 3A-B) which is external to the mobile device and able to communicate over a wireless network with the multiple different mobile devices, as will be further described with reference to FIG. 3B.

In one embodiment, the cache policy manager 245 sends the polling schedule to the proxy server (e.g., proxy server 125 or 325 shown in the examples of FIG. 1B and FIG. 3A) and can be used by the proxy server in monitoring the content source, for example, for changed or new content (updated response different from the cached response associated with a request or application). A polling schedule sent to the proxy can include multiple timing parameters including but not limited to interval (time from request 1 to request 2), a time out interval (time to wait for response, used in long polls, for example). Referring to the timing diagram of a request/response timing sequence shown in the example of FIG. 17A-B, the timing intervals 'RI', 'D', 'RT', and/or 'IT', or some statistical manipulation of the above values (e.g., average, standard deviation, etc.) may all or in part be sent to the proxy server.

For example, in the case when the local proxy 275 detects a long poll, the various timing intervals in a request/response timing sequence (e.g., 'D', 'RT', and/or 'IT') can be sent to the proxy server 325 for use in polling the content source (e.g., application server/content host 110). The local proxy 275 can also identify to the proxy server 325 that a given application or request to be monitored is a long poll request (e.g., instructing the proxy server to set a 'long poll flag', for example). In addition, the proxy server uses the various timing intervals to determine when to send keep-alive indications on behalf of mobile devices.

The local cache invalidator 244 of the caching policy manager 245 can invalidate cache elements in the local cache (e.g., cache 185 or 285) when new or changed data (e.g., updated response) is detected from the application server/content source for a given request. The cached response can be determined to be invalid for the outgoing request based on a notification received from the proxy server (e.g., proxy 325 or the host server 300). The source which provides responses to requests of the mobile client can be monitored to determine relevancy of the cached response stored in the cache of the mobile device 250 for the request. For example, the cache invalidator 244 can further remove/delete the cached response from the cache of the mobile device when the cached response is no longer valid for a given request or a given application.

In one embodiment, the cached response is removed from the cache after it is provided once again to an application which generated the outgoing request after determining that the cached response is no longer valid. The cached response can be provided again without waiting for the time interval or provided again after waiting for a time interval (e.g., the time interval determined to be specific to emulate the response delay in a long poll). In one embodiment, the time interval is the response delay 'D' or an average value of the response delay 'D' over two or more values.

The new or changed data can be, for example, detected by the proxy server (e.g., proxy server 125 or 325 shown in the examples of FIG. 1B and FIG. 3A). When a cache entry for a given request/poll has been invalidated, the use of the radio on the mobile device 250 can be enabled (e.g., by the local proxy or the cache policy manager 245) to satisfy the subsequent polling requests, as further described with reference to the interaction diagram of FIG. 4B.

One embodiment of the cache policy manager 245 includes a cache or connect selection engine 249 which can decide whether to use a locally cached entry to satisfy a poll/content request generated at the mobile device 250 by an application or widget. For example, the local proxy 275 or the cache policy manger 245 can intercept a polling request, made by an application (e.g., mobile application) on the mobile device, to contact the application server/content provider. The selection engine 249 can determine whether the content received for the intercepted request has been locally stored as cache elements for deciding whether the a radio of the mobile device needs to be activated to satisfy the request made by the application (e.g., a mobile application) and also determine whether the cached response is still valid for the outgoing request prior to responding to the outgoing request using the cached response.

In one embodiment, the local proxy 275, in response to determining that relevant cached content exists and is still valid, can retrieve the cached elements from the local cache to provide a response to the application which made the polling request such that a radio of the mobile device is not activated to provide the response to the application. In general, the local proxy 275 continues to provide the cached response each time the outgoing request is received until the updated response different from the cached response is detected.

When it is determined that the cached response is no longer valid, a new request for a given request is transmitted over the wireless network for an updated response. The request can be transmitted to the application server/content provider (e.g., server/host 110) or the proxy server on the host server (e.g., proxy 325 on the host 300) for a new and updated response. In one embodiment the cached response can be provided again as a response to the outgoing request if a new response is not received within the time interval, prior to removal of the cached response from the cache on the mobile device; an example process flow is illustrated in the flow chart of FIG. 10.

FIG. 3A depicts a block diagram illustrating an example of server-side components (host server 300 and proxy server 325) in a distributed proxy and cache system that manages traffic in a wireless network for resource conservation, content caching, and/or traffic management.

The host server 300 generally includes, for example, a network interface 308 and/or one or more repositories 312, 314, 316. Note that server 300 may be any portable/mobile or non-portable device, server, cluster of computers and/or other types of processing units (e.g., any number of a machine shown in the example of FIG. 11) able to receive, transmit signals to satisfy data requests over a network including any wired or wireless networks (e.g., WiFi, cellular, Bluetooth, etc.).

The network interface 308 can include networking module(s) or devices(s) that enable the server 300 to mediate data in a network with an entity that is external to the host server 300, through any known and/or convenient communications protocol supported by the host and the external entity. Specifically, the network interface 308 allows the server 308 to communicate with multiple devices including mobile phone devices 350, and/or one or more application servers/content providers 310.

The host server 300 can store information about connections (e.g., network characteristics, conditions, types of connections, etc.) with devices in the connection metadata repository 312. Additionally, any information about third party application or content providers can also be stored in 312. The host server 300 can store information about devices (e.g., hardware capability, properties, device settings, device language, network capability, manufacturer, device model, OS, OS version, etc.) in the device information repository 314. Additionally, the host server 300 can store information about network providers and the various network service areas in the network service provider repository 316.

The communication enabled by network interface 308 allows for simultaneous connections (e.g., including cellular connections) with devices 350 and/or connections (e.g., including wired/wireless, HTTP, Internet connections, LAN, WiFi, etc.) with content servers/providers 310, to manage the traffic between devices 350 and content providers 310, for optimizing network resource utilization and/or to conserver power (battery) consumption on the serviced devices 350. The host server 300 can communicate with mobile devices 350 serviced by different network service providers and/or in the same/different network service areas. The host server 300 can operate and is compatible with devices 350 with varying types or levels of mobile capabilities, including by way of example but not limitation, 1 G, 2G, 2G transitional (2.5G, 2.75G), 3G (IMT-2000), 3G transitional (3.5G, 3.75G, 3.9G), 4G (IMT-advanced), etc.

In general, the network interface 308 can include one or more of a network adaptor card, a wireless network interface card (e.g., SMS interface, WiFi interface, interfaces for various generations of mobile communication standards including but not limited to 1G, 2G, 3G, 3.5G, 4G type networks such as, LTE, WiMAX, etc.), Bluetooth, WiFi, or any other network whether or not connected via a router, an access point, a wireless router, a switch, a multilayer switch, a protocol converter, a gateway, a bridge, a bridge router, a hub, a digital media receiver, and/or a repeater.

The host server 300 can further include, server-side components of the distributed proxy and cache system which can include, a proxy server 325 and a server cache 335. In one embodiment, the proxy server 325 can include an HTTP access engine 345, a caching policy manager 355, a proxy controller 365, a traffic shaping engine 375, a new data detector 347 and/or a connection manager 395.

The HTTP access engine 345 may further include a heartbeat manager 398 the proxy controller 365 may further include a data invalidator module 358 the traffic shaping engine 375 may further include a control protocol 376 and a batching module 377. Additional or less components/modules/engines can be included in the proxy server 325 and each illustrated component.

As used herein, a "module," "a manager," a "handler," a "detector," an "interface," a "controller," a "normalizer," a "generator," an "invalidator," or an "engine" includes a general purpose, dedicated or shared processor and, typically, firmware or software modules that are executed by the processor. Depending upon implementation-specific or other considerations, the module, manager, handler, detector, interface, controller, normalizer, generator, invalidator, or engine can be centralized or its functionality distributed. The module, manager, handler, detector, interface, controller, normalizer, generator, invalidator, or engine can include general or special purpose hardware, firmware, or software embodied in a computer-readable (storage) medium for execution by the processor. As used herein, a computer-readable medium or computer-readable storage medium is intended to include all mediums that are statutory (e.g., in the United States, under 35 U.S.C. 101), and to specifically exclude all mediums that are non-statutory in nature to the extent that the exclusion is necessary for a claim that includes the computer-readable (storage) medium to be valid. Known statutory computer-readable mediums include hardware (e.g., registers, random access memory (RAM), non-volatile (NV) storage, to name a few), but may or may not be limited to hardware.

In the example of a device (e.g., mobile device 350) making an application or content request to an application server or content provider 310, the request may be intercepted and routed to the proxy server 325, which is coupled to the device 350 and the application server/content provider 310. Specifically, the proxy server is able to communicate with the local proxy (e.g., proxy 175 and 275 of the examples of FIG. 1 and FIG. 2 respectively) of the mobile device 350, the local proxy forwards the data request to the proxy server 325 for, in some instances, further processing, and if needed, for transmission to the application server/content server 310 for a response to the data request.

In such a configuration, the host 300, or the proxy server 325 in the host server 300 can utilize intelligent information provided by the local proxy in adjusting its communication with the device in such a manner that optimizes use of network and device resources. For example, the proxy server 325 can identify characteristics of user activity on the device 350 to modify its communication frequency. The characteristics of user activity can be determined by, for example, the activity/behavior awareness module 366 in the proxy controller 365, via information collected by the local proxy on the device 350.

In one embodiment, communication frequency can be controlled by the connection manager 395 of the proxy server 325, for example, to adjust push frequency of content or updates to the device 350. For instance, push frequency can be decreased by the connection manager 395 when characteristics of the user activity indicate that the user is inactive. In one embodiment, when the characteristics of the user activity indicate that the user is subsequently active after a period of inactivity, the connection manager 395 can adjust the communication frequency with the device 350 to send data that was buffered as a result of decreased communication frequency, to the device 350.

In addition, the proxy server 325 includes priority awareness of various requests, transactions, sessions, applications, and/or specific events. Such awareness can be determined by the local proxy on the device 350 and provided to the proxy server 325. The priority awareness module 367 of the proxy server 325 can generally assess the priority (e.g., including time-criticality, time-sensitivity, etc.) of various events or applications; additionally, the priority awareness module 367 can track priorities determined by local proxies of devices 350.

In one embodiment, through priority awareness, the connection manager 395 can further modify communication frequency (e.g., use or radio as controlled by the radio controller 396) of the server 300 with the devices 350. For example, the server 300 can notify the device 350, thus requesting use of the radio if it is not already in use, when data or updates of an importance/priority level which meets a criteria becomes available to be sent.

In one embodiment, the proxy server 325 can detect multiple occurrences of events (e.g., transactions, content, data received from server/provider 310) and allow the events to accumulate for batch transfer to device 350. Batch transfer can be cumulated and transfer of events can be delayed based on priority awareness and/or user activity/application behavior awareness, as tracked by modules 366 and/or 367. For example, batch transfer of multiple events (of a lower priority) to the device 350 can be initiated by the batching module 377 when an event of a higher priority (meeting a threshold or criteria) is detected at the server 300. In addition, batch transfer from the server 300 can be triggered when the server receives data from the device 350, indicating that the device radio is already in use and is thus on. In one embodiment, the proxy server 325 can order the each messages/packets in a batch for transmission based on event/transaction priority, such that higher priority content can be sent first, in case connection is lost or the battery dies, etc.

In one embodiment, the server 300 caches data (e.g., as managed by the caching policy manager 355) such that communication frequency over a network (e.g., cellular network) with the device 350 can be modified (e.g., decreased). The data can be cached, for example in the server cache 335, for subsequent retrieval or batch sending to the device 350 to potentially decrease the need to turn on the device 350 radio. The server cache 335 can be partially or wholly internal to the host server 300, although in the example of FIG. 3A, it is shown as being external to the host 300. In some instances, the server cache 335 may be the same as and/or integrated in part or in whole with another cache managed by another entity (e.g., the optional caching proxy server 199 shown in the example of FIG. 1B), such as being managed by an application server/content provider 110, a network service provider, or another third party.

In one embodiment, content caching is performed locally on the device 350 with the assistance of host server 300. For example, proxy server 325 in the host server 300 can query the application server/provider 310 with requests and monitor changes in responses. When changed or new responses are detected (e.g., by the new data detector 347), the proxy server 325 can notify the mobile device 350, such that the local proxy on the device 350 can make the decision to invalidate (e.g., indicated as out-dated) the relevant cache entries stored as any responses in its local cache. Alternatively, the data invalidator module 368 can automatically instruct the local proxy of the device 350 to invalidate certain cached data, based on received responses from the application server/provider 310. The cached data is marked as invalid, and can get replaced or deleted when new content is received from the content server 310.

Note that data change can be detected by the detector 347 in one or more ways. For example, the server/provider 310 can notify the host server 300 upon a change. The change can also be detected at the host server 300 in response to a direct poll of the source server/provider 310. In some instances, the proxy server 325 can in addition, pre-load the local cache on the device 350 with the new/updated data. This can be performed when the host server 300 detects that the radio on the mobile device is already in use, or when the server 300 has additional content/data to be sent to the device 350.

One or more the above mechanisms can be implemented simultaneously or adjusted/configured based on application (e.g., different policies for different servers/providers 310). In some instances, the source provider/server 310 may notify the host 300 for certain types of events (e.g., events meeting a priority threshold level). In addition, the provider/server 310 may be configured to notify the host 300 at specific time intervals, regardless of event priority.

In one embodiment, the proxy server 325 of the host 300 can monitor/track responses received for the data request from the content source for changed results prior to returning the result to the mobile device, such monitoring may be suitable when data request to the content source has yielded same results to be returned to the mobile device, thus preventing network/power consumption from being used when no new/changes are made to a particular requested. The local proxy of the device 350 can instruct the proxy server 325 to perform such monitoring or the proxy server 325 can automatically initiate such a process upon receiving a certain number of the same responses (e.g., or a number of the same responses in a period of time) for a particular request.

In one embodiment, the server 300, for example, through the activity/behavior awareness module 366, is able to identify or detect user activity, at a device that is separate from the mobile device 350. For example, the module 366 may detect that a user's message inbox (e.g., email or types of inbox) is being accessed. This can indicate that the user is interacting with his/her application using a device other than the mobile device 350 and may not need frequent updates, if at all.

The server 300, in this instance, can thus decrease the frequency with which new or updated content is sent to the mobile device 350, or eliminate all communication for as long as the user is detected to be using another device for access. Such frequency decrease may be application specific (e.g., for the application with which the user is interacting with on another device), or it may be a general frequency decrease (e.g., since the user is detected to be interacting with one server or one application via another device, he/she could also use it to access other services) to the mobile device 350.

In one embodiment, the host server 300 is able to poll content sources 310 on behalf of devices 350 to conserve power or battery consumption on devices 350. For example, certain applications on the mobile device 350 can poll its respective server 310 in a predictable recurring fashion. Such recurrence or other types of application behaviors can be tracked by the activity/behavior module 366 in the proxy controller 365. The host server 300 can thus poll content sources 310 for applications on the mobile device 350, that would otherwise be performed by the device 350 through a wireless (e.g., including cellular connectivity). The host server can poll the sources 310 for new or changed data by way of the HTTP access engine 345 to establish HTTP connection or by way of radio controller 396 to connect to the source 310 over the cellular network. When new or changed data is detected, the new data detector can notify the device 350 that such data is available and/or provide the new/changed data to the device 350.

In one embodiment, the connection manager 395 determines that the mobile device 350 is unavailable (e.g., the radio is turned off) and utilizes SMS to transmit content to the device 350, for instance via the SMSC shown in the example of FIG. 1B. SMS is used to transmit invalidation messages, batches of invalidation messages, or even content in the case the content is small enough to fit into just a few (usually one or two) SMS messages. This avoids the need to access the radio channel to send overhead information. The host server 300 can use SMS for certain transactions or responses having a priority level above a threshold or otherwise meeting a criteria. The server 300 can also utilize SMS as an out-of-band trigger to maintain or wake-up an IP connection as an alternative to maintaining an always-on IP connection.

In one embodiment, the connection manager 395 in the proxy server 325 (e.g., the heartbeat manager 398) can generate and/or transmit heartbeat messages on behalf of connected devices 350, to maintain a backend connection with a provider 310 for applications running on devices 350.

For example, in the distributed proxy system, local cache on the device 350 can prevent any or all heartbeat messages needed to maintain TCP/IP connections required for applications, from being sent over the cellular, or other network, and instead rely on the proxy server 325 on the host server 300 to generate and/or send the heartbeat messages to maintain a connection with the backend (e.g., application server/provider 110 in the example of FIG. 1A). The proxy server can generate the keep-alive (heartbeat) messages independent of the operations of the local proxy on the mobile device.

The repositories 312, 314, and/or 316 can additionally store software, descriptive data, images, system information, drivers, and/or any other data item utilized by other components of the host server 300 and/or any other servers for operation. The repositories may be managed by a database management system (DBMS), for example but not limited to, Oracle, DB2, Microsoft Access, Microsoft SQL Server, PostgreSQL, MySQL, FileMaker, etc.

The repositories can be implemented via object-oriented technology and/or via text files, and can be managed by a distributed database management system, an object-oriented database management system (OODBMS) (e.g., ConceptBase, FastDB Main Memory Database Management System, JDOInstruments, ObjectDB, etc.), an object-relational database management system (ORDBMS) (e.g., Informix, OpenLink Virtuoso, VMDS, etc.), a file system, and/or any other convenient or known database management package.

Figure 3B:
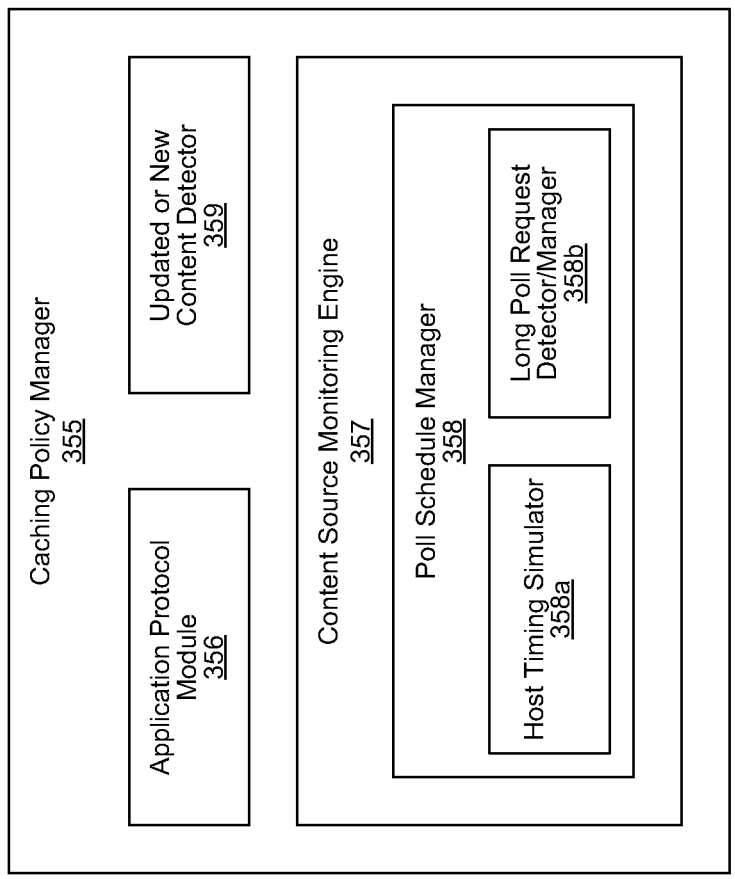
FIG. 3B depicts a block diagram illustrating another example of components in the caching policy manager in the proxy server on the server-side of the distributed proxy system shown in the example of FIG. 3A.

FIG. 3B depicts a block diagram illustrating another example of components in the caching policy manager 355 in the proxy server 325 on the server-side of the distributed proxy system shown in the example of FIG. 3A.

The caching policy manager 355, in one embodiment, can further include, an application protocol module 356, a content source monitoring engine 357 having a poll schedule manager 358, and/or an updated or new content detector 359. In one embodiment, the poll schedule manager 358 further includes a host timing simulator 358a and/or a long poll request detector/manager 358b.

In one embodiment, the proxy server (e.g., the proxy server 125 or 325 of the examples of FIG. 1B and FIG. 3A) can monitor a content source for new or changed data, for example, via the monitoring engine 357. The proxy server, as shown, is an entity external to the mobile device 250 of FIG. 2A-B. The content source (e.g., application server/content provider 110 of FIG. 1B) can be one that has been identified to the proxy server (e.g., by the local proxy) as having content that is being locally cached on a mobile device (e.g., mobile device 150 or 250). The content source can be monitored, for example, by the monitoring engine 357 at a frequency that is based on polling frequency of the content source at the mobile device. The poll schedule can be, for example, generated by the local proxy and sent to the proxy server. The poll frequency can be tracked and/or managed by the poll schedule manager 358.

For example, the proxy server can poll the host (e.g., content provider/application server) on behalf of the mobile device and simulate the polling behavior of the client to the host, via the host timing simulator 358a. The polling behavior can be simulated to include characteristics of a long poll request-response sequences experienced in a persistent connection with the host (e.g., by the long poll request detector/manager 358b). Note that once a polling interval/behavior is set, the local proxy 275 on the device-side and/or the proxy server 325 on the server-side can verify whether application and application server/content host behavior match or can be represented by this predicted pattern. In general, the local proxy and/or the proxy server can detect deviations and when appropriate, re-evaluate and compute, determine, or estimate another polling interval.

In one embodiment, the caching policy manager 355 on the server-side of the distribute proxy can, in conjunction with, or independent of the proxy server 275 on the mobile device, identify or detect long poll requests. For example, the caching policy manager 355 can determine a threshold value to be used in comparison with a response delay interval time (interval time 'D' shown in the example timing diagram of FIG. 17A-B) in a request-response sequence for an application request to identify or detect long poll requests, possible long poll requests (e.g., requests for a persistent connection with a host with which the client communicates, including but not limited to, a long-held HTTP request, a persistent connection enabling COMET style push, request for HTTP streaming, etc.), or other requests which can otherwise be treated as a long poll request.

For example, the threshold value can be determined by the proxy 325 using response delay interval times for requests generated by clients/applications across mobile devices which may be serviced by multiple different cellular or wireless networks. Since the proxy 325 resides on host 300 is able to communicate with multiple mobile devices via multiple networks, the caching policy manager 355 has access to application/client information at a global level which can be used in setting threshold values to categorize and detect long polls.

By tracking response delay interval times across applications across devices over different or same networks, the caching policy manager 355 can set one or more threshold values to be used in comparison with response delay interval times for long poll detection. Threshold values set by the proxy server 325 can be static or dynamic, and can be associated with conditions and/or a time-to-live (an expiration time/date in relative or absolute terms).

In addition, the caching policy manager 35 of the proxy 325 can determine the threshold value, in whole or in part, further based on network delays of a given wireless network, networks serviced by a given carrier (service provider), or multiple wireless networks. The proxy 325 can also determine the threshold value for identification of long poll requests based on delays of one or more application server/content provider (e.g., 110) to which application, mobile application, or mobile client requests are directed.

The proxy server can detect new or changed data at a monitored content source and transmits a message to the mobile device notifying it of such a change such that the mobile device (or the local proxy on the mobile device) can take appropriate action (e.g., to invalidate the cache elements in the local cache. In some instances, the proxy server (e.g., the caching policy manager 355) upon detecting new or changed data, can also store the new or changed data in its cache (e.g., the server cache 135 or 335 of the examples of FIG. 1B and FIG. 3A, respectively). The new/updated data stored in the server cache can in some instances, be used to satisfy content requests at the mobile device, for example, after the proxy server has notified the mobile device of the new/changed content and that the locally cached content has been invalidated.

Figure 4A:
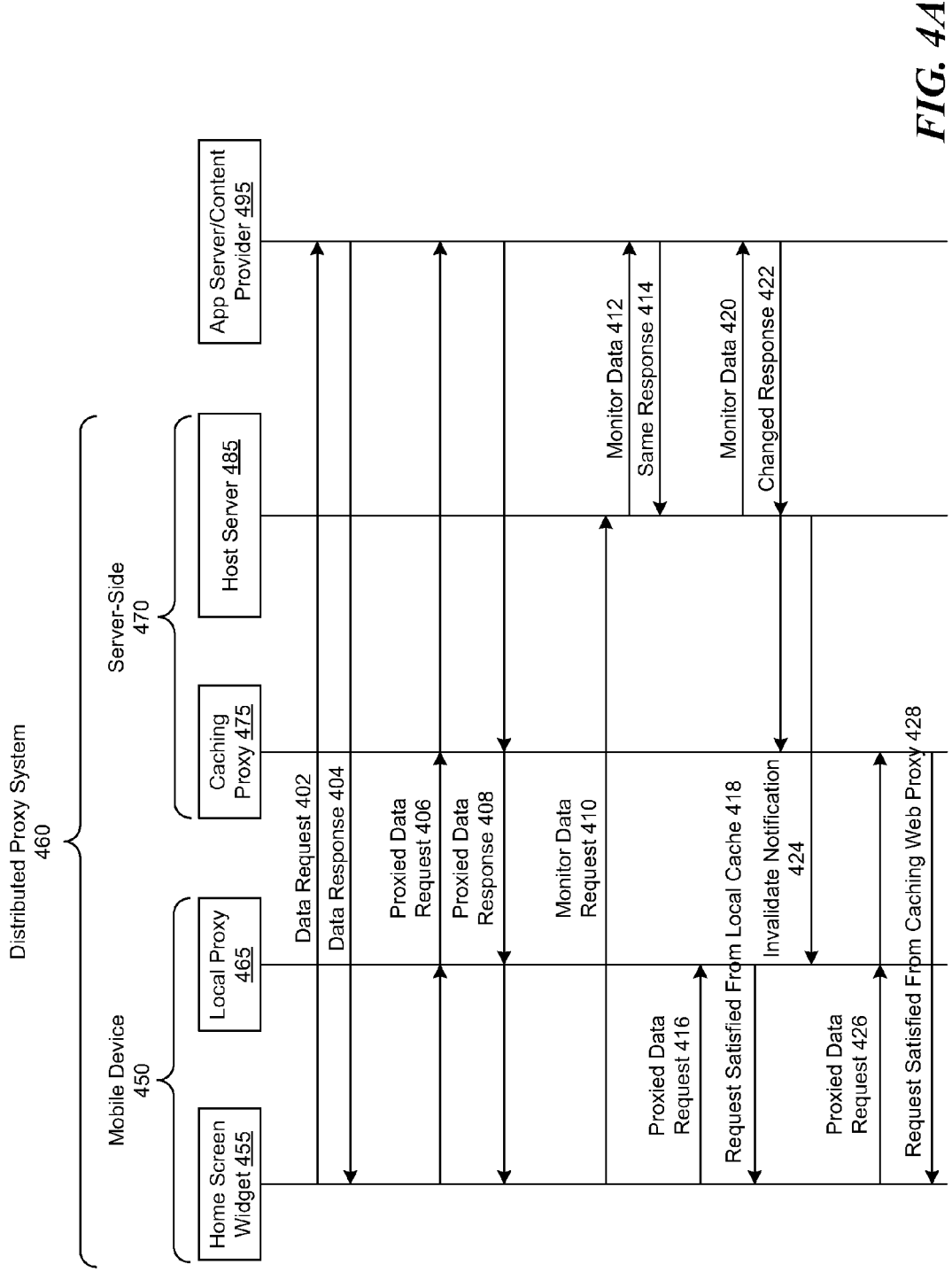
FIG. 4A depicts a timing diagram showing how data requests from a mobile device (e.g., any wireless device) to an application server/content provider in a wireless network (or broadband network) can be coordinated by a distributed proxy system in a manner such that network and battery resources are conserved through using content caching and monitoring performed by the distributed proxy system.

FIG. 4A depicts a diagram showing how data requests from a mobile device 450 to an application server/content provider 495 in a wireless network can be coordinated by a distributed proxy system 460 in a manner such that network and battery resources are conserved through using content caching and monitoring performed by the distributed proxy system 460.

In satisfying application or client requests on a mobile device 450 without the distributed proxy system 460, the mobile device 450, or the software widget executing on the device 450 performs a data request 402 (e.g., an HTTP GET, POST, or other request) directly to the application server 495 and receives a response 404 directly from the server/provider 495. If the data has been updated, the widget on the mobile device 450 can refreshes itself to reflect the update and waits for small period of time and initiates another data request to the server/provider 495.

In one embodiment, the requesting client or software widget 455 on the device 450 can utilize the distributed proxy system 460 in handling the data request made to server/provider 495. In general, the distributed proxy system 460 can include a local proxy 465 (which is typically considered a client-side component of the system 460 and can reside on the mobile device 450), a caching proxy 475 (considered a server-side component 470 of the system 460 and can reside on the host server 485 or be wholly or partially external to the host server 485), a host server 485. The local proxy 465 can be connected to the caching proxy 475 and host server 485 via any network or combination of networks.

When the distributed proxy system 460 is used for data/application requests, the widget 455 can perform the data request 406 via the local proxy 465. The local proxy 465, can intercept the requests made by device applications, and can identify the connection type of the request (e.g., an HTTP get request or other types of requests). The local proxy 465 can then query the local cache for any previous information about the request (e.g., to determine whether a locally stored response is available and/or still valid). If a locally stored response is not available or if there is an invalid response stored, the local proxy 465 can update or store information about the request, the time it was made, and any additional data, in the local cache. The information can be updated for use in potentially satisfying subsequent requests.

The local proxy 465 can then send the request to the host server 485 and the host server 485 can perform the request 406 and returns the results in response 408. The local proxy 465 can store the result and in addition, information about the result and returns the result to the requesting widget 455.

In one embodiment, if the same request has occurred multiple times (within a certain time period) and it has often yielded same results, the local proxy 465 can notify 410 the server 485 that the request should be monitored (e.g., steps 412 and 414) for result changes prior to returning a result to the local proxy 465 or requesting widget 455.

In one embodiment, if a request is marked for monitoring, the local proxy 465 can now store the results into the local cache. Now, when the data request 416, for which a locally response is available, is made by the widget 455 and intercepted at the local proxy 465, the local proxy 465 can return the response 418 from the local cache without needing to establish a connection communication over the wireless network.

In addition, the server proxy performs the requests marked for monitoring 420 to determine whether the response 422 for the given request has changed. In general, the host server 485 can perform this monitoring independently of the widget 455 or local proxy 465 operations. Whenever an unexpected response 422 is received for a request, the server 485 can notify the local proxy 465 that the response has changed (e.g., the invalidate notification in step 424) and that the locally stored response on the client should be erased or replaced with a new response.

In this case, a subsequent data request 426 by the widget 455 from the device 450 results in the data being returned from host server 485 (e.g., via the caching proxy 475) and in step 428, the request is satisfied from the caching proxy 475. Thus, through utilizing the distributed proxy system 460 the wireless (cellular) network is intelligently used when the content/data for the widget or software application 455 on the mobile device 450 has actually changed. As such, the traffic needed to check for the changes to application data is not performed over the wireless (cellular) network. This reduces the amount of generated network traffic and shortens the total time and the number of times the radio module is powered up on the mobile device 450, thus reducing battery consumption, and in addition, frees up network bandwidth.

FIG. 4B depicts an interaction diagram showing how application polls having data requests made by an application/widget 455 (e.g., mobile application) on a mobile device to an application server/content provider 495 in a wireless network can be cached on the local proxy 465 and managed by the distributed caching system (including local proxy 465 and the host server 485 (having server cache 435 or caching proxy server 475).

In one example, when the application/widget 455 (e.g., mobile application/widget) polls an application server/provider 432, the poll can locally be intercepted 434 on the mobile device by local proxy 465. The local proxy 465 can detect that the cached content is available for the polled content in the request and can thus retrieve a response from the local cache to satisfy the intercepted poll 436, without requiring use of wireless network bandwidth or other wireless network resources. The application/widget 455 (e.g., mobile application/widget) can subsequently receive a response to the poll from a cache entry 438.

In another example, the application/widget 455 (e.g., mobile application/widget) polls the application server/provider 440. The poll is intercepted 442 by the local proxy 465 and detects that cache content is unavailable in the local cache and decides to set up the polled source for caching 444. To satisfy the request, the poll is forwarded to the content source 446. The application server/provider 495 receives the poll request from the application and provides a response to satisfy the current request 448. In 450, the mobile application/widget 455 receives the response from the application server/provider to satisfy the request.

In conjunction, in order to set up content caching, the local proxy 465 tracks the polling frequency of the application and can set up a polling schedule to be sent to the host server 452. The local proxy sends the cache set up to the host server 454. The host server 485 can use the cache set up which includes, for example, an identification of the application server/provider to be polled and optionally a polling schedule 456. The host server 485 can now poll the application server/provider 495 to monitor responses to the request 458, on behalf of the mobile device. The application server receives the poll from the host server and responds 460. The host server 485 determines that the same response has been received and polls the application server 495, for example, according to the specified polling schedule 462. The application server/content provider 495 receives the poll and responds accordingly 464.

The host server 485 detects changed or new responses, and notifies the local proxy 465. The host server 485 can additional store the changed or new response in the server cache or caching proxy 468. The local proxy 465 receives notification from the host server 485 that new or changed data is now available and can invalidate the affected cache entries 470. The next time the application/widget 455 (e.g., mobile application/widget) generates the same request for the same server/content provider 472, the local proxy determines that no valid cache entry is available and instead retrieves a response from the server cache 474, for example, through an HTTP connection. The host server 485 receives the request for the new response and sends the response back to the local proxy 475. The request is thus satisfied from the server cache or caching proxy 478 without the need for the mobile device to utilize its radio or to consume mobile network bandwidth thus conserving network resources.

Alternatively, when the application generates the same request in step 480, the local proxy 465, in response to determining that no valid cache entry is available, forwards the poll to the application server/provider 482 over the mobile network. The application server/provider 495 receives the poll and sends the response back to the mobile device 484 over the mobile network. The request is thus satisfied from the server/provider using the mobile network 486.

Figure 5:
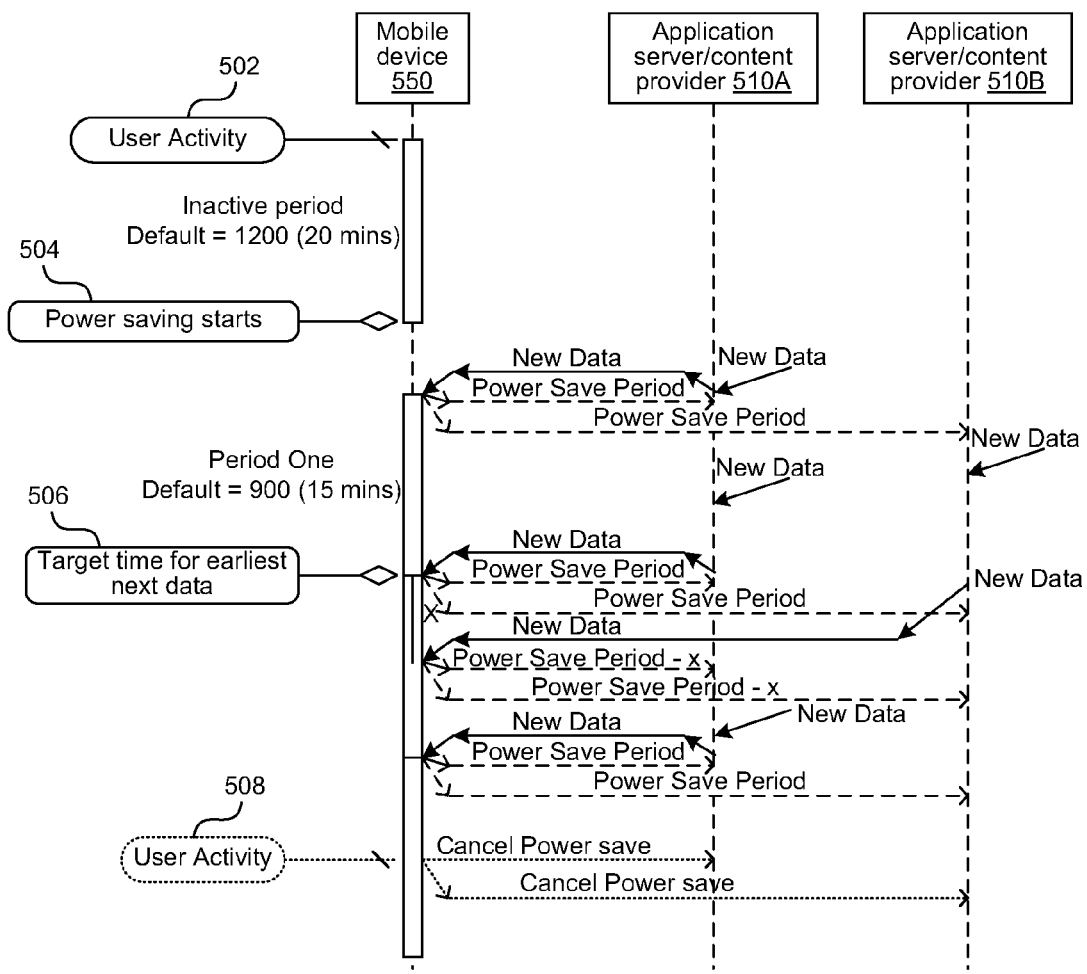
FIG. 5 depicts a diagram showing one example process for implementing a hybrid IP and SMS power saving mode on a mobile device (e.g., any wireless device) using a distributed proxy and cache system (e.g., such as the distributed system shown in the example of FIG. 1B).

FIG. 5 depicts a diagram showing one example process for implementing a hybrid IP and SMS power saving mode on a mobile device 550 using a distributed proxy and cache system (e.g., such as the distributed system shown in the example of FIG. 1B).

In step 502, the local proxy (e.g., proxy 175 in the example of FIG. 1B) monitors the device for user activity. When the user is determined to be active, server push is active. For example, always-on-push IP connection can be maintained and if available, SMS triggers can be immediately sent to the mobile device 550 as it becomes available.

In process 504, after the user has been detected to be inactive or idle over a period of time (e.g., the example is shown for a period of inactivity of 20 min.), the local proxy can adjust the device to go into the power saving mode. In the power saving mode, when the local proxy receives a message or a correspondence from a remote proxy (e.g., the server proxy 135 in the example of FIG. 1B) on the server-side of the distributed proxy and cache system, the local proxy can respond with a call indicating that the device 550 is currently in power save mode (e.g., via a power save remote procedure call). In some instances, the local proxy can take the opportunity to notify multiple accounts or providers (e.g., 510A, and 510B) of the current power save status (e.g., timed to use the same radio power-on event).

In one embodiment, the response from the local proxy can include a time (e.g., the power save period) indicating to the remote proxy (e.g., server proxy 135) and/or the application server/providers 510A/B when the device 550 is next able to receive changes or additional data. A default power savings period can be set by the local proxy.

In one embodiment, if new, changed, or different data or event is received before the end of any one power saving period, then the wait period communicated to the servers 510A/B can be the existing period, rather than an incremented time period. In response, the remote proxy server, upon receipt of power save notification from the device 550, can stop sending changes (data or SMS's) for the period of time requested (the wait period). At the end of the wait period, any notifications received can be acted upon and changes sent to the device 550, for example, as a single batched event or as individual events. If no notifications come in, then push can be resumed with the data or an SMS being sent to the device 550. The proxy server can time the poll or data collect event to optimize batch sending content to the mobile device 550 to increase the chance that the client will receive data at the next radio power on event.

Note that the wait period can be updated in operation in real time to accommodate operating conditions. For example, the local proxy can adjust the wait period on the fly to accommodate the different delays that occur in the system.

Detection of user activity in step 508 at the device 550 causes the power save mode to be exited. When the device 550 exits power save mode, it can begin to receive any changes associated with any pending notifications. If a power saving period has expired, then no power save cancel call may be needed as the proxy server will already be in traditional push operation mode.

In one embodiment, power save mode is not applied when the device 550 is plugged into a charger. This setting can be reconfigured or adjusted by the user or another party. In general, the power save mode can be turned on and off, for example, by the user via a user interface on device 550. In general, timing of power events to receive data can be synchronized with any power save calls to optimize radio use.

Figure 6:
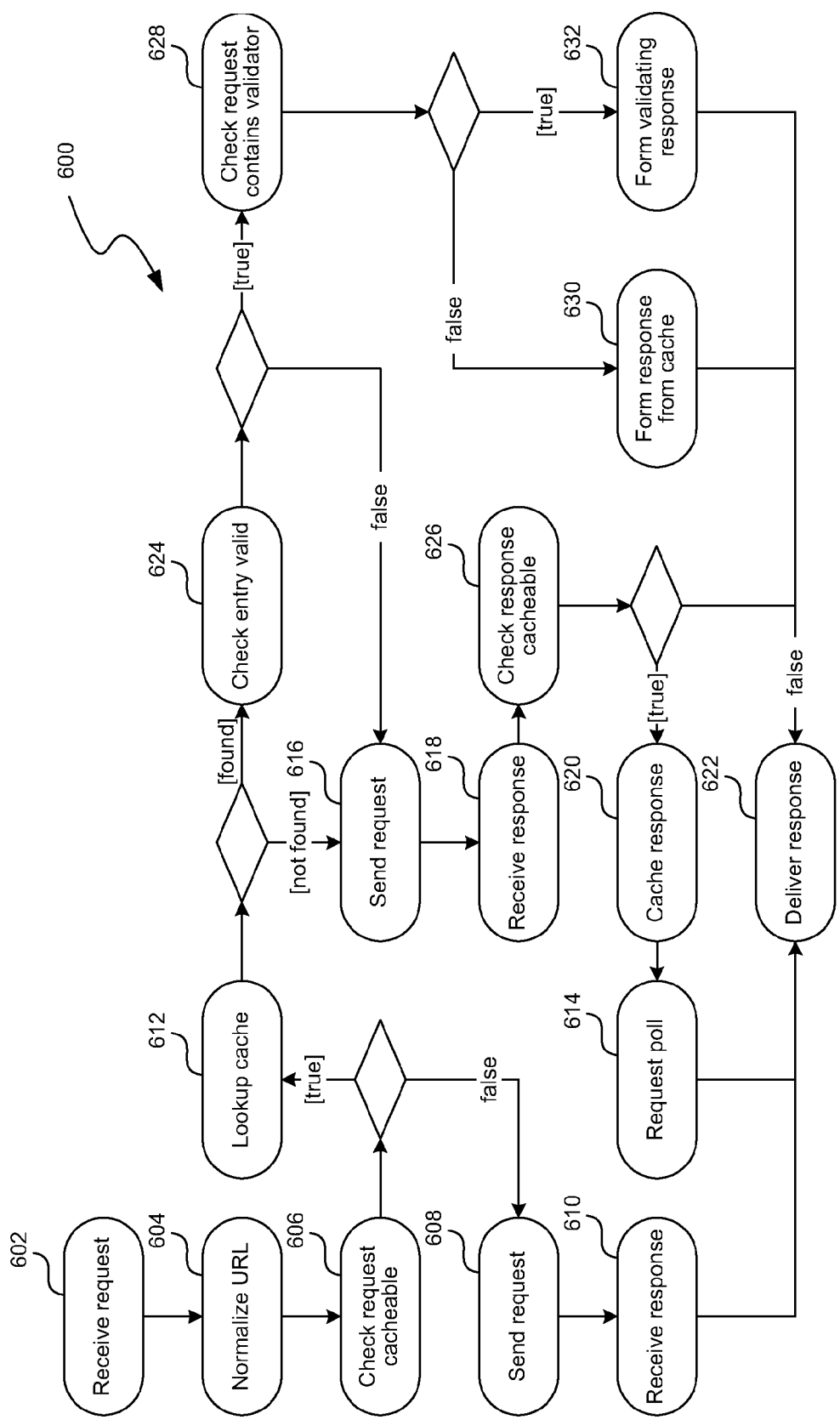
FIG. 6 depicts a flow diagram illustrating an example process for distributed content caching between a mobile device (e.g., any wireless device) and remote proxy and the distributed management of content caching.

FIG. 6 depicts another flow diagram 600 illustrating an example process for distributed content caching between a mobile device and a proxy server and the distributed management of content caching.

As shown in the distributed system interaction diagram in the example of FIG. 4A, the disclosed technology is a distributed caching model with various aspects of caching tasks split between the client-side/mobile device side (e.g., mobile device 450 in the example of FIG. 4A) and the server side (e.g., server side 470 including the host server 485 and/or the optional caching proxy 475).

In general the device-side responsibilities can include, deciding whether a response to a particular request can be and/or should be cached. The device-side of the proxy can make this decision based on information (e.g., timing characteristics, detected pattern, detected pattern with heuristics, indication of predictability or repeatability) collected from/during both request and response, and cache it (e.g., storing it in a local cache on the mobile device). The device side can also notify the server-side in the distributed cache system of the local cache event and notify it monitor the content source (e.g., application server/content provider 110 of FIG. 1A-B).

The device side can further instruct the server side of the distributed proxy to periodically validate the cache response (e.g., by way of polling, or sending polling requests to the content source). The device side can further decide whether a response to a particular cache request should be returned from the local cache (e.g., whether a cache hit is detected). The decision can be made by the device side (e.g., the local proxy on the device) using information collected from/during request and/or responses received from the content source.

In general, the server-side responsibilities can include, validating cached responses for relevancy (e.g., determine whether a cached response is still valid or relevant to its associated request). The server-side can send the mobile device an invalidation request to notify the device side when a cached response is detected to be no longer valid or no longer relevant (e.g., the server invalidates a given content source). The device side then can remove the response from the local cache.

The diagram of FIG. 6 illustrates caching logic processes performed for each detected or intercepted request (e.g., HTTP request) detected at a mobile device (e.g., client-side of the distributed proxy). In step 602, the client-side of the proxy (e.g., local proxy 275 shown in FIG. 2A-B or mobile device 450 of FIG. 4A) receives a request (from an application, mobile application or mobile client). In step 604, URL is normalized and in step the client-side checks to determine if the request is cacheable, in step 606. If the request is determined to be not cacheable in step 612, the request is sent to the source (application server/content provider) in step 608 and the response is received 610 and delivered to the requesting application 622, similar to a request-response sequence without interception by the client side proxy.

If the request is determined to be cacheable, in step 612, the client-side looks up the cache to determine whether a cache entry exists for the current request. If so, in step 624, the client-side can determine whether the entry is valid and if so, the client side can check the request to see if includes a validator (e.g., a modified header or an entity tag) in step 628. For example, the concept of validation is eluded to in section 13.3 of RFC 2616 which describes in possible types of headers. and forms a validating response 632 if so to be delivered to the requesting application in step 622. If the request does not include a validator as determined by step 628, a response is formed from the local cache in step 630 and delivered to the requesting application in step 622. This validation step can be used for content that would otherwise normally be considered un-cacheable.

If, instead, in step 624, the cache entry is found but determined to be no longer valid or invalid, the client side of the proxy, sends the request to the content source (application server/content host) and receives a response directly from the source in step 618. Alternative processing may be performed if the content is determined to include non-cacheable content. Similarly, if in step 612, a cache entry was not found during the look up, the request is also sent in step 616. Once the response is received, the client side checks the response to determine if it is cacheable in step 626. If so, the response is cached in step 620. The client then sends another poll in step 614 and then delivers the response to the requesting application in step 622.

Figure 7:
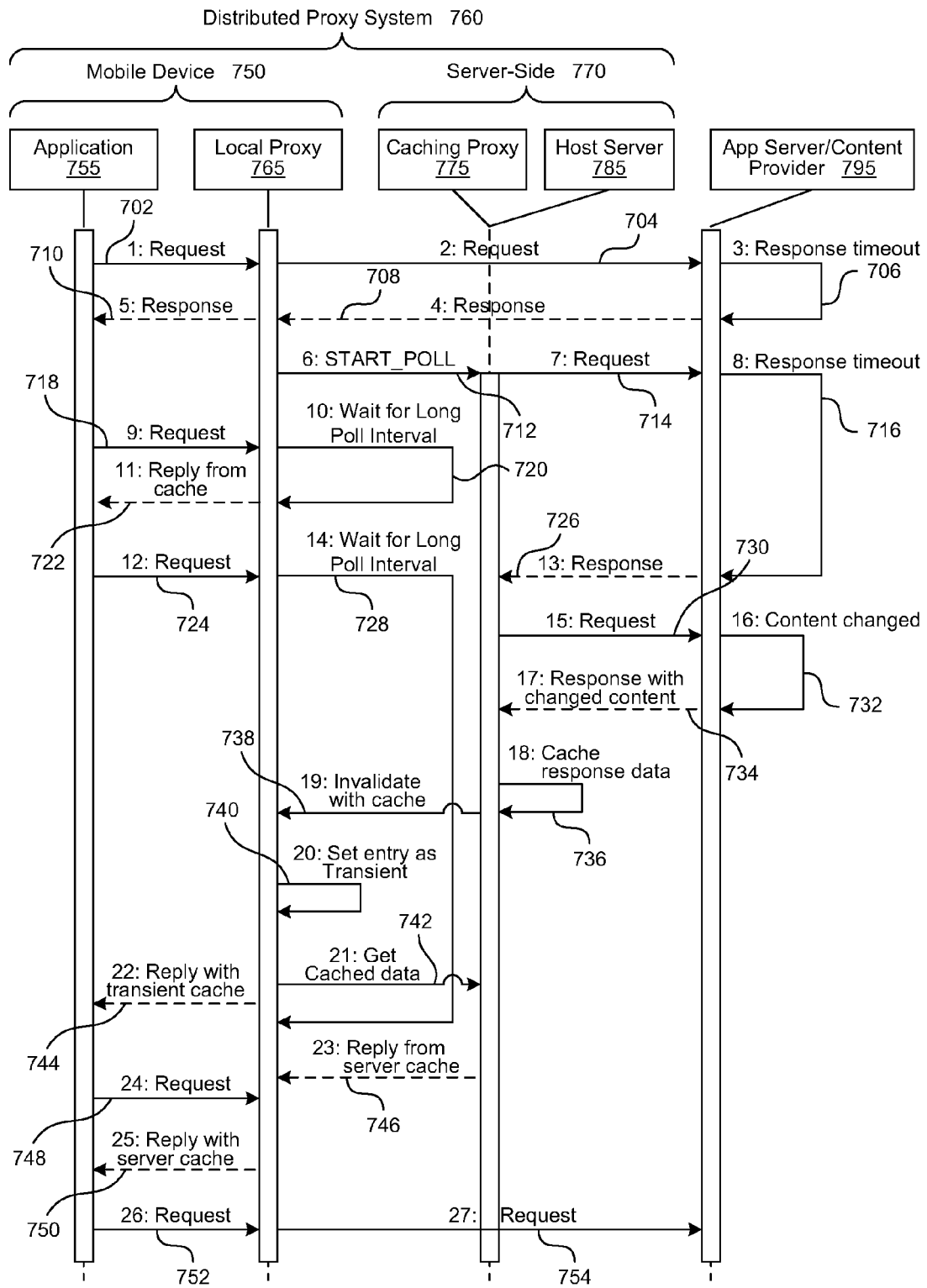
FIG. 7 depicts an interaction diagram showing cache management by a distributed proxy system of content delivered to a mobile application over a long-held request while ensuring freshness of content delivered.

FIG. 7 depicts an interaction diagram showing cache management by a distributed proxy system 760 of content delivered to an application 755 (e.g., mobile application) over a long-held request while ensuring freshness of content delivered.

The diagram illustrates an example process for how cached responses received in long-held requests (e.g., long-held HTTP request, long polls, or HTTP streaming) are provided to the requesting application 755 and management of expired/invalid/non-relevant cache entries. A long-held request can be any request for a persistent connection that is held between the device and the server until a response is available at the server to be sent (or pushed) to the device. The long-held request or long-held HTTP request can allow the device/server interaction to simulate content push over the persistent connection (e.g., COMET style push), for example, over a persisted connection over HTTP.

In step 702, the application 755 sends a request which is detected and intercepted by the local proxy 765 on the mobile device 750 on the client/device-side of the proxy system 760. Note that the request-response sequence 702, 704, 706, and 708 shown occurs after a long poll hunting period, which may sometimes be performed by the application (e.g., a mobile application) sending long poll requests. The long poll hunting period may or may not be performed, but when performed, allows the requesting application 755 to find the longest amount of time it can hold a request with the end server/provider 795 open before the connection times out (e.g., due to network reason, such as socket closures).

A timing diagram showing characteristics request-response timing sequences is further illustrated in the example of FIG. 8. In general, the device proxy 750 or local proxy 765 is able to detect request-response pattern sequences initiated from the application 755 while long poll hunting and can wait until the hunting period has settled prior to caching responses from long poll request. The request-response steps shown between 702 and 710 occur after any long poll hunting request/response pairs, if it was performed by the requesting application 755.

The request is sent to the server/provider 795 in step 704 and the request times out or closes in 706, when the server 795 sends a response in step 708 back to the application 755 on the device side 750. The connection times out when the server 795 sends a response in step 708 due to the nature of the long-held request send in step 702. The response, when sent is also intercepted by the local proxy 760 on the mobile side 750 of the distributed proxy 760, for local caching.

Once cached, the local proxy 765 notifies the server-side 770 of the proxy of the system 760 and requests that the server-side 770 proxy (e.g., the host server 785) begin to monitor the server/provider 790 in step 712. In step 714, the server-side proxy 770 now begins to send requests to the server/provider in order to monitor responses received 716 from the server/provider 795.

The next time the application 755 sends the request 718, the local proxy 765 determines that a local cache entry now exists and waits for a period of time (e.g., a long poll interval) 720 before providing the cached response back to the application 755, in step 722. The local proxy 765 allows the period of time to elapse to simulate the actual behavior of the server/ provider 795 with the application 755, since in an actual long poll request which goes over the network, a response is not received until after some delay, characteristic of the given long poll.

Starting at step 724, another request is sent from the application (e.g., a mobile application) 755 when the response from the server/provider 795 in step 726 is validated. The local proxy 765 waits for an interval in step 728 before replying with the cache entry in step 744. However, in the interim, the server-side proxy 770 in monitoring responses sends a request in step 730 to the server/provider 795 and detects content change in the response received 732 from the server/provider 795 in step 734. The server-side 770 proxy thus caches the changed/updated response data at the server-side proxy in step 736 and notifies the local proxy 765 to invalidate the associated cache entry 738.

The local proxy 765, in response to receiving an invalidation notice, sets the associated entry to be invalidated as being 'transient' in step 740, or otherwise annotated or indicated to be marked for deletion or removal. At this point, the local proxy 765 replies to the application 755 again with the transient cache in step 744. The local proxy 765 also connects to the server-side proxy 770 to obtain the new cached data at the server-side 770, in step 742, and receives a response (the new/updated response) at step 746.

The next time the same request is sent from the application (e.g., a mobile application) in step 748, the local proxy 765 now can reply with the response received from the server cache, in step 750. Thus, even in the event when a cache entry has been invalidated, the application (e.g., a mobile application) request need not be sent over the network (e.g., wireless, or cellular network) to receive a current/relevant response. The subsequent request 752 is sent to the local proxy 765 for processing (e.g., forwarded to the application server/content provider 795) in step 754.

FIG. 8 depicts a timing diagram 800 showing hunting mode behavior 805 in a long poll request and a timing diagram showing timing characteristics when the long poll has settled 810.

In hunting mode 805, the request times are held for an increasing amount of time (180, 360 . . . 1024 s.) until a request times out without receiving a response from the server (as shown in 802, 804, 806, 808). After this time is detected, the request times are now held at some time less than the time it took for a time out (e.g., now 500 s.) and used to send future long poll requests. The diagram 810 shows the timing characteristics of request/response pairs after the long poll hunting period has settled. These characteristics can be detected and identified in operation by the local proxy and/or the remote proxy for handling during caching. As previously described, the distributed caching system can either begin caching (optionally) while the application is still in long poll hunting mode, or begin caching after the hunting period 805 has completed and the application is in settled mode as in 810. In general, if a decrease in time interval is detected, the response is not cached until the local or remote proxy can verify that a subsequent received response meets cacheability conditions.

In general, long poll hunting may or may not be performed by mobile apps or clients but the distributed system includes mechanisms to detect long poll hunting activity for application long polls and can simply ignore the long poll hunting requests and begin caching after the hunting period has elapsed and the long polls have settled at some constant or near constant interval value or apply logic to begin caching during the hunting period, thus enabling accelerated caching to enhance performance and improve user experience.

Figure 9:
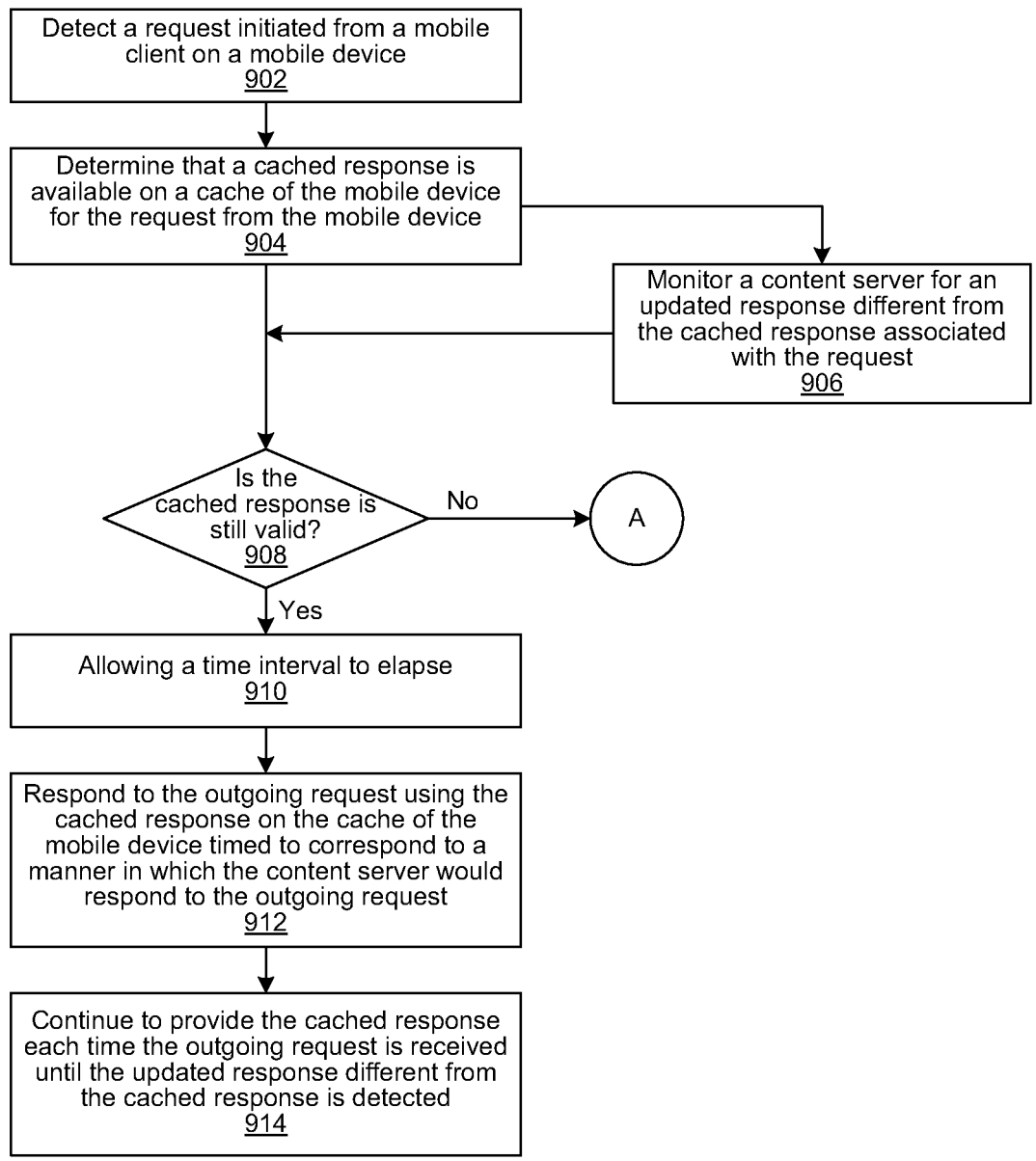
FIG. 9 depicts a flow chart illustrating an example process for caching content pushed to a mobile device (e.g., any wireless device) in a persistent connection from a content server over a wireless network (or broadband network).

FIG. 9 depicts a flow chart illustrating an example process for caching content pushed to a mobile device in a persistent connection from a content server over a wireless network.

In process 902, a request initiated from a mobile client on a mobile device is detected. The request is detected to be a long poll request (e.g., long-held request, long-held-HTTP request) or one for any type of persistent connection (e.g., enabling push emulation by the server, COMET style push, HTTP streaming, etc.).

In process 904, it is determined that a cached response is available on a cache of the mobile device for the request from the mobile device. In process 906, a content server is monitored for an updated response different from the cached response associated with the request, for example, by a proxy server able to establish wireless connectivity to the mobile device.

In process 908, it is determined whether the cached response is still valid, prior to responding to the outgoing request using the cached response. If not, the process flow continues to process 'A' continued in the example of FIG. 10. The updated content/response for the outgoing request can be detected by the proxy server and also optionally cached at the proxy server for retrieval by the mobile device.

If the cached response is determined to be valid, in process 910, a time interval is allowed to elapse. The time interval can be determined by a poll request interval by detecting, for example, the two consecutive requests from an application which generated the outgoing request from the mobile device. The two consecutive requests can be tracked prior to detection of the outgoing request initiated from the application (e.g., a mobile application) on the mobile device.

In process 912, to the outgoing request is responded to, using the cached response on the cache of the mobile device timed to correspond to a manner in which the content server would respond to the outgoing request. Thus, the outgoing request can be filled without a need to send the outgoing request over the wireless network. However, even though that the request can be filled or is filled without the need to go over the network, the request may still be sent over the network, for other reasons.

The manner of response of the content server can be simulated by allowing the time interval to elapse before responding to the outgoing request with the cached response. In one embodiment, the time interval can be determined based on request characteristics of an application on the mobile device from which the outgoing request originates. In process 914, the cached response is continued to be provided each time the outgoing request is received until the updated response different from the cached response is detected.

Figure 10:
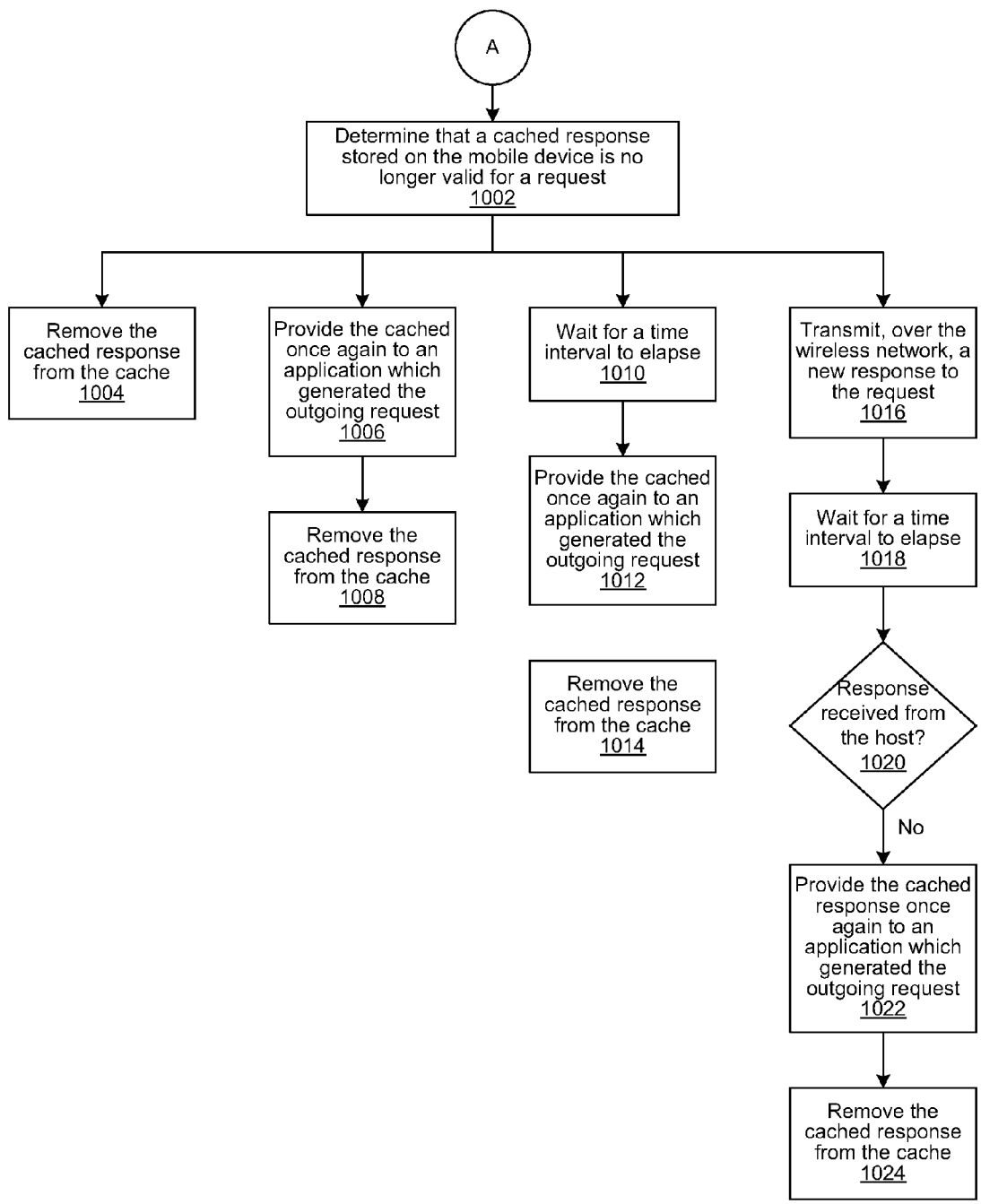
FIG. 10 depicts a diagram showing example processes that occur when removing a stored response from the local cache on a mobile device (e.g., any wireless device) for a long poll request.

FIG. 10 depicts a diagram showing example processes that occur when removing a stored response from the local cache on a mobile device for a long poll request.

In process 1002, it is determined that a cached response stored on the mobile device is no longer valid for a request. The cached response can be determined to be invalid for an outgoing request based on a notification received from a proxy server coupled to the content server, which monitors the content server for updated responses that are different from the cached response stored at the local cache on the mobile device.

In one example, the cached response is simply removed from the cache, in process 1004. In a second example, the cached response is provided again to an application which generated the outgoing request (immediately without waiting for a time interval), in process 1006, and then removed from the cache in 1008.

In another example, a time interval is allowed to elapse after determination of invalid cached response, in process 1010. Then, the cached is provided once again to an application which generated the outgoing request in step 1012, before removing the cached response from the cache in step 1014.

In yet another example, a new response to the request is transmitted over the wireless network in step 1016 after determining that a cached response stored on the mobile device is no longer valid for the request. A time interval is allowed to elapse in step 1018 before determining whether a response has been received from the host (step 1020. If not, the cached response (the one determined to be no longer valid) is provided once again to an application in step 1022 which generated the outgoing request prior to removal from the cache, in step 1024

Figure 11:
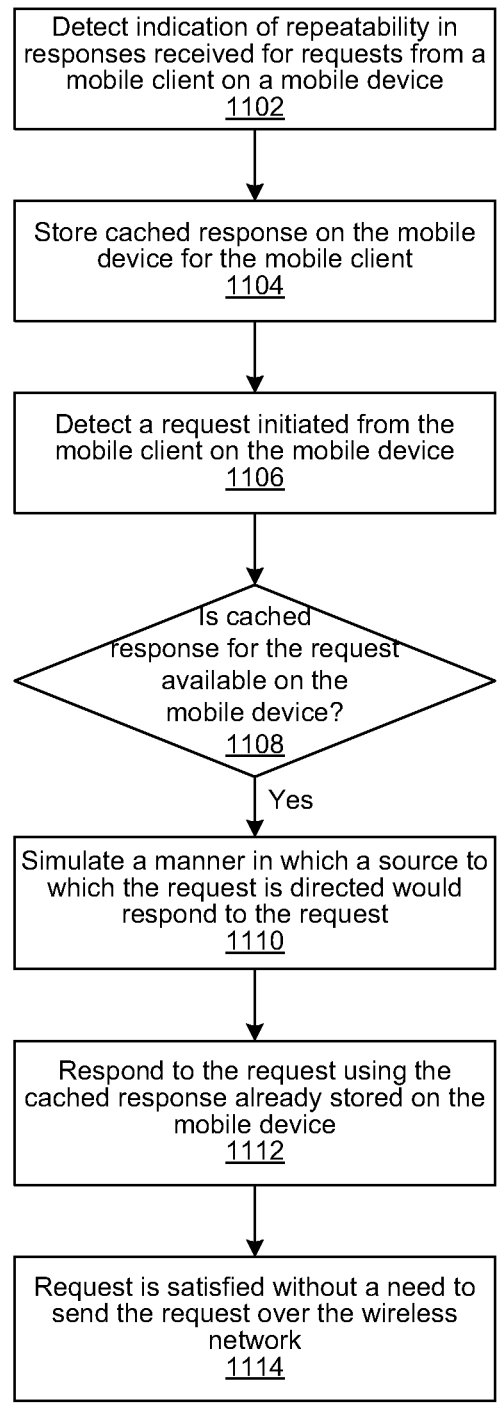
FIG. 11 depicts a flow chart illustrating an example process for using cached content provided over a long-held connection via a wireless network (or broadband network) to satisfy mobile client requests on a mobile device (e.g., any wireless device).

FIG. 11 depicts a flow chart illustrating an example process for using cached content provided over a long-held connection via a wireless network to satisfy mobile client requests on a mobile device.

In process 1102 indication of repeatability is detected in responses received for requests from a mobile client on a mobile device. In one embodiment, the repeatability can be determined when two responses received from the prior requests are the same. For example, hash values of the responses received for the prior requests are used to determined repeatability.

In process 1104, a cached response is stored on the mobile device for the mobile client, when the responses received in prior requests from the mobile client indicate repeatability in responses. In process 1106, a request initiated from the mobile client is detected on the mobile device. The request is detected to be one for a long-held connection over which content is pushed to the mobile client when available. The long held connection may be a long-held HTTP connection suited for content push from the content server.

In process 1108, it is determined whether the cached response for the request is available on the mobile device. If so, in process 1110, the manner in which a source to which the request is directed would respond to the request is simulated. In process 1112, the request is responded to using the cached response already stored on the mobile device. For example, the cached response already on the mobile device is provided to the mobile client after a time interval has elapsed. In process 1114, the request is satisfied without a need to send the request over the wireless network.

Concurrently and/or independently, a source which provides responses to requests of the mobile client can be monitored to determine relevancy of the cached response stored in the cache of the mobile device for the request. The source is monitored by an entity external from the mobile device.

Figure 12:
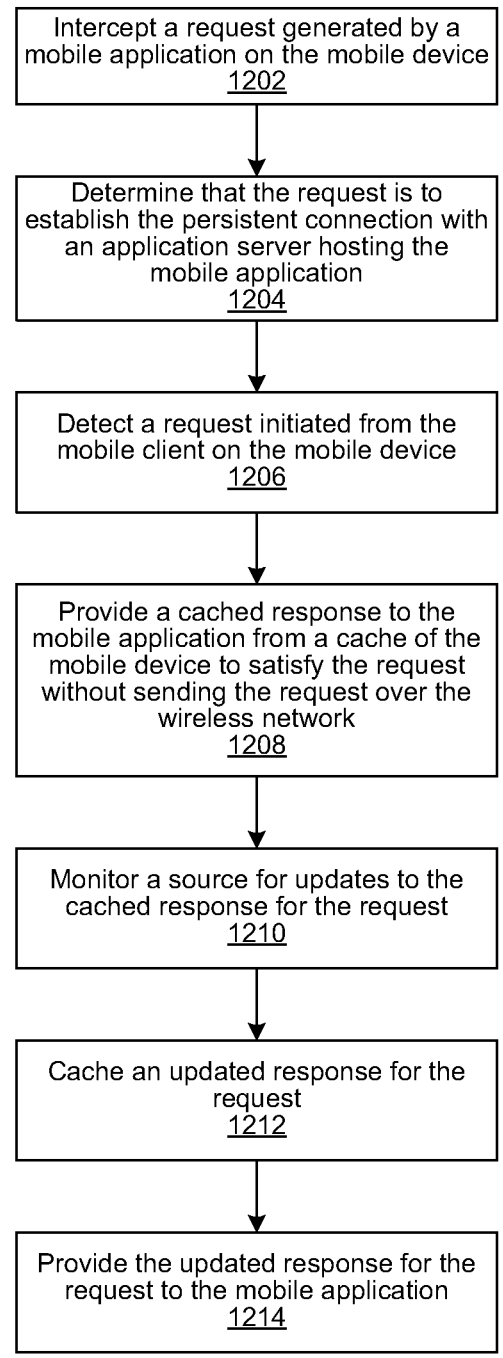
FIG. 12 depicts a flow chart illustrating an example process for caching content received at a mobile device (e.g., any wireless device) over a persistent connection over a wireless network (or broadband network).

FIG. 12 depicts a flow chart illustrating an example process for caching content received at a mobile device via a persistent connection over a wireless network.

In process 1202, a request generated by a application (e.g., a mobile application) on the mobile device is intercepted at the mobile device. The request can be intercepted by a local proxy on the mobile device. In process 1204, it is determined that the request is to establish the persistent connection with an application server hosting the application (e.g., a mobile application). The outgoing request can be detected to be for the persistent connection based on timing characteristics of prior requests generated by a same application or client on the mobile device.

The timing characteristics can include, one or more of, a response delay time to receive a response after a request has been sent and an idle time to send a subsequent request after the response has been received.

In one embodiment, the outgoing request is detected to be for the persistent connection based on a comparison of the response/delay time relative to the idle time. For example, the outgoing request is detected to be for the persistent connection when the idle time is short compared to the response/delay time. The outgoing request can also be detected to be for the persistent connection if the idle time indicates a immediate or near-immediate issuance of the subsequent request after receipt of the response.

In process 1206, a request (e.g., a long-held HTTP request) initiated from the mobile client is detected on the mobile device. In process 1208, a cached response is provided to the application (e.g., a mobile application) from a cache of the mobile device to satisfy the request without sending the request over the wireless network. The cached response can be provided to the application (e.g., a mobile application) after a time interval has elapsed. In process 1210, a source for updates to the cached response for the request is monitored. The cached response can be provided by a local proxy on the mobile device and the source can be monitored by a proxy server wirelessly coupled to the mobile device and able to communicate with the local proxy.

In process 1212, an updated response for the request is cached. The updated response for the request can be detected by the proxy server and stored at a remote cache on the proxy server. In addition, the updated response can be provided to the application (e.g., a mobile application) by the proxy server. The proxy server can notify local proxy that the cached response is no longer valid when updates to the cached response are detected from the source. In process 1214, the updated response for the request is provided to the application (e.g., a mobile application).

Figure 13:
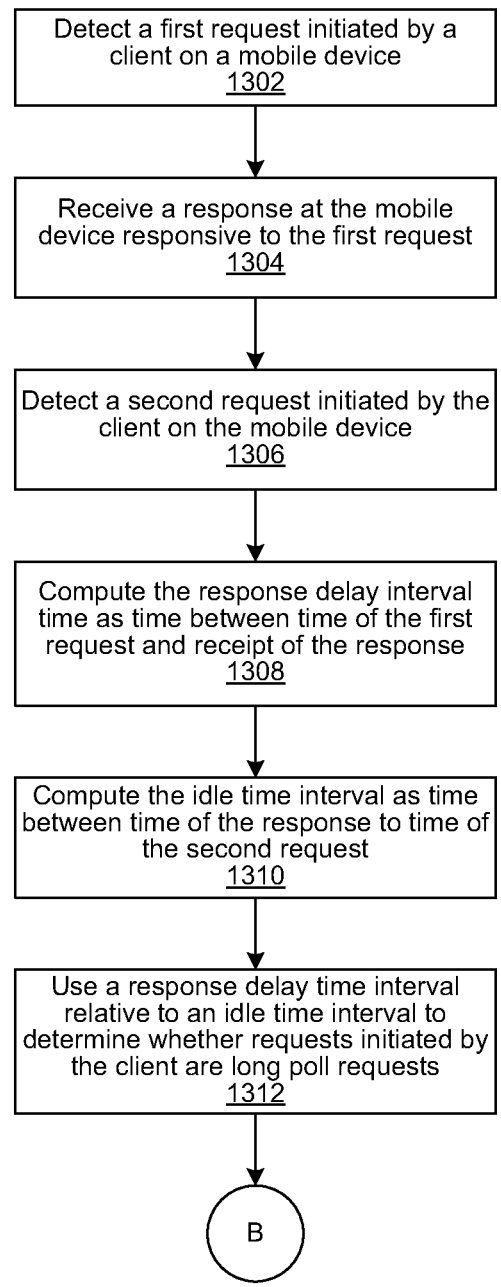
FIG. 13 depicts a flow chart illustrating an example process for detecting a long poll request initiated at a mobile device (e.g., any wireless device).

FIG. 13 depicts a flow chart illustrating an example process for detecting a long poll request initiated at a mobile device.

In process 1302, a first request initiated by a client on a mobile device is detected. In process 1304, a response is received at the mobile device responsive to the first request. In process 1306, a second request initiated by the client on the mobile device is detected. The second request is detected after the response is received, and it typically is the request immediately following the first request (e.g., no intervening requests between the first and second requests).

Figure 14:
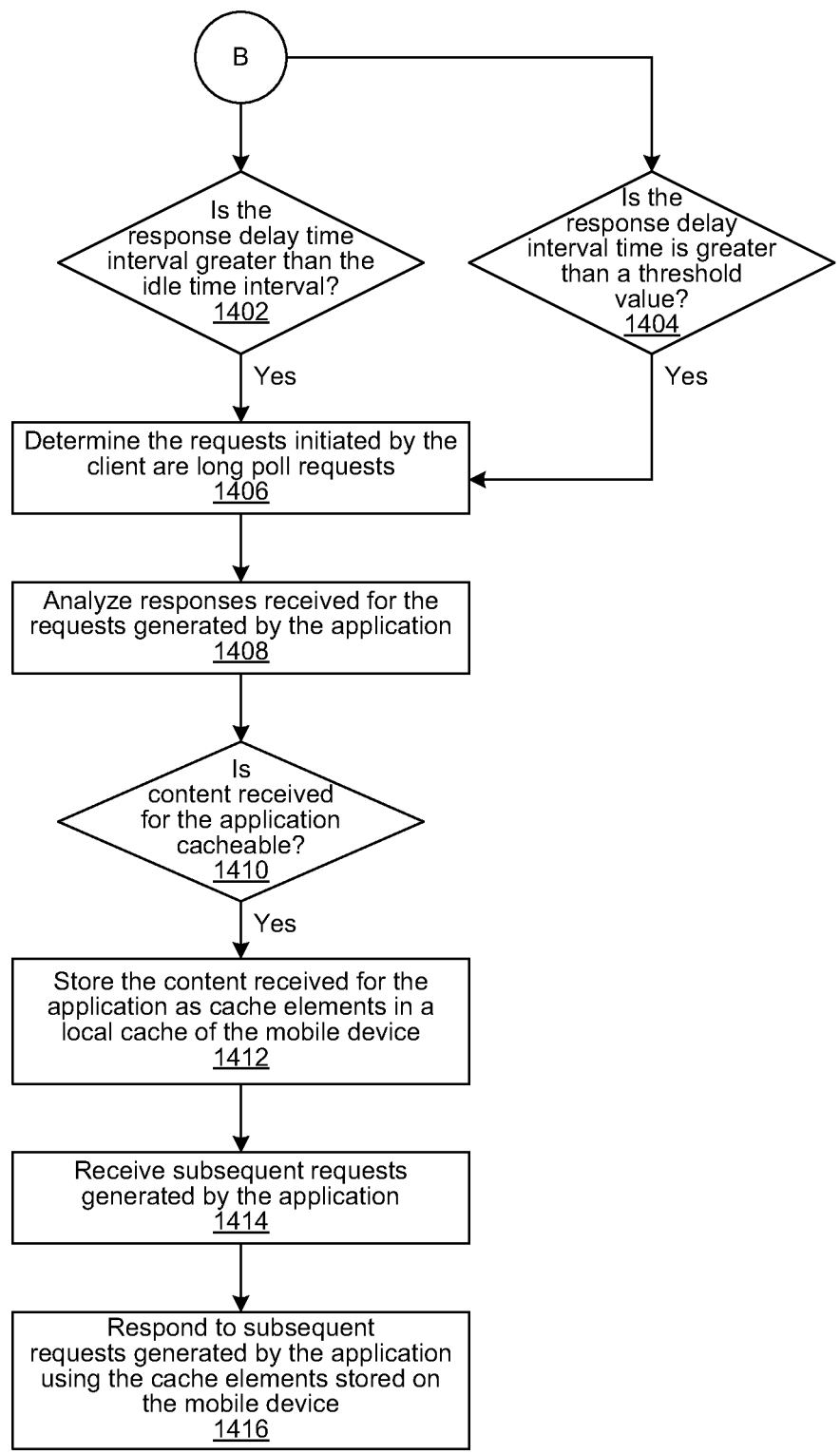
FIG. 14 depicts a flow chart illustrating an example process for determining whether to cache content received in long poll requests of an application on a mobile device using timing intervals in a request-response timing sequence.

In process 1308, the response/delay interval time is computed as time between the time of the first request and receipt of the response. In process 1310, the idle time interval is computed as time between the time of the response to time of the second request. In process 1312, a response/delay time interval relative to an idle time interval is used to determine whether requests initiated by the client are long poll requests. The process can continue at flow B as illustrated in FIG. 14 to illustrate additional example processes for identifying a long poll and content caching and serving content from the cache.

Note that after detection of first and second requests, and simultaneous with or after the processing thereof, a third request from the application can be detected. Based on the third request, a trend can be determined, identified, or estimated in response/delays based on when responses for the second and third requests are received.

The trend may indicate an increase in response/delays, and in one embodiment, the increase indicates cacheability for the long poll requests and a third response received is stored as cache elements in a local cache. Similarly, if the trend indicates that the response delays are constant or substantially constant then the repeatability criteria for caching are met and a third response received can be stored as cache elements in a local cache. In general, substantially constant response/delay includes a tolerance within 0-5%, 5-10%, 10-15%, or 15-20% of one of the response/delays.

Note that content received for the application is determined to be cacheable when the received responses indicate repeatability. For example, a third response is received to the third request; and repeatability can be indicated when the first, second, and third responses are the same. Alternatively, repeatability criteria may be met when any two out of the first, second, and third responses are the same. In the case of two responses where the first response is received to the first request, a second response is received to the second request, repeatability can be indicated when the first and second responses are the same.

In one embodiment, in response to detecting at least one decreasing delay interval from the trend, any response received for the requesting application may not be cached yet until a next request (e.g., fourth request or any subsequent requests) is received. The request may be cached upon the next request-response sequence which increases in delay interval compared to the prior decreasing delay interval. For example, a response received for the fourth request or any subsequent request can be cached responsive to detection of an increase in delay interval from the previous delay interval, for the fourth request-response delay.

The fourth response can be cached responsive to detecting repeatability in content with prior responses. For example, the fourth response is cached responsive to detecting that it is the same with at least one or two prior responses or cached responsive to detecting that it is the same with at least three prior responses.

FIG. 14 depicts a flow chart illustrating an example process for caching content received in long poll requests of an application on a mobile device using timing intervals in a request-response timing sequence.

In process 1402, it is determined whether the response/delay time interval is greater than the idle time interval. If so, the requests initiated by the client are determined to be long poll requests, as in step 1406.

In process 1404, it is determined, for example, if the response/delay interval time is greater than a threshold value. If so, the requests initiated by the client are determined to be long poll requests as in step 1406. In process 1406, it is determined that the requests initiated by the client are long poll requests (e.g., a long-held HTTP request, or any request suitable to emulate content push such as one for a persistent connection enabling COMET style push).

In general, the threshold value can be determined by the local proxy or another entity. In one embodiment, the threshold value is determined using response/delay interval times for requests generated by other clients. The other clients can be those that reside on the same mobile device and the threshold value can be determined by the local proxy on the mobile device.

Other clients can also reside on different mobile devices. The threshold can thus be determined by a proxy server which is external to the mobile device, and able to communicate over a wireless network with the different mobile devices. Both clients on the mobile device and clients on other devices can be used to determine the threshold, in combination or in separation.

In one embodiment, the threshold value can be determined, in part or in whole, based on network delays or other network-related latencies. The network delays can include delays in a cellular network or over the Internet, and can be determined by the local proxy and/or the proxy server. Indications and further information regarding mobile network delays (e.g., cell network) can be provided by cell service providers or carriers, for example.

In one embodiment, the threshold value is determined in part or in whole, based on delays of servers (e.g., the application server/content host 110 of FIG. 1A-B) to which the requests are directed, for example, due to internal delays (e.g., server upgrade, server maintenance, server malfunction, etc.) or network-related delays affecting the specific destination server.

In one embodiment, the relative timings can be determined by a local proxy on the mobile device and used by a proxy server remote from the mobile device to monitor a host to which the requests generated by the application are directed for updated responses different from those stored in the local cache for corresponding requests. Alternatively, the relative timings are detected by a proxy server remote from and coupled to the mobile device. In process 1408, responses received for the requests generated by the application are analyzed.

In process 1410, it is determined whether content received for the application is cacheable. The content can be determined to be cacheable, for example, when the received responses indicate repeatability. The local proxy and/or the proxy server can detect repeatability in the received response and determine that the content received for the application is cacheable. In one embodiment, hash values of the responses are compared to detect repeatability by a local proxy on the mobile device or by a proxy server remote from and coupled to the mobile device.

Repeatability can be determined when at least two responses received for the requests from the application are the same. In some instances, more than two same responses may be required to satisfy the requirement for content repeatability. The number of responses that need to be the same before caching begins may be set by default and be the same for all applications, or on a case by case basis with or without conditions and expiry time/dates.

In process 1412, the content received for the application is stored as cache elements in a local cache of the mobile device. In process 1414, subsequent requests generated by the application are received. In process 1416, subsequent requests generated by the application are responded to using the cache elements stored on the mobile device. The relative timings between responses and requests can be used when responding to requests using cached content on the mobile device to correspond to a manner in which the content server would respond to the outgoing request.

Figure 15:
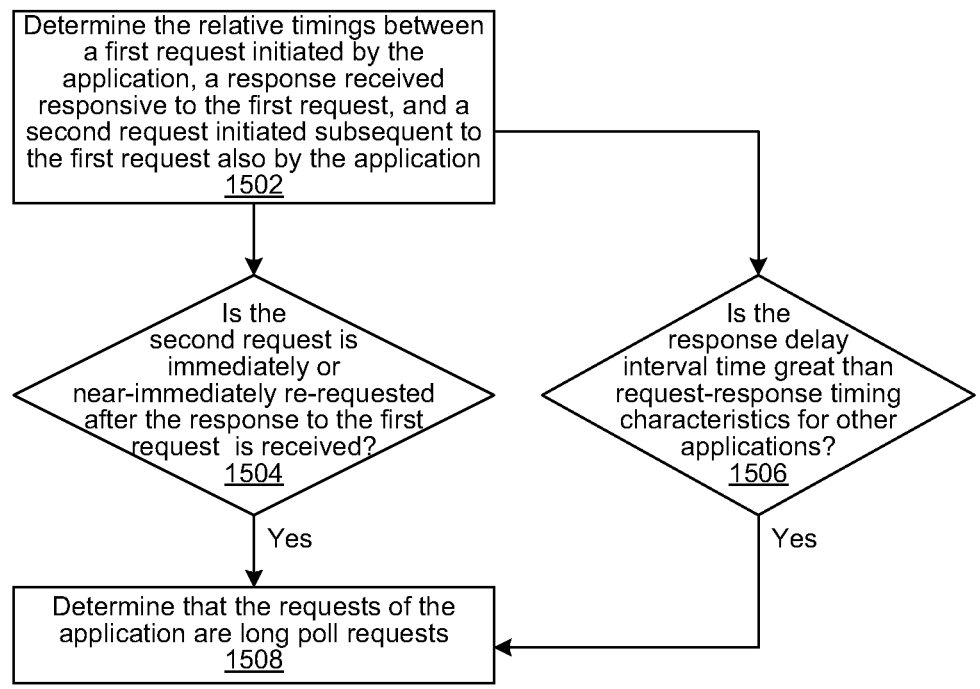
FIG. 15 depicts a flow chart illustrating an example process for detecting requests for a persistent connection (e.g., long poll requests, long-held HTTP requests, or HTTP streaming requests) from an application using relative timings in request-response timing sequences.

FIG. 15 depicts a flow chart illustrating an example process for detecting requests for a persistent connection (e.g., long poll requests, long-held HTTP requests, HTTP streaming requests) from an application using relative timings in request-response timing sequences.

In process 1502, the relative timings between a first request initiated by the application, a response received responsive to the first request, and a second request initiated subsequent to the first request also by the application are determined. In one embodiment, the relative timings can be used to determine whether requests generated by the application are long poll requests. Note that, in general, the first and second requests for use in computing the relative timings are selected for use after a long poll hunting period has settled or detected in the absence of a long poll hunting period. Alternatively, the first and second requests can be detected during a long poll hunting period and used to perform the analysis.

A timing diagram showing example timing characteristics of a long poll hunt is illustrated in the example of FIG. 8. The relative timings can be determined by for example, determining a first request time when the first request is initiated, determining a response time when the response to the first request is received, and/or determining a second request time when the second request, subsequent to the first request is initiated by the application.

In process 1504, it is determined if the second request is immediately or near-immediately re-requested after the response to the first request is received. If so, it can be determined that requests of the application are long poll requests or can be treated/processed/cached/managed as a long poll request, as in process 1508.

In process 1506, it is determined if the response/delay interval time is greater than request-response timing characteristics for other applications. If so, it can be determined that requests of the application are long poll requests or can be treated/processed/cached/managed as a long poll request, as in process 1508.

Figure 16:
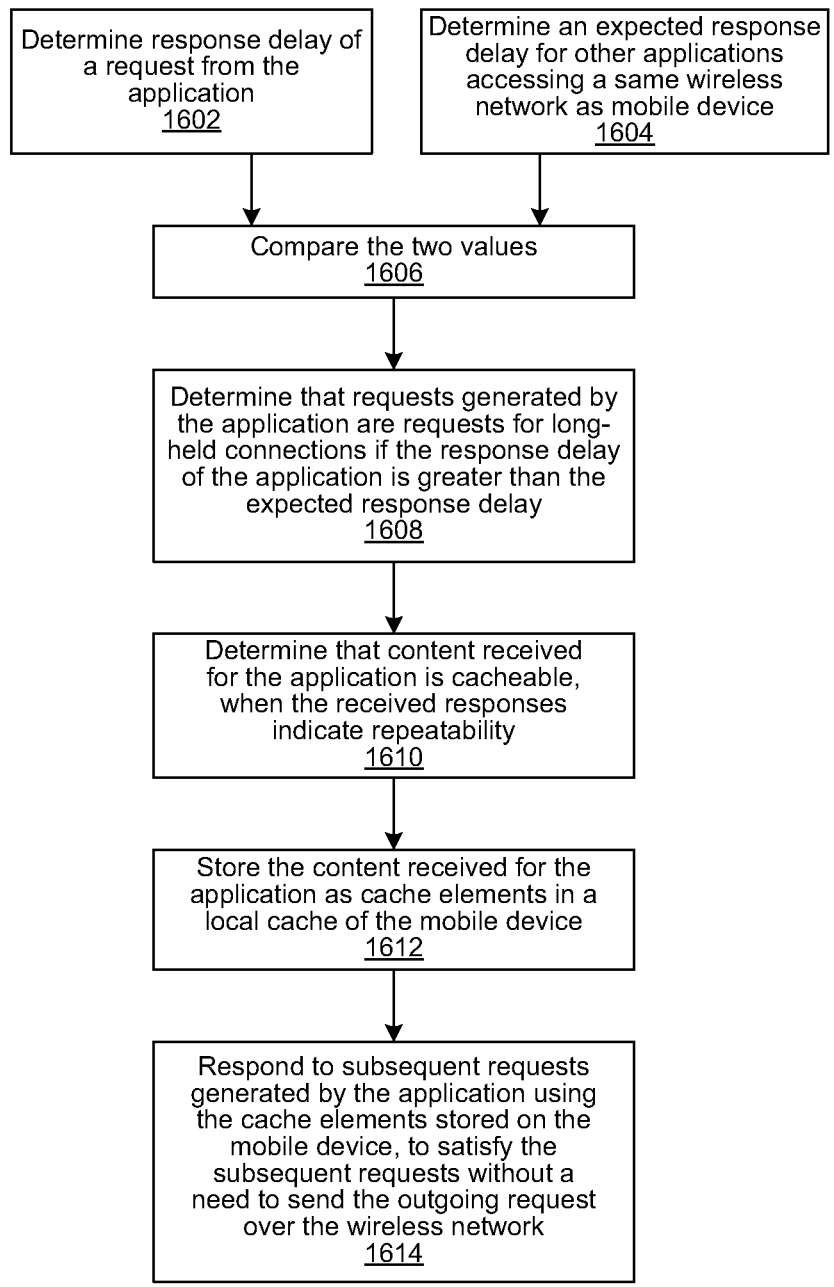
FIG. 16 depicts a flow chart illustrating an example process for determining whether to cache content received for an application over long-held connections on a mobile device.

FIG. 16 depicts a flow chart illustrating an example process for determining whether to cache content received for an application over long-held connections on a mobile device.

In process 1602, a response/delay of a request from the application is determined. The response/delay time is illustrated and labeled as time interval 'D' in the example request-response timing sequence shown in FIG. 17 (e.g., the amount of time elapsed between when a request is sent and when a response is detected). The response delay time, can in general, be determined by a local proxy (e.g., device-side proxy) and/or the server-side proxy (e.g., proxy server). The response/delay can be used alone or in combination with other timing characteristics to characterize applications or requests for use in setting polling intervals to optimize distributed caching.

In process 1604, an expected response/delay is determined for other applications accessing a same wireless network as mobile device. The other applications can reside on the same mobile device and/or include applications which reside on other mobile devices serviced by the same wireless network (e.g., the same network operator, carrier, service provider, and/or the same physical infrastructure, and/or the same logical network). In some instances, applications which reside on devices serviced by different wireless networks (e.g., different carriers or different physical networks)

In process 1606, the expected response/delay and the response/delay of the detected request is compared. In process 1608, it is determined that requests generated by the application are requests for long-held connections if the response/delay of the application is greater than the expected response/delay. As such it is determined that requests generated by the application are requests for long-held connections, or it is determined that requests generated by the application are to be processed and treated as requests for long-held connections.

In process 1610, it is determined that content received for the application is cacheable, when the received responses indicate repeatability. For example, in detecting a second response received for the second request, repeatability in timing of the first request and the first response, and of the second request and the second response can be detected if present. In process 1612, the content received for the application is stored as cache elements in a local cache of the mobile device, for example, if the timing for the request-response pairs is detected to be repeatable.

Note that in general, the caching can begin during long poll hunting (e.g., first, second, and/or subsequent requests are part of a long hung sequence and one or more of the responses are cached). Caching while the application is in the hunting period can accelerate or expedite the caching process (e.g., begin caching sooner) to enhance performance since cache elements on the local proxy on the mobile device can be used sooner to serve application requests. The caching may also occur in the absence of long poll hunts (e.g., the first and second requests are regular requests) or after long poll hunting has settled (e.g., the first and second requests described in this flow chart occur after the hunting period).

In process 1614, subsequent requests generated by the application are responded to using the cache elements stored on the mobile device, to satisfy the subsequent requests without a need to send the outgoing request over the wireless network. In responding to the subsequent requests using the cached response on the mobile device cache, the responses are provided in a manner that is timed to correspond to a manner in which a content server would respond, using the response/delay interval time.

Figure 17A:
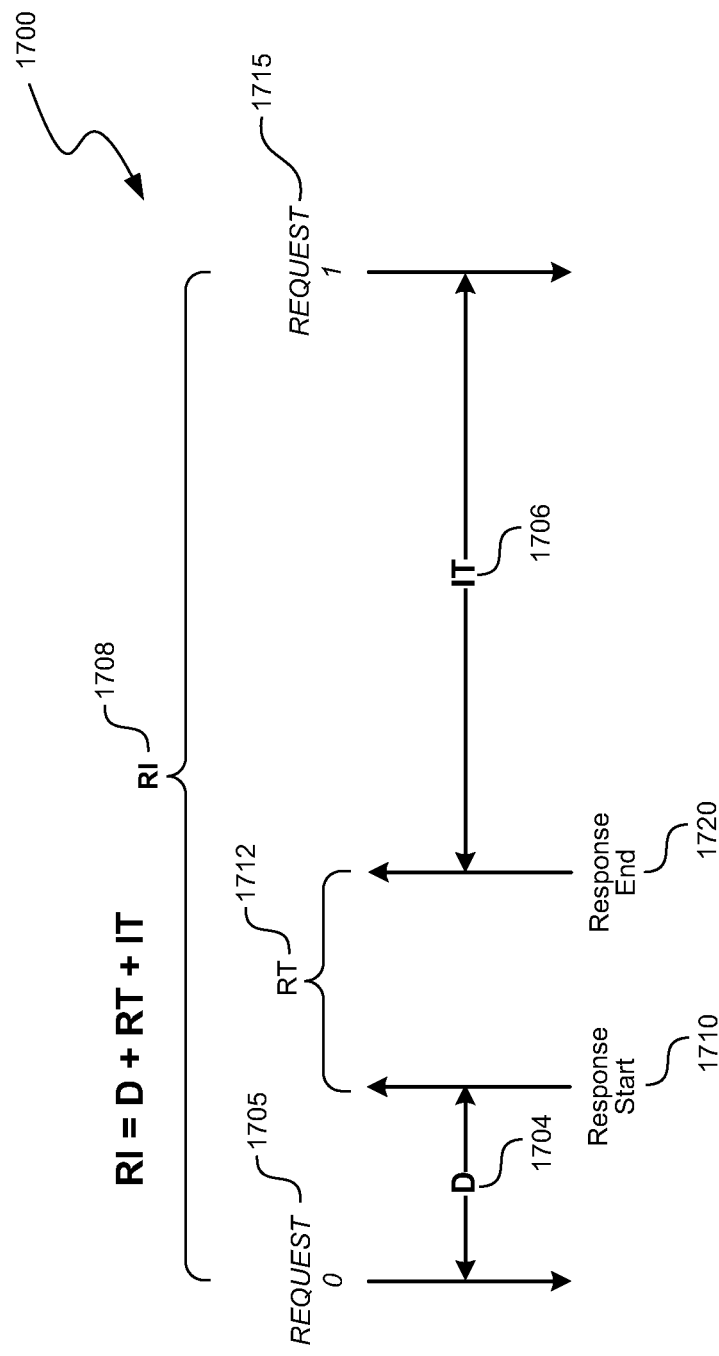
FIG. 17A depicts an example of a timing diagram showing timing characteristics for request-response sequences.
Figure 17B:
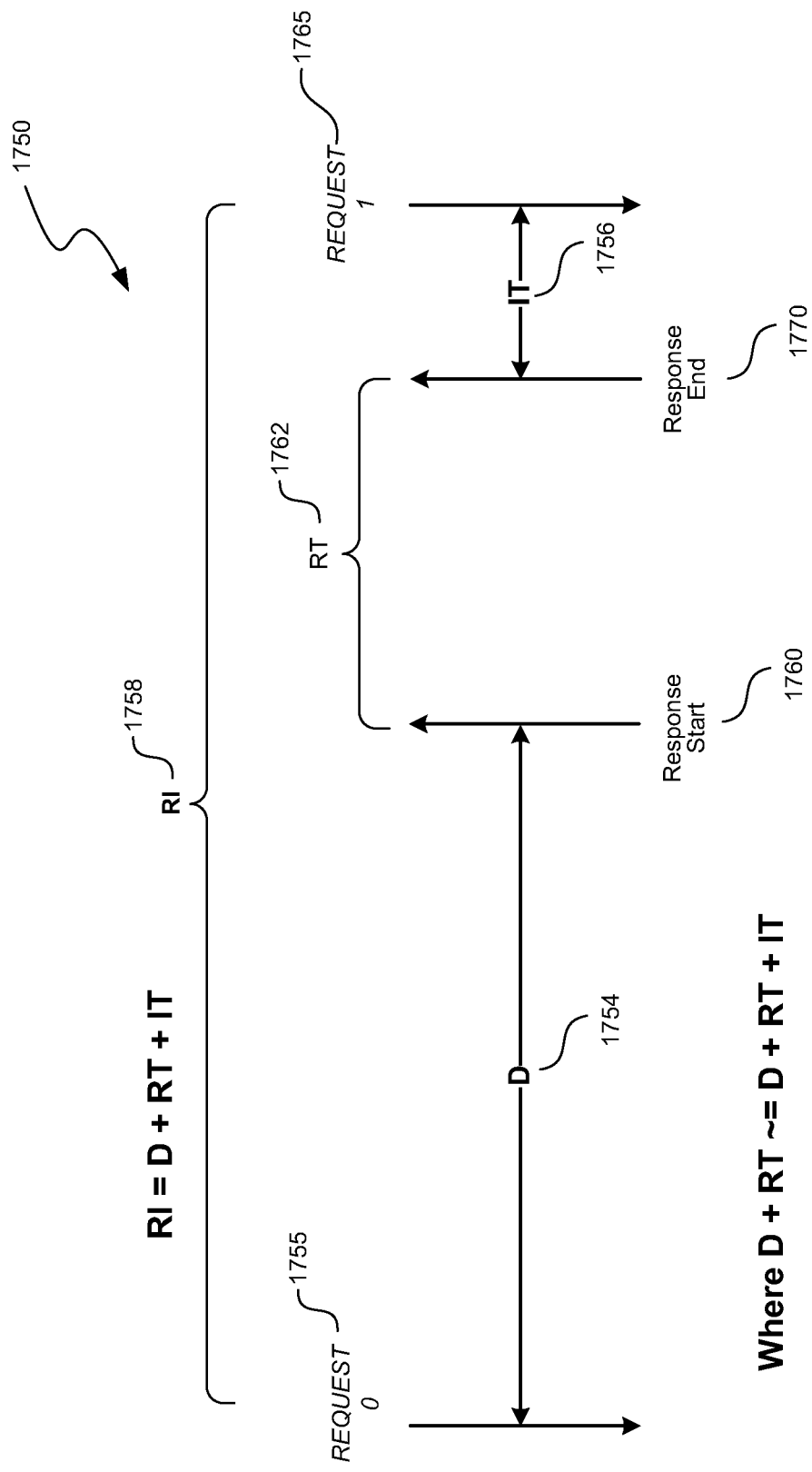
FIG. 17B depicts an example of a timing diagram showing timing characteristics for request-response sequences characteristic of a long poll.

FIG. 17A depicts an example of a timing diagram 1700 showing timing characteristics for request and response sequences.

The present technology includes a distributed caching model which involves cooperation of the device-side proxy and server-side. In order for it to work after caching a response, the client-side component needs to notify the server-side proxy and also providing a rate that a particular resource (application server/content provider) must be polled at (to verify validity of cached content). After receiving this notification, the server-side proxy can then monitor the resource for changes (validating resource) and, once a change is detected, the server-side component can notify the device-side component by sending an invalidation request.

The client-side component needs to provide a correct and suitable polling interval to the server-side proxy (e.g., the interval at which the server-side proxy is polling the resource to monitor it) for optimal performance, since if the polling interval is too low, the load is unnecessarily increased on the server-side proxy and by increasing the polling interval, the local proxy risks providing the expired/irrelevant information to the user at the user device.

As previously described, timing characteristics of request-responses sequences between a requesting client/application and content provider/application server can be used to determine application behavior and/or to categorize request type. Such information can be used to determine, identify, estimate, or predict an application's polling intervals such that an optimal polling interval that the server-side proxy needs to monitor the resource at can be determined and provided to the server-side proxy.

The timing characteristics can include, for example, response/delay time to receive a response after a request has been sent; and an idle time to send a subsequent request after the response has been received. The relationships of the various time intervals in a response-request sequence can be seen in the timing diagram 1700.

Each request-response time sequence can be described using all or some of the following events: 1) Start sending request (1705); 2) Request sent; 3) Response start (1710); 4) Response end (1720); 5) Next request send (1715). The 'Response Start' 1710) indicates when the first bytes of response (HEADER) arrived and the 'Response end 1715' indicates when all response content has been received.

Using these events, the device-side can calculate the following intervals shown in 1700:

1. RI 1708—Request interval—Time between "Request Sent 0" and "Request Sent 1."

2. D 1704—Delay—Time between 'Request sent' and "First bytes of response (HEADER) arrived."

3. IT 1706—Idle time—Time between 'Whole Response content received 0" and 'Request Sent 1"

4. RT 1712—Response time—Time between "First bytes of response (HEADER) arrived." and 'Whole Response content received"

The following relationship of the timing characteristic in a request-response sequence: RI=D+RT+IT can be considered to extract application behavior information for use in caching content in a distributed fashion. Relative comparisons between different intervals can also be used to characterize the application and its requests.

In general, the device-side component of the distributed proxy can keep track of individual timing intervals in a request-response sequence and compare the values, in a relative (e.g., bigger or smaller than another interval) or absolute manner (specific duration, long, short compared to a dynamic or static threshold value, etc.). The device-side component can track these interval values over time, check for stable components and determine or identify tendencies or patterns. For example, the device-side component can detect increasing or decreasing 'D' 1704 in the case of long poll hunting mode for long poll requests. FIG. 17B depicts an example of a timing diagram 1750 showing timing characteristics for request/response sequences characteristic of a long poll. Note that timing diagram 1750 may not be applicable to high latency long polls.

In one embodiment, a request can be detected, determined, or to be a long poll request based on a comparison of the response/delay time (D 1754) relative to the idle time (IT 1756) between request 0 1755 and response start time 1760. For example, the request can be detected to be a long poll request when the idle time is short compared to the response delay time (IT 1756<D 1754). The request can also be determined to be a long poll when IT 1756 is zero or substantially zero (~0).

In addition, the request can be determined or categorized as a long poll request if the idle time (IT 1756) indicates an immediate or near-immediate issuance of the subsequent request after receipt of the response (e.g., a short IT 1756). In addition, a request can be determined to be a long poll if RI 1758=D 1754+RT 1762+IT 1756~D 1754+RT 1762. In one embodiment, the response time 'RT' 1762 can be used to determine bit rate (e.g., size in byte*8/time).

Figure 18:
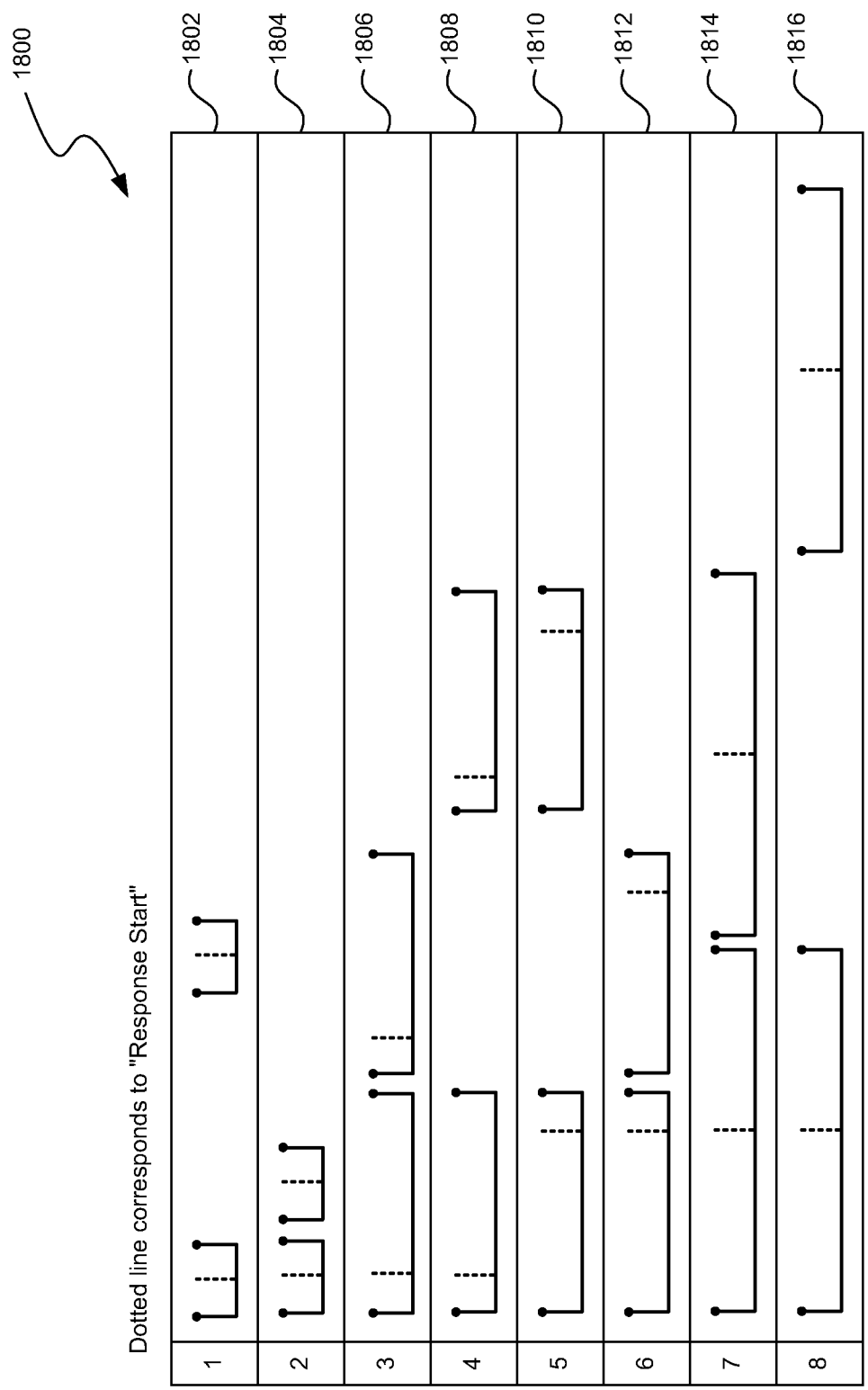
FIG. 18 depicts example timing diagrams showing timing characteristics for various types of request-response sequences.

In general, different combinations of time intervals provide indications about polling pattern of the specific application or request and can be used by the device-side component to generate a polling interval for the server-side component to use in monitoring the content source. FIG. 18 depicts example timing diagrams 1800 showing timing characteristics for various types of request-response sequences.

In the figure, 8 time line combinations are illustrated, each containing 2 blocks of request-response sequences. In each sequence, the dotted line indicates a response in a request-response interval. Sequence 1802 is characterized by a short 'D', short 'RT', and long 'IT'. Thus sequence 1802 may be a typical poll. Sequence 1804 is characterized by a short 'D', a short 'RT', a short 'IT' and is indicative of a high polling rate. Sequence 1804 may also indicate that a user is actively interacting with the application and/or actively refreshing the application.

Sequence 1806 is characterized by a short 'D', a long 'RT' and short 'IT,' which can indicate possible streaming. Sequence 1808 is characterized by a short 'D', a long 'RT, and a long 'IT' which can indicate polling of large content. Sequence 1810 is characterized by a long 'D,' a short 'RT,' and a long 'IT, which may indicate a long poll with high latency allowed on the application level.

Sequence 1812, which has a long 'D', a short 'RT', and a short 'IT' may indicate a long poll. Sequence 1814, having a long 'D', long 'RT' and short 'IT' can indicate streaming or long poll of large content. Sequence 1816 has a long 'D' a 'long 'RT', and long 'IT' can be a combination of 1814 and 1810.

Figure 19:
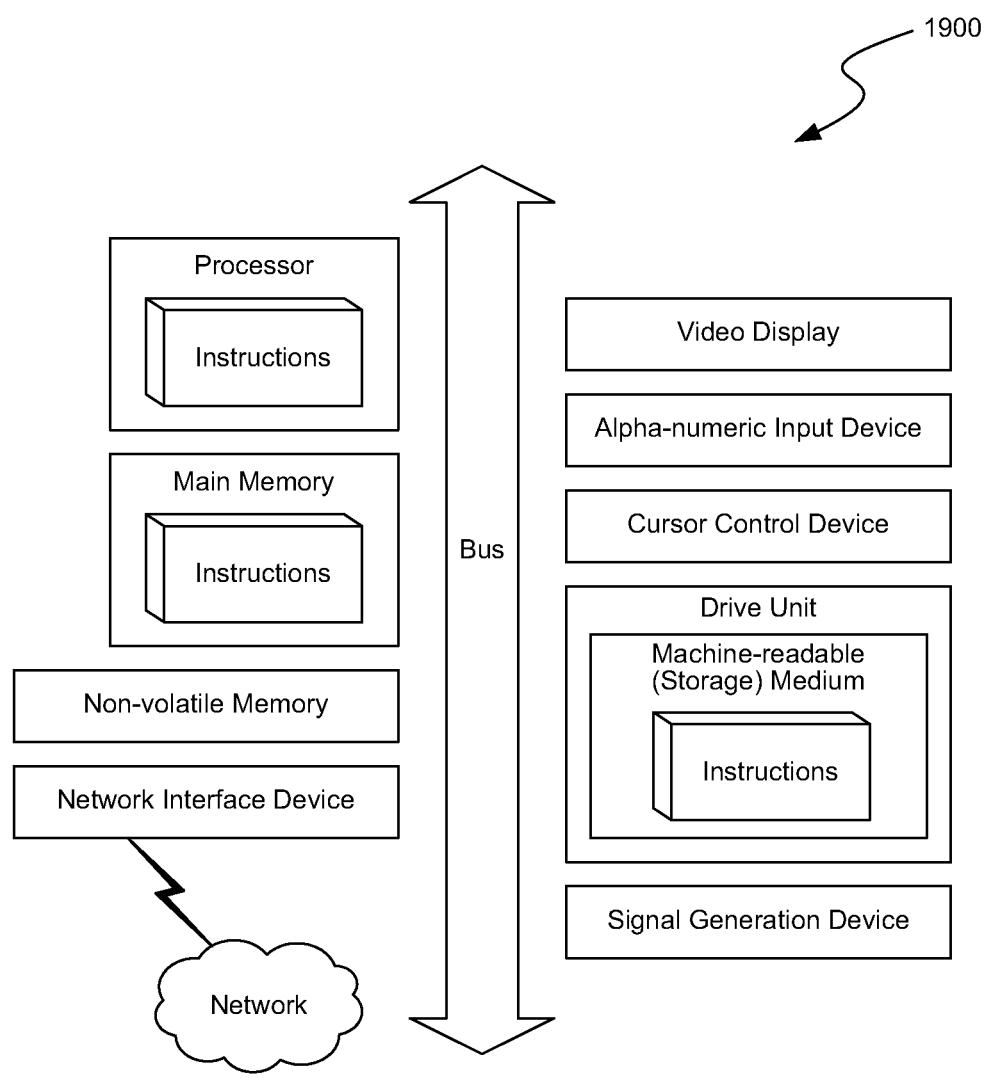
FIG. 19 shows a diagrammatic representation of a machine in the example form of a computer system within which a set of instructions, for causing the machine to perform any one or more of the methodologies discussed herein, may be executed.

FIG. 19 shows a diagrammatic representation of a machine in the example form of a computer system within which a set of instructions, for causing the machine to perform any one or more of the methodologies discussed herein, may be executed.

In alternative embodiments, the machine operates as a standalone device or may be connected (e.g., networked) to other machines. In a networked deployment, the machine may operate in the capacity of a server or a client machine in a client-server network environment, or as a peer machine in a peer-to-peer (or distributed) network environment.

The machine may be a server computer, a client computer, a personal computer (PC), a user device, a tablet PC, a laptop computer, a set-top box (STB), a personal digital assistant (PDA), a cellular telephone, an iPhone, an iPad, a Blackberry, a processor, a telephone, a web appliance, a network router, switch or bridge, a console, a hand-held console, a (hand-held) gaming device, a music player, any portable, mobile, hand-held device, tablet, or any machine capable of executing a set of instructions (sequential or otherwise) that specify actions to be taken by that machine.

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, may be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include but are not limited to recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above detailed description of embodiments of the disclosure is not intended to be exhaustive or to limit the teachings to the precise form disclosed above. While specific embodiments of, and examples for, the disclosure are described above for illustrative purposes, various equivalent modifications are possible within the scope of the disclosure, as those skilled in the relevant art will recognize. For example, while processes or blocks are presented in a given order, alternative embodiments may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times. Further any specific numbers noted herein are only examples: alternative implementations may employ differing values or ranges.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference. Aspects of the disclosure can be modified, if necessary, to employ the systems, functions, and concepts of the various references described above to provide yet further embodiments of the disclosure.

These and other changes can be made to the disclosure in light of the above Detailed Description. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the disclosure to the specific embodiments disclosed in the specification, unless the above Detailed Description section explicitly defines such terms. Accordingly, the actual scope of the disclosure encompasses not only the disclosed embodiments, but also all equivalent ways of practicing or implementing the disclosure under the claims.

While certain aspects of the disclosure are presented below in certain claim forms, the inventors contemplate the various aspects of the disclosure in any number of claim forms. For example, while only one aspect of the disclosure is recited as a means-plus-function claim under 35 U.S.C. §112, ¶6, other aspects may likewise be embodied as a means-plus-function claim, or in other forms, such as being embodied in a computer-readable medium. (Any claims intended to be treated under 35 U.S.C. §112, ¶6 will begin with the words "means for".) Accordingly, the applicant reserves the right to add additional claims after filing the application to pursue such additional claim forms for other aspects of the disclosure.

What is claimed is:

1. A method for detecting a long poll request initiated at a mobile device, the method comprising:
   detecting a first request initiated by a client on the mobile device;
   detecting a second request initiated by the client on the mobile device after a first response is received at the mobile device responsive to the first request;
   using a response delay time interval relative to an idle time interval to determine whether requests initiated by the client are long poll requests;
   wherein, the response delay time interval is between time of the first request and receipt of the first response responsive to the first request;
   wherein, the idle time interval is between time of the first response to time of the second request;
   wherein, the requests initiated by the client are determined to be long poll requests if the response delay time interval is greater than a threshold value;
   wherein, the threshold value is determined by a local proxy at the mobile device; and
   wherein a proxy server external to the mobile device is able to communicate over a wireless network with other different mobile devices.

2. The method of claim 1,
   detecting a third request, and detecting a trend in response delays based on when responses for the second and third requests are received;
   wherein, the trend indicates an increase in response delays;
   wherein, the increase indicates cacheability for the long poll requests and a third response received is stored as cache elements in a local cache; wherein, the trend indicates that the response delays are constant or substantially constant; wherein, the trend indicates cacheability for the long poll requests and a third response received is stored as cache elements in a local cache.

3. The method of claim 2, wherein, substantially constant includes a tolerance within 0-5%, 5-10%, 10-15%, or 15-20% of one of the response delays.

4. The method of claim 1, further comprising,
   in response to detecting at least one decreasing delay interval from the trend; waiting for a fourth request to be received;
   wherein, a fourth response received for the fourth request is cached responsive to detection of an increase in delay interval from the previous delay interval;
   the fourth response is cached responsive to detecting repeatability in content with prior responses.

5. The method of claim 4, the fourth response is cached responsive to detecting that it is the same with at least one or two prior responses.

6. The method of claim 1, further comprising:
   determining that content received for the client is cacheable, when the received responses indicate repeatability, using the responses received for the requests generated by the client;
   storing the content received for the client as cache elements in a local cache of the mobile device responsive to determining cache-ability;
   responding to subsequent requests generated by the client using the cache elements stored on the mobile device, to satisfy the subsequent requests without a need to send the outgoing request over a wireless network.

7. The method of claim 6, wherein, the first response is received response to the first request, a second response is received response to the second request, and repeatability is indicated when the first and second responses are the same.

8. The method of claim 6, further comprising,
   timing responses to the subsequent requests using the cached response on the cache of the mobile device to correspond to a manner in which a content server would respond, using the response delay interval time.

9. The method of claim 1, wherein, the third response is received response to the third request; and repeatability is indicated when the first, second, and third responses are the same or when any two out of the first, second, and third responses are the same.

10. The method of claim 1, wherein, the requests initiated by the client are determined to be long poll requests if the response delay time interval is greater than the idle time interval.

11. The method of claim 1, further comprising: determining the threshold value using response delay interval times for requests generated by other clients.

12. The method of claim 11 wherein, the other clients reside on the same mobile device and the threshold value is determined by a local proxy on the mobile device.

13. The method of claim 12, wherein, the other clients reside on different mobile devices.

14. The method of claim 11, further comprising, determining the threshold value based on network delays.

15. The method of claim 11, further comprising, determining the threshold value based on delays of servers to which the requests are directed.

16. A system for determining whether to cache content received from long poll requests of a mobile application residing on a mobile device, the system comprising:
   a processor coupled to a machine-readable memory configured to perform the following:
   detecting that requests generated by the mobile application are long poll requests using relative timings between a first request initiated by the mobile application, a first response received responsive to the first request, and a second request initiated subsequent to the first request also by the mobile application;
   determining that content received for the mobile application is cacheable, when the received responses indicate repeatability, using the responses received responsive to the requests generated by the mobile application;
   storing the content received for the mobile application as cache elements in a local cache of the mobile device responsive to determining that cache-ability;
   detecting a second response received for the second request; and
   detecting repeatability in timing of the first request and the first response and of the second request and the second response;
   wherein, the content received for the mobile application is stored as cache elements in the local cache of the mobile device if the timing is detected to be repeatable.

17. The system of claim 16, further comprising:
   responding to subsequent requests generated by the mobile application using the cache elements stored in the local cache, to satisfy the subsequent requests without a need to send the subsequent requests over a wireless network;
   wherein, the first and second requests for use in computing the relative timings are detected during a long poll hunting period.

18. The system of claim 16, wherein, the first and second requests for use in computing the relative timings are selected for use after a long poll hunting period has settled.

19. A machine-readable memory having stored thereon instructions which when executed by a processor causes the processor to perform a method for detecting requests for a persistent connection from an application, the method comprising:
   determining relative timings between a first request initiated by the application, a response received responsive to the first request, and a second request initiated subsequent to the first request also by the application;
   using the relative timings to determine whether requests generated by the application are long poll requests by comparing the relative timings to request-response timing characteristics for other applications;
   wherein, the relative timings are determined by:
      determining a first request time when the first request is initiated;
      determining a response time when the response for the first request is received; and
      determining a second request time when the second request, subsequent to the first request, initiated by the application;
   wherein, the application is a mobile client residing on a mobile device and the long poll requests are initiated over a cellular network.

20. The machine-readable memory of claim 19, wherein, the relative timings are used to determine whether the second request is immediately or near-immediately re-requested after the response to the first request is received.

21. A system for caching content received for long poll requests initiated at a mobile device, the system comprising:
   a local proxy on the mobile device which determines relative timings between requests initiated by an application;
   wherein, the relative timings are used to determine whether requests generated by the application are long poll requests;
   the local proxy further stores the content received for the application as cache elements in a local cache of the mobile device responsive to detection that at least two responses received for the requests from the application are the same;
   wherein, the relative timings are used by the local proxy remote from the mobile device to monitor a host to which the requests generated by the application are directed;
   wherein, the relative timings are determined using a first request initiated by the application, a response received responsive to the first request, and a second request initiated subsequent to the first request also by the application; wherein the first and second requests occur after a long poll hunting period or during a long poll hunting period.

22. The system of claim 21, further comprising a proxy server external to the mobile device, the proxy server being able to wirelessly communicate with the local proxy on the mobile device;
   wherein, the proxy server monitors a host for updated responses different from those stored in the local cache for corresponding requests initiated by the application on the mobile device;
   wherein, the proxy server monitors is able to wirelessly communicate with multiple mobile devices in a wireless network and monitor the host on behalf of multiple mobile devices running the same application;
   wherein, the local proxy responds to subsequent requests generated by the application using the cache elements stored on the mobile device, to satisfy the subsequent requests without a need to send the request over a wireless network.

* * * * *